(12) United States Patent
Maue et al.

(10) Patent No.: US 9,126,945 B2
(45) Date of Patent: Sep. 8, 2015

(54) N-(3-CARBAMOYLPHENLY)-1H-PYRAZOLE-5-CARBOXAMIDE DERIVATIVES AND THE USE THEREOF FOR CONTROLLING ANIMAL PESTS

(75) Inventors: Michael Maue, Langenfeld (DE); Isabelle Adelt, Haan (DE); Markus Heil, Leichlingen (DE); Peter Jeschke, Bergisch Gladbach (DE); Tobias Kapferer, Basel (CH); Friedrich August Mühlthau, Kelkheim-Fischbach (DE); Alexander Sudau, Langenfeld (DE); Olga Malsam, Rösrath (DE); Peter Lösel, Leverkusen (DE); Arnd Voerste, Köln (DE); Ulrich Görgens, Ratingen (DE)

(73) Assignee: BAYER INTELLECTUAL PROPERTY GMBH, MONHEIM (DE)

( * ) Notice: Subject to any disclaimer, the term of this patent is extended or adjusted under 35 U.S.C. 154(b) by 58 days.

(21) Appl. No.: 14/005,414

(22) PCT Filed: Mar. 12, 2012

(86) PCT No.: PCT/EP2012/054299
§ 371 (c)(1),
(2), (4) Date: Nov. 23, 2013

(87) PCT Pub. No.: WO2012/126766
PCT Pub. Date: Sep. 27, 2012

(65) Prior Publication Data
US 2014/0088153 A1    Mar. 27, 2014

Related U.S. Application Data

(60) Provisional application No. 61/454,134, filed on Mar. 18, 2011.

(30) Foreign Application Priority Data

Mar. 18, 2011 (EP) ..................... 11158838
Nov. 25, 2011 (EP) ..................... 11190693

(51) Int. Cl.

| | |
|---|---|
| C07D 231/14 | (2006.01) |
| C07D 401/12 | (2006.01) |
| C07D 231/18 | (2006.01) |
| C07D 231/16 | (2006.01) |
| A01N 43/56 | (2006.01) |
| C07C 237/38 | (2006.01) |
| C07C 255/46 | (2006.01) |

(52) U.S. Cl.
CPC .............. *C07D 231/14* (2013.01); *A01N 43/56* (2013.01); *C07C 237/38* (2013.01); *C07C 255/46* (2013.01); *C07D 231/16* (2013.01); *C07D 231/18* (2013.01); *C07D 401/12* (2013.01); *C07C 2101/02* (2013.01)

(58) Field of Classification Search
None
See application file for complete search history.

(56) References Cited

U.S. PATENT DOCUMENTS

2006/0069132 A1    3/2006    Armel et al.

FOREIGN PATENT DOCUMENTS

| EP | 1911751 | 4/2008 |
|---|---|---|
| WO | 00/07980 | 2/2000 |
| WO | 2004035545 | 4/2004 |
| WO | 2004106324 | 12/2004 |
| WO | 2008029084 | 3/2008 |
| WO | 2010/051926 | 3/2010 |

OTHER PUBLICATIONS

CAPLUS printout of Foreign Application Publication No. WO2008134969.*
Parlow et al. "Utility of Complementary Molecular Reactivity and Molecular Recognition (CMR/R) Technology and Polymer-Supported Reagents in the Solution-Phase Synthesis of Heterocyclic Carboxamides", J. Org. Chem (1997) vol. 62, No. 17, 5908-5919.
John Parlow "Synthesis of Pyrazolecarbonylaminopyridinecarboxamides as Herbicides", J. Heterocyclic Chem., (1998) vol. 35, 1493-1499.
International Search Report for PCT/EP2012/054299 Mailed Jun. 13, 2012.

* cited by examiner

*Primary Examiner* — Michael Barker
*Assistant Examiner* — Po-Chih Chen
(74) *Attorney, Agent, or Firm* — Miles & Stockbridge P.C.

(57) ABSTRACT

The invention relates to compounds of the general formula (I)

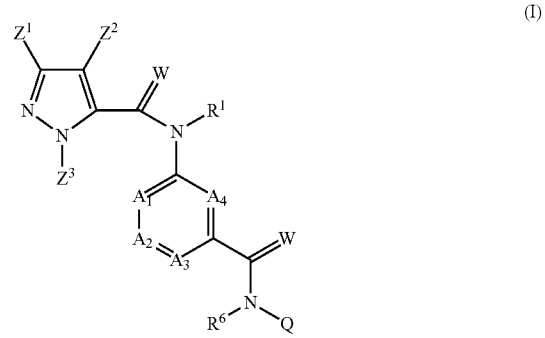

(I)

in which the radicals $A_1$, $A_2$, $A_3$, $A_4$, L, Q, $R^1$, T and W have the meaning given in the description and to the use of the compounds for controlling animal pests. The invention furthermore relates to processes and intermediates for preparing the compounds of formula (I).

12 Claims, No Drawings

N-(3-CARBAMOYLPHENLY)-1H-PYRAZOLE-5-CARBOXAMIDE DERIVATIVES AND THE USE THEREOF FOR CONTROLLING ANIMAL PESTS

CROSS REFERENCE TO RELATED APPLICATIONS

This application is a 371 application filed Nov. 23, 2013, which is a national stage application of PCT/EP2012/051299 filed Mar. 12, 2012, which claims priority to 61/454,134 filed Mar. 18, 2011; EP 11158838.0 filed Mar. 18, 2011; and EP 11190693.9 filed Nov. 25, 2011.

BACKGROUND OF THE INVENTION

1. Field of the Invention

The present application relates to novel halogen-substituted compounds, to processes for their preparation and to their use for controlling animal pests, in particular arthropods and especially insects, arachnids and nematodes.

2. Description of Related Art

It is known that certain halogen-substituted compounds have herbicidal action (cf. J. Org. Chem. 1997, 62(17), 5908-5919, J. Heterocycl. Chem. 1998, 35(6), 1493-1499, WO 2004/035545, WO 2004/106324, US 2006/069132, WO 2008/029084).

Furthermore, it is known that certain halogen-substituted compounds are insecticidally active (EP1911751).

In addition, it is known that certain halogen-substituted compounds have cytokine-inhibitory activities (WO 00/07980).

Modern crop protection compositions have to meet many demands, for example in relation to efficacy, persistence and spectrum of their action and possible use. Questions of toxicity, the combinability with other active compounds or formulation auxiliaries play a role, as well as the question of the expense that the synthesis of an active compound requires. Furthermore, resistances may occur. For all these reasons, the search for novel crop protection agents can never be considered as having been concluded, and there is a constant need for novel compounds having properties which, compared to the known compounds, are improved at least in respect of individual aspects.

SUMMARY

It was an object of the present invention to provide compounds which widen the spectrum of the pesticides under various aspects and/or improve their activity.

Surprisingly, it has now been found that certain halogen-substituted compounds and their N-oxides and salts have biological properties and are particularly suitable for controlling animal pests, and can therefore be employed particularly well in the agrochemical field and in the animal health sector.

Similar compounds are already known from WO 2010/051926.

The halogen-substituted compounds according to the invention are defined by the general formula (I)

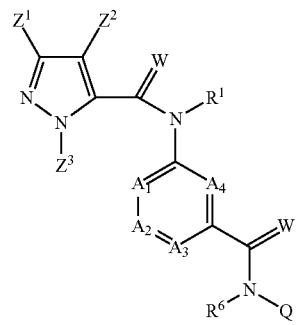

in which
$R^1$ represents hydrogen, optionally substituted $C_1$-$C_6$-alkyl, $C_2$-$C_6$-alkenyl, $C_2$-$C_6$-alkynyl, $C_3$-$C_7$-cycloalkyl, $C_1$-$C_6$-alkylcarbonyl, $C_1$-$C_6$-alkoxycarbonyl, cyano-$C_1$-$C_2$-alkyl, aryl-($C_1$-$C_3$)-alkyl, heteroaryl-($C_1$-$C_3$)-alkyl,
the chemical grouping
$A_1$ represents $CR^2$ or nitrogen,
$A_2$ represents $CR^3$ or nitrogen,
$A_3$ represents $CR^4$ or nitrogen and
$A_4$ represents $CR^5$ or nitrogen, but where not more than three of the chemical groupings $A_1$ to $A_4$ simultaneously represent nitrogen;
$R^2$, $R^3$, $R^4$ and $R^5$ independently of one another represent hydrogen, halogen, CN, $NO_2$, optionally substituted $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_1$-$C_6$-alkylamino, N,N-di-$C_1$-$C_6$alkylamino, N—$C_1$-$C_6$-alkylaminocarbonyl, N—$C_3$-$C_6$-cycloalkylaminocarbonyl or ($C_1$-$C_3$-alkoxy)carbonyl;
if none of the groupings $A_2$ and $A_3$ represents nitrogen, $R^3$ and $R^4$ together with the carbon atom to which they are attached may form a 5- or 6-membered ring which contains 0, 1 or 2 nitrogen atoms and/or 0 or 1 oxygen atom and/or 0 or 1 sulphur atom, or
if none of the groupings $A_1$ and $A_2$ represents nitrogen, $R^2$ and $R^3$ together with the carbon atom to which they are attached may form a 6-membered ring which contains 0, 1 or 2 nitrogen atoms;
W represents oxygen or sulphur;
$R^6$ represents hydrogen, optionally substituted $C_1$-$C_6$-alkyl, aryl-($C_1$-$C_3$)-alkyl, heteroaryl-($C_1$-$C_3$)-alkyl, $C_2$-$C_6$-alkenyl, $C_2$-$C_6$-alkynyl, $C_3$-$C_6$-cycloalkyl, ($C_1$-$C_3$-alkyl)-$C_3$-$C_6$-cycloalkyl and ($C_3$-$C_6$-cycloalkyl)-$C_1$-$C_3$-alkyl, $C_1$-$C_6$-alkylcarbonyl, $C_1$-$C_6$-alkoxycarbonyl;
Q represents

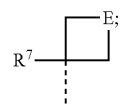

E represents a bond, —$CH_2$—, S, SO, $SO_2$, —S—$CH_2$—, —SO—$CH_2$—, —$SO_2$—$CH_2$—, —$CH_2$—S—$CH_2$—, —$CH_2$—SO—$CH_2$—, —$CH_2$—$SO_2$—$CH_2$—, —S—$CH_2$—$CH_2$—, —SO—$CH_2$—$CH_2$—, —$SO_2$—$CH_2$—$CH_2$—, —$NR^6$—$CH_2$—, —$CH_2$—$NR^6$—$CH_2$—;
$R^7$ represents cyano or C(=S)$NH_2$;

$Z^1$ represents optionally substituted $C_1$-$C_6$-haloalkyl or $C_3$-$C_6$-cycloalkyl, $C_3$-$C_6$-halocycloalkyl, and $Z^2$ represents halogen, cyano, nitro or optionally substituted $C_1$-$C_6$-haloalkyl, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, and $Z^3$ represents hydrogen or optionally substituted $C_1$-$C_6$-alkyl, $C_1$-$C_4$-alkenyl, $C_1$-$C_4$-alkynyl, $C_1$-$C_6$-haloalkyl;

DETAILED DESCRIPTION OF A PREFERRED EMBODIMENT

Preference is given to compounds of the formula (I)

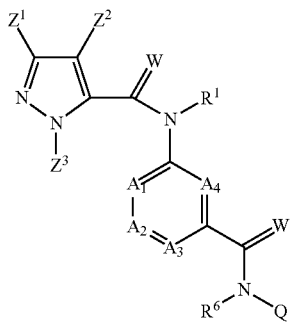

(I)

in which $R^1$ represents hydrogen, methyl, ethyl, n-propyl, isopropyl, n-butyl, isobutyl, s-butyl, t-butyl, methoxymethyl, ethoxymethyl, propoxymethyl, methylcarbonyl, ethylcarbonyl, n-propylcarbonyl, isopropylcarbonyl, s-butylcarbonyl, t-butylcarbonyl, methoxycarbonyl, ethoxycarbonyl, n-propoxycarbonyl, isopropoxycarbonyl, s-butoxycarbonyl, t-butoxycarbonyl, cyanomethyl, 2-cyanoethyl, benzyl, 4-methoxybenzyl, pyrid-2-ylmethyl, pyrid-3-ylmethyl, pyrid-4-ylmethyl, 4-chloropyrid-3-ylmethyl;

the chemical grouping $A_1$ represents $CR^2$ or nitrogen, $A_2$ represents $CR^3$ or nitrogen, $A_3$ represents $CR^4$ or nitrogen and $A_4$ represents $CR^5$ or nitrogen, but where not more than three of the chemical groupings $A_1$ to $A_4$ simultaneously represent nitrogen;

$R^2$ and $R^5$ independently of one another represent hydrogen, methyl, fluorine or chlorine and $R^3$ and $R^4$ independently of one another represent hydrogen, fluorine, chlorine, bromine, CN, $NO_2$, methyl, ethyl, fluoromethyl, difluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, methyl sulphonyl, methylsulphinyl, trifluoromethylsulphonyl, trifluoromethylsulphinyl; where W represents oxygen, $R^6$ represents hydrogen, methyl, ethyl, n-propyl, isopropyl, n-butyl, isobutyl, s-butyl, t-butyl, methoxymethyl, ethoxymethyl, propoxymethyl, methylcarbonyl, ethylcarbonyl, n-propylcarbonyl, isopropylcarbonyl, s-butylcarbonyl, t-butylcarbonyl, methoxycarbonyl, ethoxycarbonyl, n-propoxycarbonyl, isopropoxycarbonyl, s-butoxycarbonyl, t-butoxycarbonyl, cyanomethyl, 2-cyanoethyl, benzyl, 4-methoxybenzyl, pyrid-2-ylmethyl, pyrid-3-ylmethyl, pyrid-4-ylmethyl, 4-chloropyrid-3-ylmethyl;

Q represents

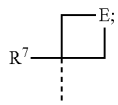

E represents a bond or —$CH_2$—;

$R^7$ represents cyano or $C(=S)NH_2$;

$Z^1$ represents difluoromethyl, trichloromethyl, chlorodifluoromethyl, dichlorofluoromethyl, trifluoromethyl, bromodichloromethyl, chloromethyl, bromomethyl, 1-fluoroethyl, 1-fluoro-1-methylethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-t-butyl, heptafluoro-n-propyl, heptafluoroisopropyl, nonafluoro-n-butyl, cyclopropyl, 1-chlorocyclopropyl, 1-fluorocyclopropyl, 1-bromocyclopropyl, 1-cyanocyclopropyl, 1-trifluoromethylcyclopropyl, cyclobutyl or 2,2-difluoro-1-methylcyclopropyl, and $Z^2$ represents halogen, cyano, nitro, difluoromethyl, trichloromethyl, chlorodifluoromethyl, dichlorofluoromethyl, trifluoromethyl, bromodichloromethyl, chloromethyl, bromomethyl, 1-fluoroethyl, 1-fluoro-1-methylethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-t-butyl, heptafluoro-n-propyl, heptafluoroisopropyl, nonafluoro-n-butyl, methylthio, methylsulphinyl, methylsulphonyl, ethylthio, ethylsulphinyl, ethylsulphonyl, trifluoromethylthio, trifluoromethylsulphinyl, trifluoromethylsulphonyl, and $Z^3$ represents hydrogen, methyl, ethyl, n-propyl, isopropyl, n-butyl, isobutyl, s-butyl, t-butyl, ethenyl, 1-propenyl, 2-propenyl, ethynyl, 1-propynyl, 1-butynyl, difluoromethyl, trichloromethyl, chlorodifluoromethyl, dichlorofluoromethyl, trifluoromethyl, chloromethyl, bromomethyl, 1-fluoroethyl, 1-fluoro-1-methylethyl, 2-fluoroethyl, 2,2-difluoroethyl, 2,2,2-trifluoroethyl;

Further particularly preferred compounds are compounds of the general formula (I) in which $Z^1$ represents trifluoromethyl, 1-chlorocyclopropyl, 1-fluorocyclopropyl or pentafluoroethyl, $Z^2$ represents trifluoromethyl, nitro, methylthio, methylsulphinyl, methylsulphonyl, fluorine, chlorine, bromine or iodine, $Z^3$ represents methyl, ethyl, n-propyl or hydrogen, $R^1$ represents hydrogen, methyl, ethyl, n-propyl, isopropyl, n-butyl, isobutyl, s-butyl, t-butyl, methoxymethyl, ethoxymethyl, propoxymethyl, methylcarbonyl, ethylcarbonyl, n-propylcarbonyl, isopropylcarbonyl, s-butylcarbonyl, t-butylcarbonyl, methoxycarbonyl, ethoxycarbonyl, n-propoxycarbonyl, isopropoxycarbonyl, s-butoxycarbonyl, t-butoxycarbonyl, cyanomethyl, 2-cyanoethyl, benzyl, 4-methoxybenzyl, pyrid-2-ylmethyl, pyrid-3-ylmethyl, pyrid-4-ylmethyl, 4-chloropyrid-3-ylmethyl, $A^1$, $A^2$ and $A^4$ represent CH, $A_3$ represents $CR^4$ and $R^4$ represents fluorine, chlorine, bromine or iodine, $R^6$ represents hydrogen, methyl, ethyl, n-propyl, isopropyl, n-butyl, isobutyl, s-butyl, t-butyl, W represents oxygen and Q represents 1-cyanocyclopropyl.

Preference is in particular given to further compounds in which
$Z^1$ represents trifluoromethyl, 1-chlorocyclopropyl, 1-fluorocyclopropyl or pentafluoroethyl,
$Z^2$ represents trifluoromethyl, chlorine or
$Z^3$ represents methyl,
$R^1$ represents hydrogen, methyl, ethyl,
$A^1$, $A^2$ and $A^4$ represent CH,
$A_3$ represents $CR^4$ and
$R^4$ represents chlorine,
$R^6$ represents hydrogen, methyl, ethyl,
W represents oxygen and
Q represents 1-cyanocyclopropyl.

The invention furthermore comprises novel compounds of the general formulae (IVa), (IVb), (Va), (Vb) as preferred starting materials for the synthesis of the compounds of the general formula (I).

The compounds of the general formulae (IVa) and (IVb) are preferred embodiments of the precursors of the general formula (IV) according to reaction schemes 1, 2 and 3, for example. The preparation of the compounds of the general formula (I) is, inter alia, preferably carried out using these compounds. The compounds of the general formula (IVb) are usually converted by reduction into the compounds (IVa).

The compounds (IVa) and (IVb) are defined by the general formulae below

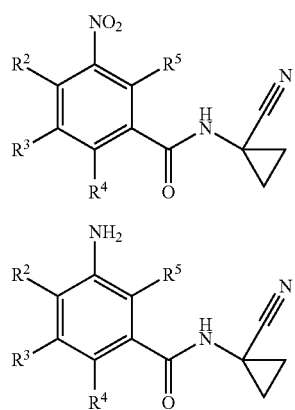

in which
$R^2$, $R^3$, $R^4$ and $R^5$ independently of one another represent hydrogen, halogen, cyano, nitro, optionally substituted $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_1$-$C_6$-alkylamino, N,N-di-$C_1$-$C_6$-alkylamino, N—$C_1$-$C_6$-alkylaminocarbonyl, N—$C_3$-$C_6$-cycloalkylaminocarbonyl or ($C_1$-$C_3$-alkoxy)carbonyl.

Preference is given to compounds of the general formulae (IVa), (IVb) in which
$R^2$ and $R^5$ represent hydrogen or halogen, and
$R^3$ and $R^4$ represent hydrogen, halogen, cyano, nitro, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl.

Particular preference is given to compounds of the general formulae (IVa), (IVb) in which
$R^2$ represents hydrogen or fluorine, and
$R^3$ represents hydrogen, fluorine, chlorine, bromine, iodine, cyano, nitro, methyl, ethyl, n-propyl, isopropyl, n-butyl, isobutyl, s-butyl, t-butyl, cyclopropyl, 1-chlorocyclopropyl, 1-fluorocyclopropyl, methylthio, trifluoromethylthio, methylsulphinyl, trifluoromethylsulphinyl, methylsulphonyl, trifluoromethylsulphonyl, and
$R^4$ represents hydrogen, fluorine, chlorine, bromine, iodine, cyano, nitro, methyl, ethyl, n-propyl, isopropyl, n-butyl, isobutyl, s-butyl, t-butyl, cyclopropyl, 1-chlorocyclopropyl, 1-fluorocyclopropyl, methylthio, trifluoromethylthio, methylsulphinyl, trifluoromethylsulphinyl, methylsulphonyl, trifluoromethylsulphonyl, and
$R^5$ represents hydrogen.

Very particular preference is given to compounds of the general formulae (IVa), (IVb) in which
$R^2$ and $R^5$ represent hydrogen, and
$R^3$ represents hydrogen, fluorine, chlorine, bromine, iodine, cyano, methyl, ethyl, methylthio, trifluoromethylthio, methylsulphinyl, trifluoromethylsulphinyl, methylsulphonyl, trifluoromethylsulphonyl, and
$R^4$ represents fluorine, chlorine, bromine, iodine, methyl, and
$R^5$ represents hydrogen.

The compounds of the general formulae (Va) and (Vb) are preferred embodiments of the precursors of the general formula (V) according to reaction schemes 1, 2 and 8, for example. The preparation of the compounds of the general formula (I) is, inter alia, preferably carried out using these compounds.

The compounds (Va) and (Vb) are defined by the general formulae below, in which

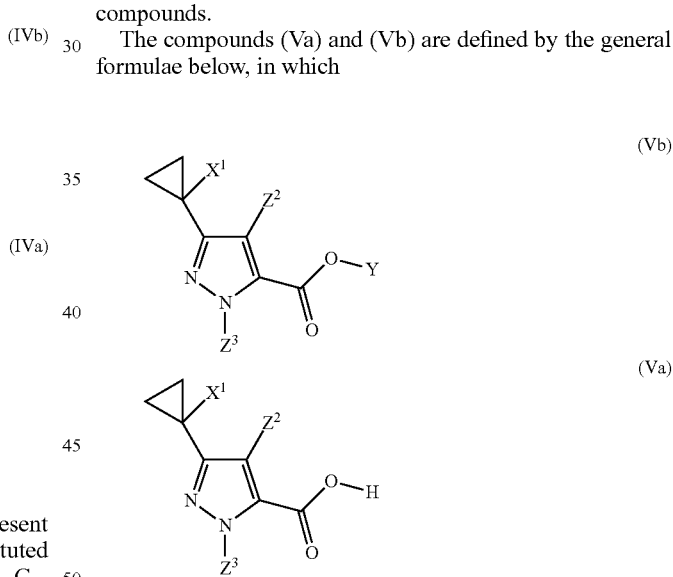

$X^1$ represents halogen, cyano and $C_1$-$C_4$-haloalkyl, and
$Z^2$ represents halogen, cyano, nitro or optionally substituted $C_1$-$C_6$-haloalkyl, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, and
$Z^3$ represents hydrogen or optionally substituted $C_1$-$C_6$-alkyl, $C_1$-$C_4$-alkenyl, $C_1$-$C_4$-alkynyl, $C_1$-$C_6$-haloalkyl, and
Y represents optionally substituted $C_1$-$C_6$-alkyl.

Preference is given to compounds of the general formulae (Va) and (Vb) in which
$X^1$ represents fluorine, chlorine, bromine, cyano and $C_1$-$C_2$-haloalkyl, and
$Z^2$ represents halogen, cyano, nitro, difluoromethyl, trichloromethyl, chlorodifluoromethyl, dichlorofluoromethyl, trifluoromethyl, bromodichloromethyl, chloromethyl, bromomethyl, 1-fluoroethyl, 1-fluoro-1-methylethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-t-butyl, heptafluoro-n-propyl, heptafluoroisopropyl, nonafluoro-n-butyl, methylthio, methylsulphinyl, methylsulphonyl, ethylthio, ethylsulphinyl, ethylsulphonyl, trifluoromethylthio, trifluoromethylsulphinyl, trifluoromethylsulphonyl, and $Z^3$ represents hydrogen, methyl, ethyl, n-propyl, isopropyl, n-butyl, isobutyl, s-butyl, t-butyl, ethenyl, 1-propenyl, 2-propenyl, ethynyl, 1-propynyl, 1-butynyl, difluoromethyl, trichloromethyl, chlorodifluoromethyl, dichlorofluoromethyl, trifluoromethyl, chloromethyl, bromomethyl, 1-fluoroethyl, 1-fluoro-1-methylethyl, 2-fluoroethyl, 2,2-difluoroethyl, 2,2,2-trifluoroethyl, and Y represents optionally substituted $C_1$-$C_6$-alkyl.

Particular preference is given to compounds of the general formulae (Va) and (Vb) in which $X^1$ represents fluorine, chlorine, trifluoromethyl or pentafluoroethyl, and $Z^2$ represents trifluoromethyl, nitro, methylthio, methylsulphinyl, methylsulphonyl, fluorine, chlorine, bromine or iodine, and $Z^3$ represents methyl, ethyl, n-propyl or hydrogen, and Y represents methyl, ethyl, n-propyl, isopropyl, n-butyl or t-butyl.

According to the invention, "alkyl"—on its own or as part of a chemical group—represents straight-chain or branched hydrocarbons preferably having 1 to 6 carbon atoms such as, for example, methyl, ethyl, n-propyl, isopropyl, n-butyl, isobutyl, s-butyl, t-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylpropyl, 1,3-dimethylbutyl, 1,4-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl and 2-ethylbutyl. Preference is furthermore given to alkyl groups having 1 to 4 carbon atoms such as, inter alia, methyl, ethyl, n-propyl, isopropyl, n-butyl, isobutyl, s-butyl or t-butyl. The alkyl groups according to the invention may be substituted by one or more identical or different radicals.

According to the invention, "alkenyl"—on its own or as part of a chemical group—represents straight-chain or branched hydrocarbons preferably having 2 to 6 carbon atoms and at least one double bond such as, for example, vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl. Preference is furthermore given to alkenyl groups having 2 to 4 carbon atoms such as, inter alia, 2-propenyl, 2-butenyl or 1-methyl-2-propenyl. The alkenyl groups according to the invention may be substituted by one or more identical or different radicals.

According to the invention, "alkynyl"—on its own or as part of a chemical group—represents straight-chain or branched hydrocarbons preferably having 2 to 6 carbon atoms and at least one triple bond such as, for example, 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-3-butynyl, 1,2-dimethyl-3-butynyl, 2,2-dimethyl-3-butynyl, 1-ethyl-3-butynyl, 2-ethyl-3-butynyl, 1-ethyl-1-methyl-2-propynyl and 2,5-hexadiynyl. Preference is furthermore given to alkynyl groups having 2 to 4 carbon atoms such as, inter alia, ethynyl, 2-propynyl or 2-butynyl-2-propynyl. The alkynyl groups according to the invention may be substituted by one or more identical or different radicals.

According to the invention, "cycloalkyl"—on its own or as part of a chemical group—represents mono-, bi- or tricyclic hydrocarbons preferably having 3 to 10 carbons such as, for example, cyclopropyl, cyclobutyl, cyclopentyl, cyclohexyl, cycloheptyl, cyclooctyl, bicyclo[2.2.1]heptyl, bicyclo[2.2.2]octyl or adamantyl. Preference is furthermore given to cycloalkyl groups having 3, 4, 5, 6 or 7 carbon atoms such as, inter alia, cyclopropyl or cyclobutyl. The cycloalkyl groups according to the invention may be substituted by one or more identical or different radicals.

According to the invention, "alkylcycloalkyl" represents mono-, bi- or tricyclic alkylcycloalkyl preferably having 4 to 10 or 4 to 7 carbon atoms such as, for example, ethylcyclopropyl, isopropylcyclobutyl, 3-methylcyclopentyl and 4-methylcyclohexyl. Preference is furthermore given to alkylcycloalkyl groups having 4, 5 or 7 carbon atoms such as, inter alia, ethylcyclopropyl or 4-methylcyclohexyl. The alkylcycloalkyl groups according to the invention may be substituted by one or more identical or different radicals.

According to the invention, "cycloalkylalkyl" represents mono-, bi- or tricyclic cycloalkylalkyl preferably having 4 to 10 or 4 to 7 carbon atoms such as, for example, cyclopropylmethyl, cyclobutylmethyl, cyclopentylmethyl, cyclohexylmethyl and cyclopentylethyl. Preference is furthermore given to cycloalkylalkyl groups having 4, 5 or 7 carbon atoms such as, inter alia, cyclopropylmethyl or cyclobutylmethyl. The cycloalkylalkyl groups according to the invention may be substituted by one or more identical or different radicals.

According to the invention, "halogen" represents fluorine, chlorine, bromine or iodine, in particular fluorine, chlorine or bromine.

The halogen-substituted chemical groups according to the invention such as, for example, haloalkyl, halocycloalkyl, haloalkyloxy, haloalkylthio, haloalkylsulphinyl or haloalkylsulphonyl are mono- or polysubstituted by halogen up to the maximum possible number of substituents. In the case of polysubstitution by halogen, the halogen atoms can be identical or different, and can all be attached to one or to a plurality of carbon atoms. Here, halogen represents in particular fluorine, chlorine, bromine or iodine, preferably fluorine, chlorine or bromine and particularly preferably fluorine.

According to the invention, "halocycloalkyl" represents mono-, bi- or tricyclic halocycloalkyl having preferably 3 to 10 carbon atoms such as, inter alia, 1-fluorocyclopropyl, 2-fluorocyclopropyl or 1-fluorocyclobutyl. Preference is furthermore given to halocycloalkyl having 3, 5 or 7 carbon atoms. The halocycloalkyl groups according to the invention may be substituted by one or more identical or different radicals.

According to the invention, "haloalkyl" "haloalkenyl" or "haloalkynyl" represents halogen-substituted alkyl, alkenyl or alkynyl groups having preferably 1 to 9 identical or different halogen atoms such as, for example, monohaloalkyl such as $CH_2CH_2Cl$, $CH_2CH_2F$, $CHClCH_3$, $CHFCH_3$, $CH_2Cl$, $CH_2F$; perhaloalkyl such as $CCl_3$ or $CF_3$ or $CF_2CF_3$; polyhaloalkyl such as $CHF_2$, $CH_2F$, $CH_2CHFCl$, $CHCl_2$, $CF_2CF_2H$, $CH_2CF_3$. This applies correspondingly to haloalkenyl and other halogen-substituted radicals. Haloalkoxy is, for example, $OCF_3$, $OCHF_2$, $OCH_2F$, $OCF_2CF_3$, $OCH_2CF_3$ and $OCH_2CH_2Cl$.

Further examples for haloalkyl groups are trichloromethyl, chlorodifluoromethyl, dichlorofluoromethyl, chloromethyl, bromomethyl, 1-fluoroethyl, 2-fluoroethyl, 2,2-difluoroethyl, 2,2,2-trifluoroethyl, 2,2,2-trichloroethyl, 2-chloro-2,2-difluoroethyl, pentafluoroethyl and pentafluoro-t-butyl. Preference is given to haloalkyl groups having 1 to 4 carbon atoms and 1 to 9, preferably 1 to 5, identical or different halogen atoms selected from the group consisting of fluorine, chlorine and bromine. Particular preference is given to haloalkyl groups having 1 or 2 carbon atoms and 1 to 5 identical or different halogen atoms selected from the group consisting of fluorine and chlorine such as, inter alia, difluoromethyl, trifluoromethyl or 2,2-difluoroethyl.

According to the invention, "hydroxyalkyl" represents a straight-chain or branched alcohol preferably having 1 to 6 carbon atoms such as, for example, methanol, ethanol, n-propanol, isopropanol, n-butanol, isobutanol, s-butanol and t-butanol. Preference is furthermore given to hydroxyalkyl groups having 1 to 4 carbon atoms. The hydroxyalkyl groups according to the invention may be substituted by one or more identical or different radicals.

According to the invention, "alkoxy" represents a straight-chain or branched O-alkyl preferably having 1 to 6 carbon atoms such as, for example, methoxy, ethoxy, n-propoxy, isopropoxy, n-butoxy, isobutoxy, s-butoxy and t-butoxy. Preference is furthermore given to alkoxy groups having 1 to 4 carbon atoms. The alkoxy groups according to the invention may be substituted by one or more identical or different radicals.

According to the invention, "haloalkoxy" represents halogen-substituted straight-chain or branched O-alkyl preferably having 1 to 6 carbon atoms such as, inter alia, difluoromethoxy, trifluoromethoxy, 2,2-difluoroethoxy, 1,1,2,2-tetrafluoroethoxy, 2,2,2-trifluoroethoxy and 2-chloro-1,1,2-trifluoroethoxy. Preference is furthermore given to haloalkoxy groups having 1 to 4 carbon atoms. The haloalkoxy groups according to the invention may be substituted by one or more identical or different radicals.

According to the invention, "alkylthio" represents a straight-chain or branched S-alkyl preferably having 1 to 6 carbon atoms such as, for example, methylthio, ethylthio, n-propylthio, isopropylthio, n-butylthio, isobutylthio, s-butylthio and t-butylthio. Preference is furthermore given to alkylthio groups having 1 to 4 carbon atoms. The alkylthio groups according to the invention may be substituted by one or more identical or different radicals.

Examples of haloalkylthioalkyl groups, i.e. halogen-substituted alkylthio groups, are inter alia difluoromethylthio, trifluoromethylthio, trichloromethylthio, chlorodifluoromethylthio, 1-fluoroethylthio, 2-fluoroethylthio, 2,2-difluoroethylthio, 1,1,2,2-tetrafluoroethylthio, 2,2,2-trifluoroethylthio or 2-chloro-1,1,2-trifluoroethylthio.

According to the invention, "alkylsulphinyl" represents straight-chain or branched alkylsulphinyl preferably having 1 to 6 carbon atoms such as, for example, methylsulphinyl, ethylsulphinyl, n-propylsulphinyl, isopropylsulphinyl, n-butylsulphinyl, isobutylsulphinyl, s-butylsulphinyl and t-butylsulphinyl. Preference is furthermore given to alkylsulphinyl groups having 1 to 4 carbon atoms. The alkylsulphinyl groups according to the invention may be substituted by one or more identical or different radicals.

Examples of haloalkylsulphinyl groups, i.e. halogen-substituted alkylsulphinyl groups, are inter alia difluoromethylsulphinyl, trifluoromethylsulphinyl, trichloromethylsulphinyl, chlorodifluoromethylsulphinyl, 1-fluoroethylsulphinyl, 2-fluoroethylsulphinyl, 2,2-difluoroethylsulphinyl, 1,1,2,2-tetrafluoroethylsulphinyl, 2,2,2-trifluoroethylsulphinyl and 2-chloro-1,1,2-trifluoroethylsulphinyl.

According to the invention, "alkylsulphonyl" represents straight-chain or branched alkylsulphonyl preferably having 1 to 6 carbon atoms such as, for example, methylsulphonyl, ethylsulphonyl, n-propylsulphonyl, isopropylsulphonyl, n-butylsulphonyl, isobutylsulphonyl, s-butylsulphonyl and t-butylsulphonyl. Preference is furthermore given to alkylsulphonyl groups having 1 to 4 carbon atoms. The alkylsulphonyl groups according to the invention may be substituted by one or more identical or different radicals.

Examples of haloalkylsulphonyl groups, i.e. halogen-substituted alkylsulphonyl groups, are inter alia difluoromethylsulphonyl, trifluoromethylsulphonyl, trichloromethylsulphonyl, chlorodifluoromethylsulphonyl, 1-fluoroethylsulphonyl, 2-fluoroethylsulphonyl, 2,2-difluoroethylsulphonyl, 1,1,2,2-tetrafluoroethylsulphonyl, 2,2,2-trifluoroethylsulphonyl and 2-chloro-1,1,2-trifluoroethylsulphonyl.

According to the invention, "alkylcarbonyl" represents straight-chain or branched alkyl-C(=O) preferably having 2 to 7 carbon atoms such as methylcarbonyl, ethylcarbonyl, n-propylcarbonyl, isopropylcarbonyl, s-butylcarbonyl and t-butylcarbonyl. Preference is furthermore given to alkylcarbonyl groups having 1 to 4 carbon atoms. The alkylcarbonyl groups according to the invention may be substituted by one or more identical or different radicals.

According to the invention, "cycloalkylcarbonyl" represents straight-chain or branched cyclooalkylcarbonyl preferably having 3 to 10 carbon atoms in the cycloalkyl moiety such as, for example, cyclopropylcarbonyl, cyclobutylcarbonyl, cyclopentylcarbonyl, cyclohexylcarbonyl, cycloheptylcarbonyl, cyclooctylcarbonyl, bicyclo[2.2.1]heptyl, bicyclo[2.2.2]octylcarbonyl and adamantylcarbonyl. Preference is furthermore given to cycloalkylcarbonyl having 3, 5 or 7 carbon atoms in the cycloalkyl moiety. The cycloalkylcarbonyl groups according to the invention may be substituted by one or more identical or different radicals.

According to the invention, "alkoxycarbonyl"—alone or as a constituent of a chemical group—represents straight-chain or branched alkoxycarbonyl, preferably having 1 to 6 carbon atoms or having 1 to 4 carbon atoms in the alkoxy moiety such as, for example, methoxycarbonyl, ethoxycarbonyl, n-propoxycarbonyl, isopropoxycarbonyl, s-butoxycarbonyl and t-butoxycarbonyl. The alkoxycarbonyl groups according to the invention may be substituted by one or more identical or different radicals.

According to the invention, "alkylaminocarbonyl" represents straight-chain or branched alkylaminocarbonyl having preferably 1 to 6 carbon atoms or 1 to 4 carbon atoms in the alkyl moiety, such as, for example, methylaminocarbonyl, ethylaminocarbonyl, n-proylaminocarbonyl, isopropylaminocarbonyl, s-butylaminocarbonyl and t-butylaminocarbonyl. The alkylaminocarbonyl groups according to the invention may be substituted by one or more identical or different radicals.

According to the invention, "N,N-dialkylaminocarbonyl" represents straight-chain or branched N,N-dialkylaminocarbonyl having preferably 1 to 6 carbon atoms or 1 to 4 carbon atoms in the alkyl moiety, such as, for example, N,N-dimethylaminocarbonyl, N,N-diethylaminocarbonyl, N,N-di(n-propylamino)carbonyl, N,N-di(isopropylamino)carbonyl and N,N-di-(s-butylamino)carbonyl. The N,N-dialkyaminocarbonyl groups according to the invention may be substituted by one or more identical or different radicals.

According to the invention, "aryl" represents a mono-, bi- or polycyclic aromatic system having preferably 6 to 14, in particular 6 to 10 ring carbon atoms such as, for example, phenyl, naphthyl, anthryl, phenanthrenyl, preferably phenyl. Furthermore, aryl also represents polycyclic systems such as tetrahydronaphtyl, indenyl, indanyl, fluorenyl, biphenylyl, where the bonding site is on the aromatic system. The aryl groups according to the invention may be substituted by one or more identical or different radicals.

Examples for substituted aryls are the arylalkyl groups which may likewise be substituted by one or more identical or different radicals in the alkyl and/or aryl moiety. Examples for such arylalkyl groups are inter alia benzyl and 1-phenylethyl.

According to the invention, "heterocycle", "heterocyclic ring" or "heterocyclic ring system" represents a carbocyclic ring system having at least one ring in which at least one carbon atom is replaced by a heteroatom, preferably by a heteroatom from the group consisting of N, O, S, P, B, Si, Se, and which is saturated, unsaturated or heteroaromatic and may be unsubstituted or substituted by a substituent Z, where the point of attachment is located at a ring atom. Unless defined differently, the heterocyclic ring contains preferably 3 to 9 ring atoms, especially 3 to 6 ring atoms, and one or more, preferably 1 to 4, in particular 1, 2 or 3, heteroatoms in the heterocyclic ring, preferably from the group consisting of N, O, and S, although no two oxygen atoms should be directly adjacent. The heterocyclic rings usually contain not more than 4 nitrogen atoms and/or not more than 2 oxygen atoms and/or not more than 2 sulphur atoms. If the heterocyclyl radical or the heterocyclic ring is optionally substituted, it can be fused to other carbocyclic or heterocyclic rings. In the case of optionally substituted heterocyclyl, the invention also embraces polycyclic systems such as, for example, 8-azabicyclo[3.2.1]octanyl or 1-azabicyclo[2.2.1]heptyl. In the case of optionally substituted heterocyclyl, the invention also embraces spirocyclic systems such as, for example, 1-oxa-5-azaspiro[2.3]hexyl.

Heterocyclyl groups according to the invention are, for example, piperidinyl, piperazinyl, morpholinyl, thiomorpholinyl, dihydropyranyl, tetrahydropyranyl, dioxanyl, pyrrolinyl, pyrrolidinyl, imidazolinyl, imidazolidinyl, thiazolidinyl, oxazolidinyl, dioxolanyl, dioxolyl, pyrazolidinyl, tetrahydrofuranyl, dihydrofuranyl, oxetanyl, oxiranyl, azetidinyl, aziridinyl, oxazetidinyl, oxaziridinyl, oxazepanyl, oxazinanyl, azepanyl, oxopyrrolidinyl, dioxopyrrolidinyl, oxomorpholinyl, oxopiperazinyl and oxepanyl.

Heteroarylene, i.e. heteroaromatic systems, have a particular meaning. According to the invention, the term heteroaryl represents heteroaromatic compounds, i.e. completely unsaturated aromatic heterocyclic compounds which fall under the above definition of heterocycles. Preference is given to 5- to 7-membered rings having 1 to 3, preferably 1 or 2, identical or different heteroatoms from the group above. Heteroaryl groups according to the invention are, for example, furyl, thienyl, pyrazolyl, imidazolyl, 1,2,3- and 1,2,4-triazolyl, isoxazolyl, thiazolyl, isothiazolyl, 1,2,3-, 1,3,4-, 1,2,4- and 1,2,5-oxadiazolyl, azepinyl, pyrrolyl, pyridyl, pyridazinyl, pyrimidinyl, pyrazinyl, 1,3,5-, 1,2,4- and 1,2,3-triazinyl, 1,2,4-, 1,3,2-, 1,3,6- and 1,2,6-oxazinyl, oxepinyl, thiepinyl, 1,2,4-triazolonyl and 1,2,4-diazepinyl. The heteroaryl groups according to the invention may also be substituted by one or more identical or different radicals.

Substituted groups such as a substituted alkyl, alkenyl, alkynyl, cycloalkyl, aryl, phenyl, benzyl, heterocyclyl and heteroaryl radical are, for example, a substituted radical derived from the unsubstituted base structure, where the substituents are, for example, one or more, preferably 1, 2 or 3, radicals from the group of halogen, alkoxy, alkylthio, hydroxyl, amino, nitro, carboxyl or a group equivalent to the carboxyl group, cyano, isocyano, azido, alkoxycarbonyl, alkylcarbonyl, formyl, carbamoyl, mono- and N,N-dialkylaminocarbonyl, substituted amino such as acylamino, mono- and N,N-dialkylamino, trialkylsilyl and optionally substituted cycloalkyl, optionally substituted aryl, optionally substituted heterocyclyl, where each of the latter cyclic groups may also be bonded via heteroatoms or divalent functional groups as in the alkyl radicals mentioned, and alkylsulphinyl, including both enantiomers of the alkylsulphonyl group, alkylsulphonyl, alkylphosphinyl, alkylphosphonyl and, in the case of cyclic radicals (="cyclic skeleton"), also alkyl, haloalkyl, alkylthioalkyl, alkoxyalkyl, optionally substituted mono- and N,N-dialkylaminoalkyl and hydroxyalkyl.

The term "substituted groups", such as substituted alkyl etc., includes, as substituents, in addition to the saturated hydrocarbonaceous radicals mentioned, corresponding unsaturated aliphatic and aromatic radicals such as optionally substituted alkenyl, alkynyl, alkenyloxy, alkynyloxy, alkenylthio, alkynylthio, alkenyloxycarbonyl, alkynyloxycarbonyl, alkenylcarbonyl, alkynylcarbonyl, mono- and N,N-dialkenylaminocarbonyl, mono- and dialkynylaminocarbonyl, mono- and N,N-dialkenylamino, mono- and N,N-dialkynylamino, trialkenylsilyl, trialkynylsilyl, optionally substituted cycloalkenyl, optionally substituted cycloalkynyl, phenyl, phenoxy etc. In the case of substituted cyclic radicals with aliphatic components in the ring, cyclic systems with those substituents bonded to the ring by a double bond are also included, for example those having an alkylidene group such as methylidene or ethylidene, or an oxo group, imino group or substituted imino group.

When two or more radicals form one or more rings, these may be carbocyclic, heterocyclic, saturated, partly saturated, unsaturated, for example also aromatic and further substituted.

The substituents mentioned by way of example ("first substituent level") may, if they contain hydrocarbon-containing moieties, optionally be further substituted therein ("second substituent level"), for example by one of the substituents as defined for the first substituent level. Corresponding further substituent levels are possible. The term "substituted radical" preferably embraces just one or two substituent levels.

Preferred substituents for the substituent levels are, for example,
amino, hydroxy, halogen, nitro, cyano, isocyano, mercapto, isothiocyanato, carboxyl, carboxamide, $SF_5$, aminosulphonyl, alkyl, cycloalkyl, alkenyl, cycloalkenyl, alkynyl, N-monoalkylamino, N,N-dialkylamino, N-alkanoylamino, alkoxy, alkenyloxy, alkynyloxy, cycloalkoxy, cycloalkenyloxy, alkoxycarbonyl, alkenyloxycarbonyl, alkynyloxycarbonyl, aryloxycarbonyl, alkanoyl, alkenylcarbonyl, alkynylcarbonyl, arylcarbonyl, alkylthio, cycloalkylthio, alkenylthio, cycloalkenylthio, alkynylthio, alkylsulphenyl and alkylsulphinyl, where both enantiomers of the alkylsulphinyl group are included, alkylsulphonyl, N-monoalkylaminosulphonyl, N,N-dialkylaminosulphonyl, alkylphosphinyl, alkylphosphonyl, where in the case of alkylphosphinyl and alkylphosphonyl both enantiomers are included, N-alkylaminocarbonyl, N,N-dialkylaminocarbonyl, N-alkanoylaminocarbonyl, N-alkanoyl-N-alkylaminocarbonyl, aryl, aryloxy, benzyl, benzyloxy, benzylthio, arylthio, arylamino, benzylamino, heterocyclyl and trialkylsilyl.

Substituents composed of a plurality of substituent levels are preferably alkoxyalkyl, alkylthioalkyl, alkylthioalkoxy, alkoxyalkoxy, phenethyl, benzyloxy, haloalkyl, halocycloalkyl, haloalkoxy, haloalkylthio, haloalkylsulphinyl, haloalkylsulphonyl, haloalkanoyl, haloalkylcarbonyl, haloalkoxycarbonyl, haloalkoxyalkoxy, haloalkoxyalkylthio, haloalkoxyalkanoyl, haloalkoxyalkyl.

In the case of radicals having carbon atoms, preference is given to those having 1 to 6 carbon atoms, preferably 1 to 4 carbon atoms, especially 1 or 2 carbon atoms. Preference is generally given to substituents from the group of halogen, e.g. fluorine and chlorine, $(C_1-C_4)$-alkyl, preferably methyl or ethyl, $(C_1-C_4)$-haloalkyl, preferably trifluoromethyl, $(C_1-C_4)$-alkoxy, preferably methoxy or ethoxy, $(C_1-C_4)$-haloalkoxy, nitro and cyano. Particular preference is given here to the substituents methyl, methoxy, fluorine and chlorine.

Substituted amino such as mono- or disubstituted amino means a radical from the group of the substituted amino radicals which are N-substituted, for example, by one or two identical or different radicals from the group consisting of alkyl, hydroxy, amino, alkoxy, acyl and aryl; preferably N-mono- and N,N-dialkylamino, (for example methylamino, ethylamino, N,N-dimethylamino, N,N-diethylamino, N,N-di-n-propylamino, N,N-diisopropylamino or N,N-dibutylamino), N-mono- or N,N-dialkoxyalkylamino groups (for example N-methoxymethylamino, N-methoxyethylamino, N,N-di(methoxymethyl)amino or N,N-di(methoxyethyl)amino), N-mono- and N,N-diarylamino, such as optionally substituted anilines, acylamino, N,N-diacylamino, N-alkyl-N-arylamino, N-alkyl-N-acylamino and also saturated N-heterocycles; preference is given here to alkyl radicals having 1 to 4 carbon atoms; here, aryl is preferably phenyl or substituted phenyl; for acyl, the definition given further below applies, preferably $(C_1-C_4)$-alkanoyl. The same applies to substituted hydroxylamino or hydrazino.

According to the invention, the term "cyclic amino groups" embraces heteroaromatic or aliphatic ring systems having one or more nitrogen atoms. The heterocycles are saturated or unsaturated, consist of one or more optionally fused ring systems and optionally contain further heteroatoms such as, for example, one or two nitrogen, oxygen and/or sulphur atoms. Furthermore, the term also includes groups having a spiro ring or a bridged ring system. The number of atoms which form the cyclic amino groups is not limited, in the case of a one-ring system, for example, the groups can consist of 3 to 8 ring atoms, and in the case of a two-ring system of 7 to 11 atoms.

Examples of cyclic amino groups having saturated and unsaturated monocyclic groups having a nitrogen atom as heteroatom which may be mentioned are 1-azetidinyl, pyrrolidino, 2-pyrrolidin-1-yl, 1-pyrrolyl, piperidino, 1,4-dihydropyrazin-1-yl, 1,2,5,6-tetrahydropyrazin-1-yl, 1,4-dihydropyridin-1-yl, 1,2,5,6-tetrahydropyridin-1-yl, homopiperidinyl; examples of cyclic amino groups having saturated and unsaturated monocyclic groups having two or more nitrogen atoms as heteroatoms which may be mentioned are 1-imidazolidinyl, 1-imidazolyl, 1-pyrazolyl, 1-triazolyl, 1-tetrazolyl, 1-piperazinyl, 1-homopiperazinyl, 1,2-dihydropiperazin-1-yl, 1,2-dihydropyrimidin-1-yl, perhydropyrimidin-1-yl, 1,4-diazacycloheptan-1-yl; examples of cyclic amino groups having saturated and unsaturated monocyclic groups having one or two oxygen atoms and one to three nitrogen atoms as heteroatoms, such as, for example, oxazolidin-3-yl, 2,3-dihydroisoxazol-2-yl, isoxazol-2-yl, 1,2,3-oxadiazin-2-yl, morpholino, examples of cyclic amino groups having saturated and unsaturated monocyclic groups having one to three nitrogen atoms and one to two sulphur atoms as heteroatoms which may be mentioned are thiazolidin-3-yl, isothiazolin-2-yl, thiomorpholino, or dioxothiomorpholino; examples of cyclic amino groups having saturated and unsaturated fused cyclic groups which may be mentioned are indol-1-yl, 1,2-dihydrobenzimidazol-1-yl, perhydropyrrolo pyrazin-2-yl; examples of cyclic amino groups having spirocyclic groups which may be mentioned are 2-azaspiro[4,5]decan-2-yl; examples of cyclic amino groups having bridged heterocyclic groups which may be mentioned are 2-azabicyclo[2.2.1]heptan-7-yl.

Substituted amino also includes quaternary ammonium compounds (salts) with four organic substituents on the nitrogen atom.

Optionally substituted phenyl is preferably phenyl which is unsubstituted or mono- or polysubstituted, preferably up to trisubstituted, by identical or different radicals from the group of halogen, $(C_1-C_4)$-alkyl, $(C_1-C_4)$-alkoxy, $(C_1-C_4)$-alkoxy-$(C_1-C_4)$-alkyl, $(C_1-C_4)$-alkoxy-$(C_1-C_4)$-alkyl, $(C_1-C_4)$-haloalkyl, $(C_1-C_4)$-haloalkoxy, $(C_1-C_4)$-alkylthio, $(C_1-C_4)$-haloalkylthio, cyano, isocyano and nitro, for example o-, m- and p-tolyl, dimethylphenyls, 2-, 3- and 4-chlorophenyl, 2-, 3- and 4-fluorophenyl, 2-, 3- and 4-trifluoromethyl- and -trichloromethylphenyl, 2,4-, 3,5-, 2,5- and 2,3-dichlorophenyl, o-, m- and p-methoxyphenyl.

Optionally substituted cycloalkyl is preferably cycloalkyl, which is unsubstituted or mono- or polysubstituted, preferably up to trisubstituted, by identical or different radicals from the group of halogen, cyano, $(C_1-C_4)$-alkyl, $(C_1-C_4)$-alkoxy, $(C_1-C_4)$-alkoxy-$(C_1-C_4)$-alkoxy, $(C_1-C_4)$-alkoxy-$(C_1-C_4)$-alkyl, $(C_1-C_4)$-haloalkyl and $(C_1-C_4)$-haloalkoxy, especially by one or two $(C_1-C_4)$-alkyl radicals.

Optionally substituted heterocyclyl is preferably heterocyclyl which is unsubstituted or mono- or polysubstituted, preferably up to trisubstituted, by identical or different radicals from the group of halogen, cyano, $(C_1-C_4)$-alkyl, $(C_1-C_4)$-alkoxy, $(C_1-C_4)$-alkoxy-$(C_1-C_4)$-alkoxy, $(C_1-C_4)$-alkoxy-$(C_1-C_4)$-alkyl, $(C_1-C_4)$-haloalkyl, $(C_1-C_4)$-haloalkoxy, nitro and oxo, especially mono- or polysubstituted by radicals from the group of halogen, $(C_1-C_4)$-alkyl, $(C_1-C_4)$-alkoxy, $(C_1-C_4)$-haloalkyl and oxo, most preferably substituted by one or two $(C_1-C_4)$-alkyl radicals.

Examples of alkyl-substituted heteroaryl groups are furylmethyl, thienylmethyl, pyrazolylmethyl, imidazolylmethyl, 1,2,3- and 1,2,4-triazolylmethyl, isoxazolylmethyl, thiazolylmethyl, isothiazolylmethyl, 1,2,3-, 1,3,4-, 1,2,4- and 1,2,5-oxadiazolylmethyl, azepinylmethyl, pyrrolylmethyl, pyridylmethyl, pyridazinylmethyl, pyrimidinylmethyl, pyrazinylmethyl, 1,3,5-, 1,2,4- and 1,2,3-triazinylmethyl, 1,2,4-, 1,3,2-, 1,3,6- and 1,2,6-oxazinylmethyl, oxepinylmethyl, thiepinylmethyl and 1,2,4-diazepinylmethyl.

Salts which are suitable according to the invention of the compounds according to the invention, for example salts with bases or acid addition salts, are all customary non-toxic salts, preferably agriculturally and/or physiologically acceptable salts. For example salts with bases or acid addition salts. Preference is given to salts with inorganic bases such as, for example, alkali metal salts (e.g. sodium, potassium or caesium salts), alkaline earth metal salts (e.g. calcium or magnesium salts), ammonium salts or salts with organic bases, in particular with organic amines, such as, for example, triethylammonium, dicyclohexylammonium, N,N'-dibenzylethylenediammonium, pyridinium, picolinium or ethanolammonium salts, salts with inorganic acids (e.g. hydrochlorides, hydrobromides, dihydrosulphates, trihydrosulphates or phosphates), salts with organic carboxylic acids or organic sulphoacids (e.g. formates, acetates, trifluoroacetates, maleates, tartrates, methanesulphonates, benzenesulphonates or 4-toluenesulphonates). It is known that t-amines such as some of the compounds according to the invention are capable of forming N-oxides, which also represent salts according to the invention.

The compounds according to the invention may, depending on the nature of the substituents, be in the form of geometric and/or optically active isomers or corresponding isomer mixtures in different compositions. These stereoisomers are, for example, enantiomers, diastereomers, atropisomers or geometric isomers. Accordingly, the invention encompasses pure stereoisomers and any mixture of these isomers.

If appropriate, the compounds according to the invention may be present in various polymorphic forms or as mixtures of different polymorphic forms. Both the pure polymorphs and the polymorph mixtures are provided by the invention and can be used according to the invention.

The compounds of the general formula (I) can be mixed or applied jointly with other insecticidal, nematicidal, acaricidal or antimicrobial active compounds. In these mixtures or joint applications, synergistic effects occur, i.e. the observed effect of these mixture or joint applications is higher than the total of the effects of the individual active compounds in these applications. Examples of such mixing or combination partners are:

(1) Acetylcholinesterase (AChE) inhibitors, for example
carbamates, for example alanycarb (II-1-1), aldicarb (II-1-2), bendiocarb (II-1-3), benfuracarb (II-1-4), butocarboxim (II-1-5), butoxycarboxim (II-1-6), carbaryl (II-1-7), carbofuran (II-1-8), carbosulfan (II-1-9), ethiofencarb (II-1-10), fenobucarb (II-1-11), formetanate (II-1-12), furathiocarb (II-1-13), isoprocarb (II-1-14), methiocarb (II-1-15), methomyl (II-1-16), metolcarb (II-1-17), oxamyl (II-1-18), pirimicarb (II-1-19), propoxur (II-1-20), thiodicarb (II-1-21), thiofanox (II-1-22), triazamate (II-1-23), trimethacarb (II-1-24), XMC (II-1-25) and xylylcarb (II-1-26); or
organophosphates, for example acephate (II-1-27), azamethiphos (II-1-28), azinphos-ethyl (II-1-29), azinphos-methyl (II-1-30), cadusafos (II-1-31), chlorethoxyfos (II-1-32), chlorfenvinphos (II-1-33), chlormephos (II-1-34), chlorpyrifos (II-1-35), chlorpyrifos-methyl (II-1-36), coumaphos (II-1-37), cyanophos (II-1-38), demeton-S-methyl (II-1-39), diazinon (II-1-40), dichlorvos/DDVP (II-1-41), dicrotophos (II-1-42), dimethoate (II-1-43), dimethylvinphos (II-1-44), disulfoton (II-1-45), EPN (II-1-46), ethion (II-1-47), ethoprophos (II-1-48), famphur (II-1-49), fenamiphos (II-1-50), fenitrothion (II-1-51), fenthion (II-1-52), fosthiazate (II-1-53), heptenophos (II-1-54), imicyafos (II-1-55), isofenphos (II-1-56), isopropyl O-(methoxyaminothiophosphoryl) salicylate (II-1-57), isoxathion (II-1-58), malathion (II-1-59), mecarbam (II-1-60), methamidophos (II-1-61), methidathion (II-1-62), mevinphos (II-1-63), monocrotophos (II-1-64), naled (II-1-65), omethoate (II-1-66), oxydemeton-methyl (II-1-67), parathion (II-1-68), parathion-methyl (II-1-69), phenthoate (II-1-70), phorate (II-1-71), phosalone (II-1-72), phosmet (II-1-73), phosphamidon (II-1-74), phoxim (II-1-75), pirimiphos-methyl (II-1-76), profenofos (II-1-77), propetamphos (II-1-78), prothiofos (II-1-79), pyraclofos (II-1-80), pyridaphenthion (II-1-81), quinalphos (II-1-82), sulfotep (II-1-83), tebupirimfos (II-1-84), temephos (II-1-85), terbufos (II-1-86), tetrachlorvinphos (II-1-87), thiometon (II-1-88), triazophos (II-1-89), triclorfon (II-1-90) and vamidothion (II-1-91).

(2) GABA-gated chloride channel antagonists such as, for example,
cyclodiene organochlorins, for example chlordane (II-2-1) and endosulfan (II-2-2); or
phenylpyrazoles (fiproles), for example ethiprole (II-2-3) and fipronil (II-2-4).

(3) Sodium channel modulators/voltage-dependent sodium channel blockers such as, for example,
pyrethroids, for example acrinathrin (II-3-1), allethrin (II-3-2), d-cis-trans allethrin (II-3-3), d-trans allethrin (II-3-4), bifenthrin (II-3-5), bioallethrin (II-3-6), bioallethrin S-cyclopentenyl isomer (II-3-7), bioresmethrin (II-3-8), cycloprothrin (II-3-9), cyfluthrin (II-3-10), beta-cyfluthrin (II-3-11), cyhalothrin (II-3-12), lambda-cyhalothrin (II-3-13), gamma-cyhalothrin (II-3-14), cypermethrin (II-3-15), alpha-cypermethrin (II-3-16), beta-cypermethrin (II-3-17), theta-cypermethrin (II-3-18), zeta-cypermethrin (II-3-19), cyphenothrin [(1R)-trans isomers] (II-3-20), deltamethrin (II-3-21), empenthrin [(EZ)-(1R) isomers] (II-3-22), esfenvalerate (II-3-23), etofenprox (II-3-24), fenpropathrin (II-3-25), fenvalerate (II-3-26), flucythrinate (II-3-27), flumethrin (II-3-28), tau-fluvalinate (II-3-29), halfenprox (II-3-30), imiprothrin (II-3-31), kadethrin (II-3-32), permethrin (II-3-33), phenothrin [(1R)-trans isomer] (II-3-34), prallethrin (II-3-35), pyrethrine (pyrethrum) (II-3-36), resmethrin (II-3-37), silafluofen (II-3-38), tefluthrin (II-3-39), tetramethrin (II-3-40), tetramethrin [(1R) isomers)] (II-3-41), tralomethrin (II-3-42) and transfluthrin (II-3-43); or
DDT (II-3-44); or methoxychlor (II-3-45).

(4) Nicotinergic acetylcholine receptor (nAChR) agonists such as, for example,
neonicotinoids, for example acetamiprid (II-4-1), clothianidin (II-4-2), dinotefuran (II-4-3), imidacloprid (II-4-4), nitenpyram (II-4-5), thiacloprid (II-4-6) and thiamethoxam (II-4-7); or
nicotine (II-4-8).

(5) Nicotinergic acetylcholine receptor (nAChR) allosteric activators such as, for example,
spinosyns, for example spinetoram (II-5-1) and spinosad (II-5-2).

(6) Chloride channel activators such as, for example,
avermectins/milbemycins, e.g. abamectin (II-6-1), emamectin benzoate (II-6-2), lepimectin (II-6-3) and milbemectin (II-6-4).

(7) Juvenile hormone imitators such as, for example,
juvenile hormone analogues, for example hydroprene (II-7-1), kinoprene (II-7-2) and methoprene (II-7-3); or
fenoxycarb (II-7-4); or pyriproxyfen (II-7-5).

(8) Active compounds with unknown or nonspecific mechanisms of action such as, for example
alkyl halides, e.g. methyl bromide (II-8-1) and other alkyl halides; or
chloropicrin (II-8-2); or sulphuryl fluoride (II-8-3); or borax (II-8-4); or tartar emetic (II-8-5).

(9) Selective antifeedants, for example pymetrozine (II-9-1); or flonicamid (II-9-2).

(10) Mite growth inhibitors, for example clofentezine (II-10-1), hexythiazox (II-10-2) and diflovidazin (II-10-3); or etoxazole (II-10-4).

(11) Microbial disruptors of the insect gut membrane, for example *Bacillus thuringiensis* subspecies *israelensis* (II-11-1), *Bacillus sphaericus* (II-11-2), *Bacillus thuringiensis* subspecies *aizawai* (II-11-3), *Bacillus thuringiensis* subspecies

*kurstaki* (II-11-4), *Bacillus thuringiensis* subspecies *tenebrionis* (II-11-5) and BT plant proteins: Cry1Ab, Cry1Ac, Cry1Fa, Cry2Ab, mCry3A, Cry3Ab, Cry3Bb, Cry34/35Ab1 (II-11-6).

(12) Oxidative phosphorylation inhibitors, ATP disruptors such as, for example, diafenthiuron (II-12-1); or organo tin compounds, e.g. azocyclotin (II-12-2), cyhexatin (II-12-3) and fenbutatin oxide (II-12-4); or propargite (II-12-5); or tetradifon (II-12-6).

(13) Oxidative phosphorylation decouplers acting by interrupting the H proton gradient such as, for example, chlorfenapyr (II-13-1), DNOC (II-13-2) and sulfluramid (II-13-3).

(14) Nicotinergic acetylcholine receptor antagonists such as, for example, bensultap (II-14-1), cartap hydrochloride (II-14-2), thiocyclam (II-14-3) and thiosultap-sodium (II-14-4).

(15) Chitin biosynthesis inhibitors, type 0, such as, for example, bistrifluron (II-15-1), chlorfluazuron (II-15-2), diflubenzuron (II-15-3), flucycloxuron (II-15-4), flufenoxuron (II-15-5), hexaflumuron (II-15-6), lufenuron (II-15-7), novaluron (II-15-8), noviflumuron (II-15-9), teflubenzuron (II-15-10) and triflumuron (II-15-11).

(16) Chitin biosynthesis inhibitors, type 1, such as, for example, buprofezin (II-16-1).

(17) Moulting disruptors, dipteran such as, for example, cyromazine (II-17-1).

(18) Ecdysone receptor agonists such as, for example, chromafenozide (II-18-1), halofenozide (II-18-2), methoxyfenozide (II-18-3) and tebufenozide (II-18-4).

(19) Octopaminergic agonists such as, for example, amitraz (II-19-1).

(20) Complex-III electron transport inhibitors such as, for example, hydramethylnone (II-20-1); or acequinocyl (II-20-2); or fluacrypyrim (II-20-3).

(21) Complex-I electron transport inhibitors, for example METI acaricides, for example fenazaquin (II-21-1), fenpyroximate (II-21-2), pyrimidifen (II-21-3), pyridaben (II-21-4), tebufenpyrad (II-21-5) and tolfenpyrad (II-21-6); or rotenone (Derris) (II-21-7).

(22) Voltage-dependent sodium channel blockers, for example indoxacarb (II-22-1); or metaflumizone (II-22-2).

(23) Inhibitors of acetyl-CoA carboxylase such as, for example, tetronic and tetramic acid derivatives, for example spirodiclofen (II-23-1), spiromesifen (II-23-2) and spirotetramat (II-23-3).

(24) Complex-IV electron transport inhibitors such as, for example, phosphines, for example aluminium phosphide (II-24-1), calcium phosphide (II-24-2), phosphine (II-24-3) and zinc phosphide (II-24-4); or cyanide (II-24-5).

(25) Complex-II electron transport inhibitors such as, for example, cyenopyrafen (II-25-1).

(28) Ryanodine receptor effectors such as, for example, diamides, for example chlorantraniliprole (II-28-1) and flubendiamide (II-28-2).

Further active compounds with unknown mechanism of action such as, for example, amidoflumet (II-29-1), azadirachtin (II-29-2), benclothiaz (II-29-3), benzoximate (II-29-4), bifenazate (II-29-5), bromopropylate (II-29-6), chinomethionat (II-29-7), cryolite (II-29-8), cyantraniliprole (Cyazypyr) (II-29-9), cyflumetofen (II-29-10), dicofol (II-29-11), diflovidazin (II-29-12), fluensulfone (II-29-13), flufenerim (II-29-14), flufiprole (II-29-15), fluopyram (II-29-16), fufenozide (II-29-17), imidaclothiz (II-29-18), iprodione (II-29-19), pyridalyl (II-29-20), pyrifluquinazon (II-29-21) and iodomethane (II-29-22); furthermore preparations based on *Bacillus firmus* (I-1582, BioNeem, Votivo) (II-29-23) and also the following known active compounds:

3-bromo-N-{2-bromo-4-chloro-6-[(1-cyclopropylethyl)carbamoyl]phenyl}-1-(3-chloropyridin-2-yl)-1H-pyrazole-5-carboxamide (II-29-24) (known from WO2005/077934), 4-{[(6-bromopyrid-3-yl)methyl](2-fluoroethyl)amino}furan-2(5H)-one (II-29-25) (known from WO2007/115644), 4-{[(6-fluoropyrid-3-yl)methyl](2,2-difluoroethyl)amino}furan-2(5H)-one (II-29-26) (known from WO2007/115644), 4-{[(2-chloro-1,3-thiazol-5-yl)methyl](2-fluoroethyl)amino}furan-2(5H)-one (II-29-27) (known from WO2007/115644), 4-{[(6-chloropyrid-3-yl)methyl](2-fluoroethyl)amino}furan-2(5H)-one (II-29-28) (known from WO2007/115644), 4-{[(6-chloropyrid-3-yl)methyl](2,2-difluoroethyl)amino}furan-2(5H)-one (II-29-29) (known from WO2007/115644), 4-{[(6-chloro-5-fluoropyrid-3-yl)methyl](methyl)amino}furan-2(5H)-one (II-29-30) (known from WO2007/115643), 4-{[(5,6-dichloropyrid-3-yl)methyl](2-fluoroethyl)amino}furan-2(5H)-one (II-29-31) (known from WO2007/115646), 4-{[(6-chloro-5-fluoropyrid-3-yl)methyl](cyclopropyl)amino}furan-2(5H)-one (II-29-32) (known from WO2007/115643), 4-{[(6-chloropyrid-3-yl)methyl](cyclopropyl)amino}furan-2(5H)-one (II-29-33) (known from EP-A-0 539 588), 4-{[(6-chloropyrid-3-yl)methyl](methyl)amino}furan-2(5H)-one (II-29-34) (known from EP-A-0 539 588), {[1-(6-chloropyridin-3-yl)ethyl](methyl)oxido-$\lambda^4$-sulphanylidene}cyanamide (II-29-35) (known from WO2007/149134) and diastereomers thereof {[(1R)-1-(6-chloropyridin-3-yl)ethyl](methyl)oxido-$\lambda^4$-sulphanylidene}cyanamide (A) (II-29-36) and {[(1S)-1-(6-chloropyridin-3-yl)ethyl]imethylloxido-$\lambda^4$-sulphanylidene}cyanamide (B) (II-29-37) (likewise known from WO2007/149134) and sulfoxaflor (II-29-38) (also known from WO2007/149134) and diastereomers thereof [(R)-methyl(oxido) {(1R)-1-[6-(trifluoromethyl)pyridin-3-yl]ethyl}-$\lambda^4$-sulphanylidene]cyanamide (A1) (II-29-39) and [(S)-methyl(oxido){(1S)-1-[6-(trifluoromethyl)pyridin-3-yl]ethyl}-$\lambda^4$-sulphanylidene]cyanamide (A2) (II-29-40), designated as diastereomer group A (known from WO 2010/074747, WO 2010/074751), [(R)-methyl(oxido){(1S)-1-[6-(trifluoromethyl)pyridin-3-yl]ethyl}-$\lambda^4$-sulphanylidene]cyanamide (B1) (II-29-41) and [(S)-methyl(oxido) {(1R)-1-[6-(trifluoromethyl)pyridin-3-yl]ethyl}-$\lambda^4$-sulphanylidene]cyanamide (B2) (II-29-42), designated as diastereomer group B (likewise known from WO 2010/074747, WO 2010/074751) and 11-(4-chloro-2,6-dimethylphenyl)-12-hydroxy-1,4-dioxa-9-azadispiro[4.2.4.2]tetradec-11-en-10-one (II-29-43) (known from WO2006/089633), 3-(4'-fluoro-2,4-dimethylbiphenyl-3-yl)-4-hydroxy-8-oxa-1-azaspiro[4.5]dec-3-en-2-one (II-29-44) (known from WO2008/067911), 1-{2-fluoro-4-methyl-5-[(2,2,2-trifluoroethyl)sulphinyl]phenyl}-3-(trifluoromethyl)-1H-1,2,4-triazol-5-amine (II-29-45) (known from WO2006/043635), [(3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H,11H-benzo[f]pyrano[4,3-b]chromen-4-yl]methyl cyclopropanecarboxylate (II-29-46) (known from WO2008/066153), 2-cyano-3-(difluoromethoxy)-N,N-dimethylbenzenesulphonamide (II-29-47) (known from WO2006/056433), 2-cyano-3-(difluoromethoxy)-N-methylbenzenesulphonamide (II-29-48) (known from WO2006/100288), 2-cyano-3-(difluoromethoxy)-N-ethylbenzenesulphonamide (II-29-49) (known from WO2005/035486), 4-(difluoromethoxy)-N-ethyl-N-methyl-1,2-benzothiazol-3-amine 1,1-dioxide (II-29-50) (known from WO2007/057407), N-[1-(2,3-dimethylphenyl)-2-(3,5-dimethylphenyl)ethyl]-4,5-dihydro-1,3-thiazol-2-amine (II-29-51) (known from WO2008/104503), {1'-[(2E)-3-(4-chlorophenyl)prop-2-en-1-yl]-5-fluorospiro[indole-3,4'-piperidin]-1(2H)-yl}(2-chloropyridin-4-yl)methanone (II-29-52) (known from WO2003/106457), 3-(2,5-dimethylphenyl)-4-hydroxy-8-methoxy-1,8-diazaspiro[4.5]dec-3-en-2-one (II-29-53) (known from WO2009/049851), 3-(2,5-dimethylphenyl)-8-methoxy-2-oxo-1,8-diazaspiro[4.5]dec-3-en-4-yl ethyl carbonate (II-29-54) (known from WO2009/049851), 4-(but-2-yn-1-yloxy)-6-(3,5-dimethylpiperidin-1-yl)-5-fluoropyrimidine (II-29-55) (known from WO2004/099160), (2,2,3,3,4,4,5,5-octafluoropentyl)(3,3,3-trifluoropropyl)malononitrile (II-29-56) (known from WO2005/063094), (2,2,3,3,4,4,5,5-octafluoropentyl)(3,3,4,4,4-pentafluorobutyl)malononitrile (II-29-57) (known from WO2005/063094), 8-[2-(cyclopropylmethoxy)-4-(trifluoromethyl)phenoxy]-3-[6-(trifluoromethyl)pyridazin-3-yl]-3-azabicyclo[3.2.1]octane (II-29-58) (known from WO2007/040280), 2-ethyl-7-methoxy-3-methyl-6-[(2,2,3,3-tetrafluoro-2,3-dihydro-1,4-benzodioxin-6-yl)oxy]quinolin-4-yl methylcarbonate (II-29-59) (known from JP2008/110953), 2-ethyl-7-methoxy-3-methyl-6-[(2,2,3,3-tetrafluoro-2,3-dihydro-1,4-benzodioxin-6-yl)oxy]quinolin-4-yl acetate (II-29-60) (known from JP2008/110953), PF1364 (CAS Reg. No. 1204776-60-2) (II-29-61) (known from JP2010/018586), 5-[5-(3,5-dichlorophenyl)-5-(trifluoromethyl)-4,5-dihydro-1,2-oxazol-3-yl]-2-(1H-1,2,4-triazol-1-yl)benzonitrile (II-29-62) (known from WO2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (II-29-63) (known from WO2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (II-29-64) (known from WO2005/085216), 4-{[(6-chloropyridin-3-yl)methyl](cyclopropyl)amino}-1,3-oxazol-2(5H)-one (II-29-65), 4-{[(6-chloropyridin-3-yl)methyl](2,2-difluoroethyl)amino}-1,3-oxazol-2(5H)-one (II-29-66), 4-{[(6-chloropyridin-3-yl)methyl](ethyl)amino}-1,3-oxazol-2(5H)-one (II-29-67), 4-{[(6-chloropyridin-3-yl)methyl](methyl)amino}-1,3-oxazol-2(5H)-one (II-29-68) (all known from WO2010/005692), NNI-0711 (II-29-69) (known from WO2002/096882), 1-acetyl-N-[4-(1,1,1,3,3,3-hexafluoro-2-methoxypropan-2-yl)-3-isobutylphenyl]-N-isobutyryl-3,5-dimethyl-1H-pyrazole-4-carboxamide (II-29-70) (known from WO2002/096882), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (II-29-71) (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (II-29-72) (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (II-29-73) (known from WO2005/085216), methyl 2-[3,5-dibromo-2-({[3-bromo-1-(3-chloropyridin-2-yl)-1H-pyrazol-5-yl]carbonyl}amino)benzoyl]-1,2-diethylhydrazinecarboxylate (II-29-74) (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (II-29-75) (known from WO2005/085216), (5RS,7RS;5RS,7SR)-1-(6-chloro-3-pyridylmethyl)-1,2,3,5,6,7-hexahydro-7-methyl-8-nitro-5-propoxyimidazo[1,2-a]pyridine (II-29-76) (known from WO2007/101369), 2-{6-[2-(5-fluoropyridin-3-yl)-1,3-thiazol-5-yl]pyridin-2-yl}pyrimidine (II-29-77) (known from WO2010/006713), 2-{6-[2-(pyridin-3-yl)-1,3-thiazol-5-yl]pyridin-2-yl}pyrimidine (II-29-78) (known from WO2010/006713), 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide (II-29-79) (known from WO2010/069502), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (II-29-80) (known from WO2010/069502), N-[2-(tert-butylcarbamoyl)-4-cyano-6-methylphenyl]-1-(3-chloropyridin-2-yl)-3-{[5-(trifluoromethyl)-1H-tetrazol-1-yl]methyl}-1H-pyrazole-5-carboxamide (II-29-81) (known from WO2010/069502), N-[2-(tert-butylcarbamoyl)-4-cyano-6-methylphenyl]-1-(3-chloropyridin-2-yl)-3-{[5-(trifluoromethyl)-2H-tetrazol-2-yl]methyl}-1H-pyrazole-5-carboxamide (II-29-82) (known from WO2010/069502) and (1E)-N-[(6-chloropyridin-3-yl)methyl]-N'-cyano-N-(2,2-difluoroethyl)ethanimidamide (II-29-83) (known from WO2008/009360).

Antimicrobially active compounds:

(1) Ergosterol biosynthesis inhibitors, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulphate, imibenconazole, ipconazole, metconazole, myclobutanil, naftifin, nuarimol, oxpoconazole, paclobutrazole, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, uniconazole-p, viniconazole, voriconazole, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethylsilyl)propoxy]phenyl}imidoformamide and O-[1-(4-methoxyphenoxy)-3,3-dimethylbutan-2-yl]-1H-imidazole-1-carbothioate.

(2) Respiration inhibitors (respiratory chain inhibitors), for example bixafen, boscalid, carboxin, diflumetorim, fenfuram, fluopyram, flutolanil, fluxapyroxad, furametpyr, furmecyclox, isopyrazam mixture of the syn-epimeric racemate 1RS,4SR,9RS and of the anti-epimeric racemate 1RS,4SR,9SR, isopyrazam (anti-epimeric racemate), isopyrazam (anti-epimeric enantiomer 1R,4S,9S), isopyrazam (anti-epimeric enantiomer 1S,4R,9R), isopyrazam (syn-epimeric racemate 1RS,4SR,9RS), isopyrazam (syn-epimeric enantiomer 1R,4S,9R), isopyrazam (syn-epimeric enantiomer 1S,4R,9S), mepronil, oxycarboxin, penflufen, penthiopyrad, sedaxane, thifluzamide, 1-methyl-N-[2-(1,1,2,2-tetrafluoroethoxy)phenyl]-3-(trifluoromethyl)-1H-pyrazole-4-carboxamide, 3-(difluoromethyl)-1-methyl-N-[2-(1,1,2,2-tetrafluoroethoxy)phenyl]-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide and N-[1-(2,4-dichlorophenyl)-1-methoxypropan-2-yl]-3-(difluoromethyl)-1-methyl-1H-pyrazole-4-carboxamide, (3) Respiration inhibitors (respiratory chain inhibitors) acting on complex III of the respiratory chain, for example ametoctradin, amisulbrom, azoxystrobin, cyazofamid, dimoxystrobin, enestroburin, famoxadone, fenamidone, fluoxastrobin, kresoxim-methyl, metominostrobin, orysastrobin, picoxystrobin, pyraclostrobin, pyrametostrobin, pyraoxystrobin, pyribencarb, trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(methoxyimino)-N-methyl-2-(2-{[({(1E)-1-[3-(trifluoromethyl)phenyl]ethylidene}amino)oxy]methyl}phenyl)ethanamide, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, methyl (2E)-2-{2-[({cyclopropyl[(4-methoxyphenyl)imino]methyl}sulphanyl)methyl]phenyl}-3-methoxyprop-2-enoate, N-(3-ethyl-3,5,5-trimethylcyclohexyl)-3-(formylamino)-2-hydroxybenzamide, 2-{2-[(2,5-dimethylphenoxy)methyl]phenyl}-2-methoxy-N-methylacetamide and (2R)-2-{2-[(2,5-dimethylphenoxy)methyl]phenyl}-2-methoxy-N-methylacetamide.

(4) Mitosis and cell division inhibitors, for example benomyl, carbendazim, chlorfenazole, diethofencarb, ethaboxam, fluopicolide, fuberidazole, pencycuron, thiabendazole, thiophanate-methyl, thiophanate, zoxamide, 5-chloro-7-(4-methylpiperidin-1-yl)-6-(2,4,6-trifluorophenyl)[1,2,4]triazolo[1,5-a]pyrimidine and 3-chloro-5-(6-chloropyridin-3-yl)-6-methyl-4-(2,4,6-trifluorophenyl)pyridazine.

(5) Compounds with multisite activity, for example Bordeaux mixture, captafol, captan, chlorothalonil, copper preparations such as copper hydroxide, copper naphthenate, copper oxide, copper oxychloride, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulphur and sulphur preparations, for example calcium polysulphide, thiram, tolylfluanid, zineb and ziram.

(6) Resistance inductors, for example acibenzolar-S-methyl, isotianil, probenazole and tiadinil.

(7) Amino acid and protein biosynthesis inhibitors, for example andoprim, blasticidin-S, cyprodinil, kasugamycin, kasugamycin hydrochloride hydrate, mepanipyrim and pyrimethanil, (8) ATP production inhibitors, for example fentin acetate, fentin chloride, fentin hydroxide and silthiofam.

(9) Cell wall synthesis inhibitors, for example benthiavalicarb, dimethomorph, flumorph, iprovalicarb, mandipropamid, polyoxins, polyoxorim, validamycin A and valifenalate.

(10) Lipid and membrane synthesis inhibitors, for example biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene and tolclofos-methyl.

(11) Melanin biosynthesis inhibitors, for example carpropamid, diclocymet, fenoxanil, phthalide, pyroquilon and tricyclazole.

(12) Nucleic acid synthesis inhibitors, for example benalaxyl, benalaxyl-M (kiralaxyl), bupirimate, clozylacon, dimethirimol, ethirimol, furalaxyl, hymexazol, metalaxyl, metalaxyl-M (mefenoxam), ofurace, oxadixyl, oxolinic acid,

(13) Signal transduction inhibitors, for example chlozolinate, fenpiclonil, fludioxonil, iprodione, procymidone, quinoxyfen and vinclozolin.

(14) Decouplers, for example binapacryl, dinocap, ferimzone, fluazinam and meptyldinocap.

(15) Further compounds, for example benthiazole, bethoxazin, capsimycin, carvone, chinomethionat, chlazafenone, cufraneb, cyflufenamid, cymoxanil, cyprosulfamide, dazomet, debacarb, dichlorophen, diclomezine, difenzoquat, difenzoquat methylsulphate, diphenylamine, ecomat, fenpyrazamine, flumetover, fluoromide, flusulfamide, flutianil, fosetyl-aluminium, fosetyl-calcium, fosetyl-sodium, hexachlorobenzene, irumamycin, methasulfocarb, methyl isothiocyanate, metrafenon, mildiomycin, natamycin, nickel dimethyldithiocarbamate, nitrothal-isopropyl, octhilinone, oxamocarb, oxyfenthiin, pentachlorophenol and salts thereof, phenothrin, phosphoric acid and salts thereof, propamocarb-fosetylate, propanosine-sodium, proquinazid, pyrrolnitrin, tebufloquin, tecloftalam, tolnifanid, triazoxide, trichlamide, zarilamide, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-methoxyphenoxy)-3,3-dimethylbutan-2-yl 1H-imidazole-1-carboxylate, 2,3,5,6-tetrachloro-4-(methylsulphonyl)pyridine, 2,3-dibutyl-6-chlorothieno[2,3-d]pyrimidin-4(3H)-one, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, 2-butoxy-6-iodo-3-propyl-4H-chromen-4-one, 2-chloro-5-[2-chloro-1-(2,6-difluoro-4-methoxyphenyl)-4-methyl-1H-imidazol-5-yl]pyridine, 2-phenylphenol and salts thereof, 3,4,5-trichloropyridine-2,6-dicarbonitrile, 3-[5-(4-chlorophenyl)-2,3-dimethyl-1,2-oxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3,4-thiadiazole-2-thiol, 5-chloro-N'-phenyl-N'-(prop-2-yn-1-yl)thiophene-2-sulphonohydrazide, 5-methyl-6-octyl[1,2,4]triazolo[1,5-a]pyrimidine-7-amine, ethyl (2Z)-3-amino-2-cyano-3-phenylprop-2-enoate, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]methyl}-2-phenylacetamide, N-{(Z)-[(cyclopropylmethoxy)imino][6-(difluoromethoxy)-2,3-difluorophenyl]methyl}-2-phenylacetamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4- carboxamide, N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, pentyl {6-[({[(1-methyl-1H-tetrazol-5-yl)(phenyl)methylidene]amino}oxy)methyl]pyridin-2-yl}carbamate, phenazine-1-carboxylic acid, quinolin-8-ol and quinolin-8-ol sulphate (2:1), All mixing components mentioned in classes (1) to (15) can, if they are capable on the basis of their functional groups, optionally form salts with suitable bases or acids.

(16) Further compounds, for example 1-methyl-3-(trifluoromethyl)-N-[2'-(trifluoromethyl)biphenyl-2-yl]-1H-pyrazole-4-carboxamide, N-(4'-chlorobiphenyl-2-yl)-3-(difluoromethyl)-1-methyl-1H-pyrazole-4-carboxamide, N-(2',4'-dichlorobiphenyl-2-yl)-3-(difluoromethyl)-1-methyl-1H-pyrazole-4-carboxamide, 3-(difluoromethyl)-1-methyl-N-[4'-(trifluoromethyl)biphenyl-2-yl]-1H-pyrazole-4-carboxamide, N-(2',5'-difluorobiphenyl-2-yl)-1-methyl-3-(trifluoromethyl)-1H-pyrazole-4-carboxamide, 3-(difluoromethyl)-1-methyl-N-[4'-(prop-1-yn-1-yl)biphenyl-2-yl]-1H-pyrazole-4-carboxamide, 5-fluoro-1,3-dimethyl-N-[4'-(prop-1-yn-1-yl)biphenyl-2-yl]-1H-pyrazole-4-carboxamide, 2-chloro-N-[4'-(prop-1-yn-1-yl)biphenyl-2-yl]pyridine-3-carboxamide, 3-(difluoromethyl)-N-[4'-(3,3-dimethylbut-1-yn-1-yl)biphenyl-2-yl]-1-methyl-1H-pyrazole-4-carboxamide, N-[4'-(3,3-dimethylbut-1-yn-1-yl)biphenyl-2-yl]-5-fluoro-1,3-dimethyl-1H-pyrazole-4-carboxamide, 3-(difluoromethyl)-N-(4'-ethynylbiphenyl-2-yl)-1-methyl-1H-pyrazole-4-carboxamide, N-(4'-ethynylbiphenyl-2-yl)-5-fluoro-1,3-dimethyl-1H-pyrazole-4-carboxamide, 2-chloro-N-(4'-ethynylbiphenyl-2-yl)pyridine-3-carboxamide, 2-chloro-N-[4'-(3,3-dimethylbut-1-yn-1-yl)biphenyl-2-yl]pyridine-3-carboxamide, 4-(difluoromethyl)-2-methyl-N-[4'-(trifluoromethyl)biphenyl-2-yl]-1,3-thiazole-5-carboxamide, 5-fluoro-N-[4'-(3-hydroxy-3-methylbut-1-yn-1-yl)biphenyl-2-yl]-1,3-dimethyl-1H-pyrazole-4-carboxamide, 2-chloro-N-[4'-(3-hydroxy-3-methylbut-1-yn-1-yl)biphenyl-2-yl]pyridine-3-carboxamide, 3-(difluoromethyl)-N-[4'-(3-methoxy-3-methylbut-1-yn-1-yl)biphenyl-2-yl]-1-methyl-1H-pyrazole-4-carboxamide, 5-fluoro-N-[4'-(3-methoxy-3-methylbut-1-yn-1-yl)biphenyl-2-yl]-1,3-dimethyl-1H-pyrazole-4-carboxamide, 2-chloro-N-[4'-(3-methoxy-3-methylbut-1-yn-1-yl)biphenyl-2-yl]pyridine-3-carboxamide, (5-bromo-2-methoxy-4-methylpyridin-3-yl)(2,3,4-trimethoxy-6-methylphenyl)methanone and N-[2-(4-{[3-(4-chlorophenyl)prop-2-yn-1-yl]oxy}-3-methoxyphenyl)ethyl]-N2-(methylsulphonyl)valinamide.

The active compounds identified here by their common names are known and are described, for example, in the pesticide handbook ("The Pesticide Manual" 14th Ed., British Crop Protection Council 2006) or can be found on the Internet (e.g. http://www.alanwood.net/pesticides).

All mixing components mentioned in classes (1) to (16) can, if they are capable on the basis of their functional groups, optionally form salts with suitable bases or acids.

Finally, it has been found that the novel compounds of the formula (I), whilst being well tolerated by plants, with favourable homeotherm toxicity and good environmental compatibility, are suitable in particular for controlling animal pests, especially arthropods, insects, arachnids, helminths, nematodes and molluscs, which are encountered in agriculture, in forests, in the protection of stored products and materials and in the hygiene sector, or in the animal health sector. The compounds according to the invention can likewise be used in the animal health sector, for example for controlling endo- and/or ectoparasites.

The compounds according to the invention can be used as agents for controlling animal pests, preferably as crop protection agents. They are effective against normally sensitive and resistant species and against all or some stages of development.

The compounds according to the invention can be converted into generally known formulations. In general, such formulations comprise from 0.01 to 98% by weight of active compound, preferably from 0.5 to 90% by weight.

The compounds according to the invention can be present in their commercially available formulations and in the use forms, prepared from these formulations, as a mixture with other active compounds or synergists. Synergists are compounds which enhance the action of the active compounds, without any need for the synergist added to be active itself.

The active compound content of the use forms prepared from the commercially available formulations may vary within wide limits. The active compound concentration of the application forms may be from 0.00000001 to 95% by weight of active compound, preferably from 0.00001 to 1% by weight.

The compounds are applied in a customary manner appropriate for the use forms.

The invention can be used to treat all plants and parts of plants. Plants in this context are understood to include all plants and plant populations, such as desired and unwanted wild plants or crop plants (including naturally occurring crop plants). Crop plants may be plants obtainable by conventional breeding and optimization methods or by biotechnological and gene-technological methods, or combinations of these methods, including the transgenic plants and including the plant cultivars protectable or not protectable by plant breeders' rights. Parts of plants shall be understood to mean all above-ground and below-ground parts and organs of plants, such as shoot, leaf, flower and root, examples including leaves, needles, stems, trunks, flowers, fruit bodies, fruits and seeds, and also roots, tubers and rhizomes. The plant parts also include harvested material and vegetative and generative propagation material, for example cuttings, tubers, rhizomes, slips and seed.

The treatment according to the invention of the plants and plant parts with the active compounds is effected directly or by allowing them to act on the surroundings, habitat or storage space thereof by the customary treatment methods, for example by dipping, spraying, evaporating, fogging, scattering, painting on, injecting, and, in the case of propagation material, especially in the case of seeds, also by applying one or more coats.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts" or "parts of plants" or "plant parts" have been explained above.

More preferably, plants of the plant cultivars which are each commercially available or in use are treated in accordance with the invention. Plant cultivars are to be understood as meaning plants having new properties ("traits") and which have been obtained by conventional breeding, by mutagenesis or by recombinant DNA techniques. They may be cultivars, biotypes and genotypes.

In the animal health sector, i.e. in the field of veterinary medicine, the active compounds according to the present invention act against animal parasites, especially ectoparasites or endoparasites. The term "endoparasites" includes especially helminths such as cestodes, nematodes or trematodes, and protozoa such as coccidia. Ectoparasites are typically and preferably arthropods, especially insects such as flies (biting and licking), parasitic fly larvae, lice, hair lice, bird lice, fleas and the like; or acaricides such as ticks, for example hard ticks or soft ticks, or mites such as scab mites, harvest mites, bird mites and the like.

It has also been found that the compounds according to the invention have strong insecticidal action against insects which destroy industrial materials. Industrial materials in the present context are understood to mean inanimate materials, such as preferably plastics, adhesives, sizes, papers and cards, leather, wood, processed wood products and coating compositions.

In addition, the combinations according to the invention can be used as antifouling compositions, alone or in combinations with other active compounds.

The active compounds are also suitable for controlling animal pests in the domestic sector, in the hygiene sector and in the protection of stored products, especially insects, arachnids and mites, which are found in enclosed spaces, for example homes, factory halls, offices, vehicle cabins and the like. They can be used to control these pests alone or in combination with other active compounds and auxiliaries in domestic insecticide products. They are effective against sensitive and resistant species, and against all developmental stages.

Plants are to be understood to mean all plant species, plant cultivars and plant populations such as wanted and unwanted wild plants or crop plants. Crop plants to be treated according to the invention are plants which occur naturally or those which are obtained by conventional breeding and optimization methods or by biotechnological and recombinant methods or by combining the methods mentioned above. The term crop plant does, of course, also include transgenic plants.

Plant cultivars are to be understood as meaning plants having new properties (traits) and which have been obtained by conventional breeding, by mutagenesis or by recombinant DNA techniques or a combination thereof. They can be cultivars, varieties, bio- or genotypes.

Plant parts are understood to mean all parts and organs of plants above and below the ground, such as shoot, leaf, flower and root, in particular leaves, needles, stalks, stems, flowers, fruit bodies, fruits, seeds, roots, tubers and rhizomes. The term plant parts also includes harvested material and vegetative and generative propagation material, for example cuttings, tubers, rhizomes, slips and seeds or seed.

In a preferred embodiment, naturally occurring plant species and plant cultivars, or those obtained by conventional breeding and optimization methods (e.g. crossing or protoplast fusion), and also parts thereof, are treated.

In a further embodiment according to the invention, transgenic plants obtained by genetic engineering methods, if appropriate in combination with conventional methods, and parts thereof are treated.

The treatment method according to the invention is preferably employed for genetically modified organisms such as, for example, plants or plant parts.

Genetically modified plants, so-called transgenic plants, are plants in which a heterologous gene has been stably integrated into the genome.

The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology or RNA interference—RNAi-technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf colour, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect on plants. Accordingly, they are also suitable for mobilizing the defense system of the plant against attack by unwanted phytopathogenic fungi and/or microorganisms and or viruses. This may, if appropriate, be one of the reasons for the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are understood to mean phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants which are furthermore preferably treated according to the invention are resistant against one or more biotic stress factors, i.e. said plants have a better defense against animal and microbial pests, such as against nematodes, insects, mites, phytopathogenic fungi, bacteria, viruses and/or viroids.

In addition to the plants and plant cultivars mentioned above, is also possible to treat those according to the invention which are resistant to one or more abiotic stress factors.

Abiotic stress conditions may include, for example, drought, cold temperature exposure, heat exposure, osmotic stress, waterlogging, increased soil salinity, increased exposure to minerals, exposure to ozone, exposure to strong light, limited availability of nitrogen nutrients, limited availability of phosphorus nutrients or shade avoidance.

Plants and plant varieties which may also be treated according to the invention are those plants characterized by enhanced yield characteristics. Enhanced yield in these plants may be the result of, for example, improved plant physiology, improved plant growth and development, such as water use efficiency, water retention efficiency, improved nitrogen use, enhanced carbon assimilation, improved photosynthesis, increased germination efficiency and accelerated maturation. Yield can also be affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stresses. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in maize) be produced by detasseling, (i.e. the mechanical removal of the male reproductive organs or male flowers) but, more typically, male sterility is the result of genetic determinants in the plant genome. In that case, and especially when seed is the desired product to be harvested from the hybrid plants it is typically useful to ensure that male fertility in the hybrid plants which contain the genetic determinants responsible for male sterility is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species. However, genetic determinants for male sterility can also be located in the nuclear genome. Male-sterile plants can also be obtained by plant biotechnology methods such as genetic engineering. A particularly useful means of obtaining male-sterile plants is described in WO 89/10396, in which, for example, a ribonuclease such as a barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp., the genes encoding a petunia EPSPS, a tomato EPSPS, or an *Eleusine* EPSPS. It can also be a mutated EPSPS. Glyphosate-tolerant plants can also be obtained by expressing a gene that encodes a glyphosate oxido-reductase enzyme. Glyphosate-tolerant plants can also be obtained by expressing a gene that encodes a glyphosate acetyl transferase enzyme. Glyphosate-tolerant plants can also be obtained by selecting plants containing naturally-occurring mutations of the above-mentioned genes.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is an enzyme encoding a phosphinothricin acetyltransferase (such as the bar or pat protein from *Streptomyces* species). Plants expressing an exogenous phosphinothricin acetyltransferase have been described.

Further herbicide-tolerant plants are also plants that have been made tolerant to the herbicides inhibiting the enzyme hydroxyphenylpyruvate dioxygenase (HPPD). Hydroxyphenylpyruvate dioxygenases are enzymes that catalyze the reaction in which para-hydroxyphenylpyruvate (HPP) is converted to homogentisate. Plants tolerant to HPPD inhibitors can be transformed with a gene encoding a naturally-occurring resistant HPPD enzyme, or a gene encoding a mutated HPPD enzyme. Tolerance to HPPD inhibitors can also be obtained by transforming plants with genes encoding certain enzymes enabling the formation of homogentisate despite the inhibition of the native HPPD enzyme by the HPPD inhibitor. Tolerance of plants to HPPD inhibitors can also be improved by transforming plants with a gene encoding an enzyme prephenate deshydrogenase in addition to a gene encoding an HPPD-tolerant enzyme.

Still further herbicide resistant plants are plants that are made tolerant to acetolactate synthase (ALS) inhibitors. Known ALS inhibitors include, for example, sulphonylurea, imidazolinone, triazolopyrimidines, pyrimidinyoxy(thio) benzoates, and/or sulphonylaminocarbonyltriazolinone herbicides. Different mutations in the ALS enzyme (also known as acetohydroxyacid synthase, AHAS) are known to confer tolerance to different herbicides and groups of herbicides. The production of sulphonylurea-tolerant plants and imidazolinone-tolerant plants has been described in the international publication WO 1996/033270. Further sulphonylurea- and imidazolinone-tolerant plants have also been described, for example in WO 2007/024782.

Other plants tolerant to imidazolinone and/or sulphonylurea can be obtained by induced mutagenesis, selection in cell cultures in the presence of the herbicide or mutation breeding.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins described online at: http://www.lifesci.sussex.ac.uk/Home/Neil_Crickmore/Bt/, or insecticidal portions thereof, e.g., proteins of the Cry protein classes Cry1Ab, Cry1Ac, Cry1F, Cry2Ab, Cry3Ae, or Cry3Bb or insecticidal portions thereof; or
2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins; or
3) a hybrid insecticidal protein comprising parts of two different insecticidal crystal proteins from *Bacillus thuringiensis*, such as a hybrid of the proteins of 1) above or a hybrid of the proteins of 2) above, e.g., the Cry1A.105 protein produced by maize event MON89034 (WO 2007/027777); or
4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes induced into the encoding DNA during cloning or transformation, such as the Cry3Bb1 protein in maize events MON863 or MON88017, or the Cry3A protein in maize event MIR604; or
5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/Home/Neil_Crickmore/Bt/vip.html, for example proteins from the VIP3Aa protein class; or
6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins;
7) a hybrid insecticidal protein comprising parts from different secreted proteins from *Bacillus thuringiensis* oder *Bacillus cereus*, such as a hybrid of the proteins in 1) above or a hybrid of the proteins in 2) above; or
8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes induced into the encoding DNA during cloning or transformation (while still encoding an insecticidal protein), such as the VIP3Aa protein in cotton event COT102.

Of course, an insect-resistant transgenic plant, as used herein, also includes any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected, or to delay insect resistance development to the plants by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:
a. plants which contain a transgene capable of reducing the expression and/or the activity of the poly(ADP-ribose) polymerase (PARP) gene in the plant cells or plants;
b. plants which contain a stress tolerance enhancing transgene capable of reducing the expression and/or the activity of the PARG encoding genes of the plants or plants cells;
c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant varieties (obtained by plant biotechnology methods such as genetic engineering) which may also be treated according to the invention show altered quantity, quality and/or storage stability of the harvested product and/or altered properties of specific ingredients of the harvested product such as, for example:
1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications.
2) transgenic plants which synthesize non starch carbohydrate polymers or which synthesize non starch carbohydrate polymers with altered properties in comparison to wild type plants without genetic modification. Examples are plants which produce polyfructose, especially of the inulin and levan type, plants which produce alpha-1,4-glucans, plants which produce alpha-1,6-branched alpha-1,4-glucans, and plants producing alternan.
3) Transgenic plants which produce hyaluronan.

Plants or plant cultivars (obtained by plant biotechnology methods such as genetic engineering) which may also be treated according to the invention are plants, such as cotton plants, with altered fibre characteristics. Such plants can be obtained by genetic transformation, or by selection of plants containing a mutation imparting such altered fibre characteristics and include:
a) plants, such as cotton plants, containing an altered form of cellulose synthase genes;
b) plants, such as cotton plants, containing an altered form of rsw2 or rsw3 homologous nucleic acids;
c) plants, such as cotton plants, with increased expression of sucrose phosphate synthase;
d) plants, such as cotton plants, with increased expression of sucrose synthase;
e) plants, such as cotton plants, wherein the timing of the plasmodesmatal gating at the basis of the fibre cell is altered, for example through downregulation of fibre-selective β-1,3-glucanase;
f) plants, such as cotton plants, having fibres with altered reactivity, e.g. through the expression of N-acetylglucosaminetransferase gene including nodC and chitin synthase genes.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants containing a mutation imparting such altered oil profile characteristics and include:
a) plants, such as oilseed rape plants, which produce oil having a high oleic acid content;

b) plants, such as oilseed rape plants, which produce oil having a low linolenic acid content;

c) plants, such as oilseed rape plants, producing oil having a low level of saturated fatty acids.

Particularly useful transgenic plants which may be treated according to the invention are plants which comprise one or more genes which encode one or more toxins, and are the transgenic plants which are sold under the following trade names: YIELD GARD® (for example maize, cotton, soya beans), KnockOut® (for example maize), BiteGard® (for example maize), BT-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which should be mentioned are maize varieties, cotton varieties and soya bean varieties which are available under the following trade names: Roundup Ready® (tolerance to glyphosate, for example maize, cotton, soya beans), Liberty Link® (tolerance to phosphinothricin, for example oilseed rape), IMI® (tolerance to imidazolinone) and SCS® (tolerance to sulphonylurea, for example maize). Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or a combination of transformation events, and that are listed for example in the databases for various national or regional regulatory agencies (see for example http://gmoinfo.jrc.it/gmp_browse.aspx and http://www.agbios.com/dbase.php).

Treatment according to the invention of the plants and plant parts with the active compound combinations is carried out directly or by allowing the compounds to act on their surroundings, environment or storage space by the customary treatment methods, for example by immersion, spraying, evaporation, fogging, scattering, painting on and, in the case of propagation material, in particular in the case of seeds, also by applying one or more coats.

The mixtures according to the invention are particularly suitable for the treatment of seed. Here, particular mention may be made of the combinations according to the invention mentioned above as preferred or particularly preferred. Thus, most of the damage to crop plants which is caused by pests occurs as early as when the seed is infested during storage and after the seed is introduced into the soil, and during and immediately after germination of the plants. This phase is particularly critical since the roots and shoots of the growing plant are particularly sensitive and even minor damage can lead to the death of the whole plant. Protecting the seed and the germinating plant by the use of suitable compositions is therefore of particularly great interest.

The control of pests by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with the additional application of crop protection compositions after sowing or after emergence of the plants. It is furthermore desirable to optimize the amount of active compound employed in such a way as to provide optimum protection for the seed and the germinating plant from attack by pests, but without damaging the plant itself by the active compound employed. In particular, methods for the treatment of seed should also take into consideration the intrinsic insecticidal properties of transgenic plants in order to achieve optimum protection of the seed and the germinating plant with a minimum of crop protection compositions being employed.

The present invention therefore in particular also relates to a method for the protection of seed and germinating plants, from attack by pests, by treating the seed with a composition according to the invention. The invention likewise relates to the use of the compositions according to the invention for the treatment of seed for protecting the seed and the resulting plant from pests. The invention further relates to seed which has been treated with a composition according to the invention for protection from pests.

One of the advantages of the present invention is that the particular systemic properties of the compositions according to the invention mean that treatment of the seed with these compositions not only protects the seed itself, but also the resulting plants after emergence, from pests. In this way, the immediate treatment of the crop at the time of sowing or shortly thereafter can be dispensed with.

A further advantage is the synergistically increased insecticidal activity of the compositions according to the invention in comparison with the individual insecticidally active compound, which exceeds the expected activity of the two active compounds when applied individually. Also advantageous is the synergictic enhancement of the fungicidal activity of the compositions according to the invention compared with the individual fungicidally active compound, which exceeds the expected activity of the active compound applied individually. This makes possible an optimization of the amount of active compounds employed.

Furthermore, it must be considered as advantageous that the mixtures according to the invention can also be employed in particular in transgenic seed, the plants arising from this seed being capable of expressing a protein directed against pests. By treating such seed with the compositions according to the invention, certain pests can be controlled merely by the expression of the, for example, insecticidal protein, and additionally damage to the seed may be averted by the compositions according to the invention.

The compositions according to the invention are suitable for protecting seed of any plant variety as already mentioned above which is employed in agriculture, in the greenhouse, in forests or in horticulture. In particular, this takes the form of seed of maize, peanut, canola, oilseed rape, poppy, soya beans, cotton, beet (for example sugar beet and fodder beet), rice, millet, wheat, barley, oats, rye, sunflower, tobacco, potatoes or vegetables (for example tomatoes, cabbage species). The compositions according to the invention are likewise suitable for treating the seed of fruit plants and vegetables as already mentioned above. The treatment of the seed of maize, soya beans, cotton, wheat and canola or oilseed rape is of particular importance.

As already mentioned above, the treatment of transgenic seed with a composition according to the invention is also of particular significance. This takes the form of seed of plants which, as a rule, comprise at least one heterologous gene which governs the expression of a polypeptide with in particular insecticidal properties. In this context, the heterologous genes in transgenic seed may be derived from microorganisms such as *Bacillus, Rhizobium, Pseudomonas, Serratia, Trichoderma, Clavibacter, Glomus* or *Gliocladium*. The present invention is particularly suitable for the treatment of transgenic seed which comprises at least one heterologous gene originating from *Bacillus* sp. and whose gene product shows activity against the European corn borer and/or the corn root worm. The gene involved is more preferably a heterologous gene which originates from *Bacillus thuringiensis*.

Within the context of the present invention, the composition according to the invention is applied to the seed either alone or in a suitable formulation. Preferably, the seed is treated in a state in which it is stable enough to avoid damage during treatment. In general, the seed may be treated at any point in time between harvest and sowing. The seed usually used has been separated from the plant and freed from cobs, shells, stalks, coats, hairs or the flesh of the fruits.

When treating the seed, it generally has to be ensured that the amount of the composition according to the invention applied to the seed and/or the amount of further additives is selected such that the germination of the seed is not impaired, or that the resulting plant is not damaged. This must be ensured particularly in the case of active compounds which can exhibit phytotoxic effects at certain application rates.

In addition, the compounds according to the invention can be used to control a multitude of different pests, including, for example, harmful sucking insects, biting insects and other pests which are plant parasites, stored material pests, pests which destroy industrial material, and hygiene pests including parasites in the animal health sector, and for the control thereof, for example the elimination and eradication thereof. The present invention thus also includes a method for controlling pests.

In the animal health sector, i.e. in the field of veterinary medicine, the active compounds according to the present invention act against animal parasites, especially ectoparasites or endoparasites. The term "endoparasites" includes especially helminths such as cestodes, nematodes or trematodes, and protozoa such as coccidia. Ectoparasites are typically and preferably arthropods, especially insects such as flies (biting and licking), parasitic fly larvae, lice, hair lice, bird lice, fleas and the like; or acaricides such as ticks, for example hard ticks or soft ticks, or mites such as scab mites, harvest mites, bird mites and the like.

These parasites include:

From the order of the Anoplurida, for example, *Haematopinus* spp., *Linognathus* spp., *Pediculus* spp., *Phthirus* spp. and *Solenopotes* spp.; specific examples are: *Linognathus setosus, Linognathus vituli, Linognathus ovillus, Linognathus oviformis, Linognathus pedalis, Linognathus stenopsis, Haematopinus asini macrocephalus, Haematopinus eurysternus, Haematopinus suis, Pediculus humanus capitis, Pediculus humanus corporis, Phylloera vastatrix, Phthirus pubis, Solenopotes capillatus;*

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.; specific examples are: *Bovicola bovis, Bovicola ovis, Bovicola limbata, Damalina bovis, Trichodectes canis, Felicola subrostratus, Bovicola caprae, Lepikentron ovis, Werneckiella equi;*

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; specific examples are: *Aedes aegypti, Aedes albopictus, Aedes taeniorhynchus, Anopheles gambiae, Anopheles maculipennis, Calliphora erythrocephala, Chrysozona pluvialis, Culex quinquefasciatus, Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorroidalis, Gasterophilus inermis, Gasterophilus nasalis, Gasterophilus nigricornis, Gasterophilus pecorum, Braula coeca;*

From the order of the Siphonapterida, for example *Pulex* spp., *Ctenocephalides* spp., *Tunga* spp., *Xenopsylla* spp., *Ceratophyllus* spp.; specific examples are: *Ctenocephalides canis, Ctenocephalides felis, Pulex irritans, Tunga penetrans, Xenopsylla cheopis;*

From the order of the Heteropterida, for example, *Cimex* spp., *Triatoma* spp., *Rhodnius* spp. and *Panstrongylus* spp.

From the order of the Blattarida, for example *Blatta orientalis, Periplaneta americana, Blattela germanica* and *Supella* spp. (e.g. *Suppella longipalpa*);

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Rhipicephalus* (*Boophilus*) spp., *Dermacentor* spp., *Haemophysalis* spp., *Hyalomma* spp., *Dermanyssus* spp., *Rhipicephalus* spp. (the original genus of multihost ticks), *Ornithonyssus* spp., *Pneumonyssus* spp., *Raillietia* spp., *Pneumonyssus* spp., *Sternostoma* spp., *Varroa* spp., *Acarapis* spp.; specific examples are: *Argas persicus, Argas reflexus, Ornithodorus moubata, Otobius megnini, Rhipicephalus* (*Boophilus*) *microplus, Rhipicephalus* (*Boophilus*) *decoloratus, Rhipicephalus* (*Boophilus*) *annulatus, Rhipicephalus* (*Boophilus*) *calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroa jacobsoni;*

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp.,

*Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.; specific examples are: *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschongastia xerothermobia, Trombicula akamushi, Otodectes cynotis, Notoedres cati, Sarcoptis canis, Sarcoptes bovis, Sarcoptes ovis, Sarcoptes rupicaprae* (=*S. caprae*), *Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi.*

The active compounds according to the invention are also suitable for controlling arthropods, helminths and protozoa which attack animals. The animals include agricultural livestock, for example cattle, sheep, goats, horses, pigs, donkeys, camels, buffalo, rabbits, chickens, turkeys, ducks, geese, cultured fish, honey bees. The animals also include domestic animals—also referred to as companion animals—for example dogs, cats, caged birds, aquarium fish, and what are known as test animals, for example hamsters, guinea pigs, rats and mice.

The control of these arthropods, helminths and/or protozoa should reduce cases of death and improve the performance (for meat, milk, wool, hides, eggs, honey etc.) and the health of the host animal, and so the use of the active compounds according to the invention enables more economically viable and easier animal husbandry.

For example, it is desirable to prevent or to interrupt the uptake of blood from the host by the parasites (if relevant). Control of the parasites can also contribute to preventing the transmission of infectious substances.

The term "control" as used herein with regard to the field of animal health means that the active compounds act by reducing the occurrence of the parasite in question in an animal infested with such parasites to a harmless level. More specifically, "control" as used herein means that the active compound kills the parasite in question, retards its growth or inhibits its proliferation.

In general, the active compounds according to the invention can be employed directly when they are used for the treatment of animals. They are preferably employed in the form of pharmaceutical compositions which may comprise the pharmaceutically acceptable excipients and/or auxiliaries known in the prior art.

In the sector of animal health and in animal husbandry, the active compounds are employed (administered) in a known manner, by enteral administration in the form of, for example, tablets, capsules, potions, drenches, granules, pastes, boluses, the feed-through process and suppositories, by parenteral administration, for example by injection (intramuscular, subcutaneous, intravenous, intraperitoneal inter alia), implants, by nasal administration, by dermal administration in the form, for example, of dipping or bathing, spraying, pouring on and spotting on, washing and powdering, and also with the aid of moulded articles containing the active compound, such as collars, earmarks, tailmarks, limb bands, halters, marking devices, etc. The active compounds can be formulated as a shampoo or as suitable formulations applicable in aerosols or unpressurized sprays, for example pump sprays and atomizer sprays, In the case of employment for livestock, poultry, domestic pets, etc., the active compounds according to the invention can be employed as formulations (for example powders, wettable powders ["WP"], emulsions, emulsifiable concentrates ["EC"], free-flowing compositions, homogeneous solutions and suspension concentrates ["SC"]), which contain the active compounds in an amount of 1 to 80% by weight, directly or after dilution (e.g. 100- to 10 000-fold dilution), or they can be used as a chemical bath.

In the case of use in the animal health sector, the active compounds according to the invention can be used in combination with suitable synergists or other active compounds, for example acaricides, insecticides, anthelmintics, anti-protozoal agents.

The compounds according to the invention can be prepared by customary methods known to those skilled in the art.

Reaction Scheme 1 shows the general Preparation Process A for the compounds (I) according to the invention.

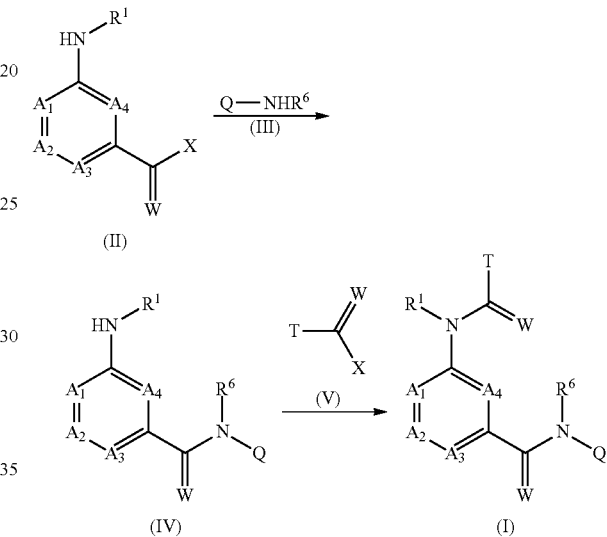

Reaction Scheme 1

The radicals $A_1$-$A_4$, Q, W, $R^1$ and $R^6$ have the meanings described above. T represents the grouping

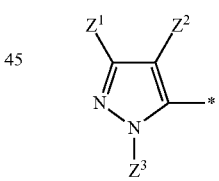

where the radicals $Z^1$, $Z^2$ and $Z^3$ have the meaning given above and the asterisk represents the point of attachment to the grouping C=W. X is any leaving group.

Compounds according to the invention of type (I) can be prepared by reacting amines of the general structure (IV) with activated carboxylic acid derivatives of the general structure (V). The reaction can be carried out in the presence or absence of a solvent. In this step, it is also possible to employ a suitable base.

In general, it is advantageous to carry out the first reaction step of Preparation Process A according to the invention, if appropriate, in the presence of a suitable diluent and, if appropriate, in the presence of a suitable basic reaction auxiliary.

Diluents are advantageously employed in such an amount that the reaction mixture remains readily stirrable during the entire process.

Suitable for use as solvent are any solvents which do not interfere with the reaction such as, for example, water. Suitable are aromatic hydrocarbons such as benzene or toluene; halogenated hydrocarbons such as dichloromethane, chloroform or carbon tetrachloride, open-chain or cyclic ethers such as diethyl ether, dioxane, tetrahydrofuran or 1,2-dimethoxyethane; esters such as ethyl acetate and butyl acetate; ketones such as, for example, acetone, methyl isobutyl ketone and cyclohexanone; amides such as dimethylformamide and dimethylacetamide; nitriles such as acetonitrile; and other inert solvents such as 1,3-dimethyl-2-imidazolidinone; the solvents can be employed on their own or in a combination of two or more solvents.

The base used can be an organic base such as triethylamine, ethyldiisopropylamine, tri-n-butylamine, pyridine and 4-dimethylaminopyridine; furthermore, it is possible to use, for example, the following bases: alkali metal hydroxides such as, for example, sodium hydroxide and potassium hydroxide; carbonates such as sodium bicarbonate and potassium carbonate; phosphates such as dipotassium hydrogenphosphate and trisodium phosphate; alkali metal hydrides such as sodium hydride; alkali metal alkoxides such as sodium methoxide and sodium ethoxide. These bases can be employed in ratios of from 0.01 to 5.0 molar equivalents based on (IV) and (V). Furthermore, it is also possible to use silver(I) cyanide as base and activator [Journal of Organic Chemistry. 1992, 57, 4394-4400; Journal of Medicinal Chemistry 1992, 35, 3905-3918; Journal of Organic Chemistry 2003, 68, 1843-1851]

The suitable reaction temperature is in the range from −20° C. to the boiling point of the solvent in question and the reaction time is from a few minutes to 96 hours, depending on the chosen reactants, solvents and reaction temperature.

Cyclic carbonyl halides as represented by the general structure (V) can be prepared in a simple manner by reacting a heterocyclic carboxylic acid with halogenating agents such as thionyl chloride, thionyl bromide, phosphoryl chloride, oxalyl chloride, phosphorus trichloride, etc. [Houben-Weyl, 1952, Vol. VIII, p. 463 ff.].

However, the preparation of carboxamides represented by formula (I) can also be carried out using coupling reagents such as dicyclohexylcarbodiimide and additives such as 1-hydroxybenzotriazole [Chem. Ber. 1970, 788]. It is also possible to use coupling reagents such as 1-ethyl-3-(3-dimethylaminopropyl)carbodiimide, 1,1'-carbonyl-1H-imidazole and similar compounds.

The coupling reagents used to perform the preparation process are all which are suitable for forming an ester or amide bond (cf. for example, Bodansky et al., Peptide Synthesis, 2nd ed., Wiley & Sons, New York, 1976; Gross, Meienhofer, The Peptide: Analysis, Synthesis, Biology, Academic Press, New York, 1979).

Furthermore, it is also possible to use mixed anhydrides for preparing (I) [J. Am. Chem. Soc 1967, 5012]. In this process, it is possible to use various chloroformic esters, for example isobutyl chloroformate, isopropyl chloroformate. It is likewise possible for this purpose to use diethylacetyl chloride, trimethylacetyl chloride and the like.

Compounds of the general structure (IV) can be prepared by reacting an amine of the general structure (III) with activated carboxylic acid derivatives of the general structure (II). Here, the same conditions as in the preparation of (I) described above apply with respect to the choice of solvent, reaction conditions, reaction time and reagents.

Reaction Scheme 2 shows the general Preparation Process B for the synthesis of the compounds (I) according to the invention.

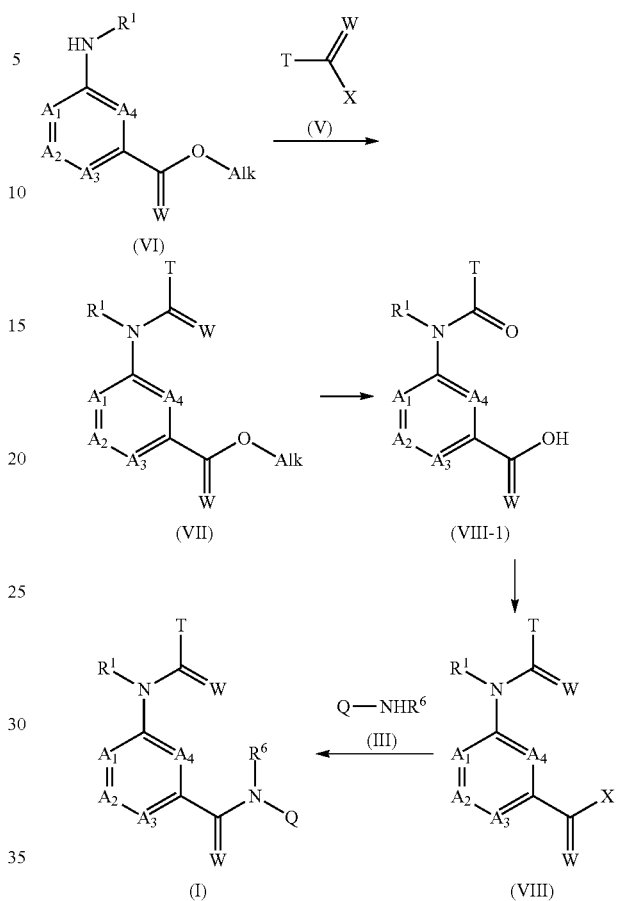

Reaction Scheme 2

The radicals $A_1$-$A_4$, Q, $R^1$, $R^6$ and W have the meanings described above. X represents any leaving group and Alk represents an alkyl radical such as, for example, methyl or ethyl. T represents the grouping

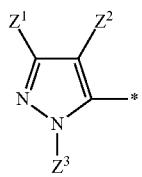

where the radicals $Z^1$, $Z^2$ and $Z^3$ have the meaning given above and the asterisk represents the point of attachment to the grouping C═W.

Compounds according to the invention of type (I) can be prepared by reacting an amine of the general structure (III) with activated carboxylic acid derivatives of the general structure (VIII). Here, the same conditions as in the conversion of (IV) and (V) into (I) described in Preparation Process A apply with respect to the choice of solvent, reaction conditions, reaction time and reagents.

Activated carboxylic acid derivatives of the general structure (VIII) can be prepared by a two-step synthesis from the corresponding carboxylic esters of the general structure (VII). In the first step, the carboxylic acid function, protected in the form of an ester (O-Alk), of the compound (VII) is, depending on the alkyl ester used, deprotected with a suitable reagent [Greene's protective groups in organic synthesis, 4. Edition, P. G. M. Wuts, T. W. Greene, John Wiley & Sons, Inc., Hoboken, N.J.], and the resulting free hydroxyl group of the acid function of (VIII-1) is converted into a leaving group X. Here, the same processes as already described for the preparation of (V) may be employed. Compounds of the general structure (VII) can be prepared by reacting amines of the general structure (VI) with activated carboxylic acid derivatives of the general structure (V). Here, the same conditions as in the synthesis of (I) described in Preparation Process A apply with respect to the choice of solvent, reaction conditions, reaction time and reagents.

Reaction Scheme 3 shows the general Preparation Process C for the synthesis of the compounds (I) according to the invention.

3856-3871; Journal of the American Chemical Society 2006, 128(14), 4586-4587; Chemical Communications (Cambridge, United Kingdom) 2010, 46(8), 1269-1271; WO2009/027393|R1=optionally subst. alkenyl: Organic Chemistry: An Indian Journal 2010, 6(1), 52-55; European Journal of Organic Chemistry 2009, (1), 72-84; WO2006/067444; WO2005/049585].

Reaction Scheme 4 shows the general Preparation Process D for the synthesis of the compounds (I) according to the invention.

Reaction Scheme 3

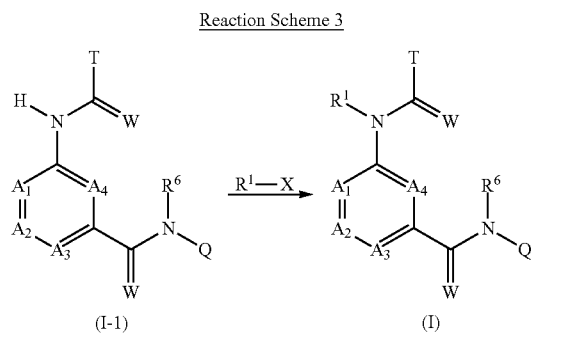

(I-1)  (I)

The radicals $A_1$-$A_4$, Q, $R^6$ and W have the meanings described above. X represents any leaving group such as, for example, chlorine, bromine or iodine. T represents the grouping

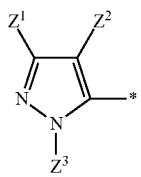

where the radicals $Z^1$, $Z^2$ and $Z^3$ have the meaning given above and the asterisk represents the point of attachment to the grouping C=W. $R^1$ represents the radicals described above except for hydrogen. The compounds of the general structure (I) where R1≠H can be prepared from compounds of the general structure (I-1). Here, use may be made of processes known from the literature [R1=optionally subst. alkyl & (het)arylalkyl: WO2008/061688; Journal of Heterocyclic Chemistry 1995, 32(3), 835-839; WO2011/029808; WO2010/020432; US2010/0152192; WO2010/101949; WO2010/043377, Medicinal Chemistry Letters 2011, 2(8), 632-637; Journal of Heterocyclic Chemistry 1977, 14(7), 1263-1265; WO2011/020193; WO2008/121602; WO2006/074924; WO2006/065794|R1=optionally subst. alkylcarbony & (het)aryl(alkyl)carbonyl: WO2010/015545; Journal of the Chemical Society, Perkin Transactions 1 2002, (2), 257-274; U.S. Pat. No. 7,951,828|R1=optionally subst. alkoxycarbonyl & (het)aryl(alkyl)oxycarbonyl: WO2011/112731; WO2009/027393; Journal of Organic Chemistry 2011, 76(8), 2502-2520|R1=optionally subst. alkynyl: Synthesis 2007, (18), 2920-2923; Tetrahedron 2006, 62(16), Reaction Scheme 4

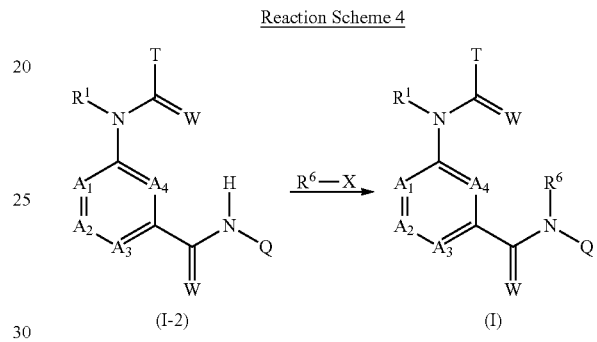

(I-2)  (I)

The radicals $A_1$-$A_4$, Q, $R^1$ and W have the meanings described above. X represents any leaving group such as, for example, chlorine, bromine or iodine. T represents the grouping

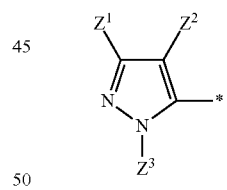

where the radicals $Z^1$, $Z^2$ and $Z^3$ have the meaning given above and the asterisk represents the point of attachment to the grouping C=W. $R^6$ represents the radicals described above.

The compounds of the general structure (I) can be prepared from compounds of the general structure (1-1). Here, use may be made of the processes mentioned for Preparation Process C.

Compounds of the general formulae (II-1), (II-1-1) and (II-2) can be used as precursors for the substances of the general formula (II). Substances of the general formula (II-1-1) are generally known compounds of organic chemistry which can be obtained by established synthesis processes. Possible synthesis routes for the cyclic aminocarboxylic acids of the general formula (II-1-1) are shown in Reaction Scheme 5.

Reaction Scheme 5

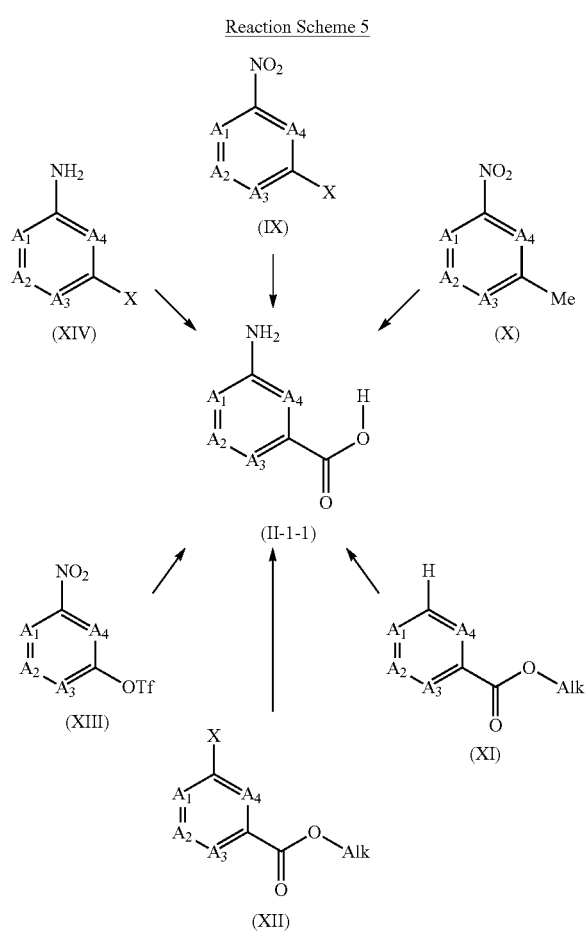

Halogenated (hetero)aromatic nitro- or amino compounds, for example, as represented by the formulae (IX) and (XIV) may serve as starting materials for preparing aminocarboxylic acids of the general structure (II-1-1). Here, the leaving group X is replaced by a cyano group, and the latter is then subjected to acidic or basic hydrolysis. The halogen/cyano exchange can be effected, for example, by nucleophilic substitution at the aromatic ring using a cyanide species such as, for example, sodium cyanide [U.S. Pat. No. 4,766,219], or else by a copper-mediated reaction [Journal of Antibiotics 1994, 47(12), 1456-65].

In the case of the nitro compounds (IX, X, and XIII), the nitro function may subsequently be reduced to an amino function. Suitable processes for such reductions are hydrogenations and metal-mediated reactions such as, for example, tin(II) chloride, iron powder, zinc powder and compounds similar to these.

Hydrogenations can be carried out in a suitable solvent in the presence of a catalyst under an atmosphere of hydrogen (standard pressure or elevated pressure). Suitable for use as catalysts are palladium catalysts such as, for example, palladium on carbon, nickel catalysts such as Raney nickel, cobalt catalysts, ruthenium catalysts, rhodium catalysts, platinum catalysts and compounds similar to these. Suitable solvents are water, alcohols such as methanol and ethanol, aromatic hydrocarbons such as benzene and toluene, open-chain or cyclic ethers such as diethyl ether, dioxane and tetrahydrofuran, and also esters such as ethyl acetate. The reductions can be carried out in a pressure range of from 1 bar to 100 bar, where the temperature may vary between −20° C. and the boiling point of the solvent used. Depending on the reaction conditions, the reaction times are between a few minutes and 96 hours.

The metal-mediated reductions, for example with tin(II) chloride, can be carried out according to a process described in Organic Syntheses Coll. Vol. (III), 453.

Furthermore, (hetero)aromatic aminocarboxylic acids of the general structure (II-1-1) can also be prepared from the corresponding methyl precursors of type (X) by oxidation. Oxidizing agents suitable for such oxidations are, for example, potassium permanganate, sodium dichromate, chromium trioxide and compounds similar to these [Tetrahedron Letters 1995, 36(25), 4369-72; Bioorganic & Medicinal Chemistry Letters 2007, 17(4), 1043-1046]. It is also possible to employ enzymatic processes for such oxidations [PCT Int. Appl., 9502061]. The reduction of the nitro function subsequently required can be carried out analogously to the process described above.

A further method for preparing (hetero)aromatic aminocarboxylic acids of the general structure (II-1-1) is the nitration of carboxylic acid precursors represented by formula (XI) or (XII) and the subsequent reduction of the nitro function. The nitrations can be carried out using processes known from the literature [Justus Liebigs Annalen der Chemie 1958, 611, 194-205; Organikum, Wiley-VCH, 22. Edition, 358ff]. The reduction of the nitro function subsequently required can be carried out analogously to the process described above.

Furthermore, (hetero)aromatic aminocarboxylic acids of the general structure (II-1-1) can be prepared from the corresponding (hetero)aryl triflates of type (XIII) using a palladium-catalyzed process [Synthesis 2006, (4), 594-596].

Compounds of the general formula (II-1) can be prepared from compounds of the general formula (II-1-1) by established synthesis processes. A possible synthesis route for the cyclic aminocarboxylic acids of the general formula (II-1) is shown in Reaction Scheme 6.

Reaction Scheme 6

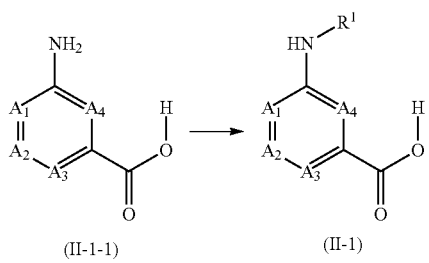

The radicals $A_1$-$A_4$ have the meanings described above. The radical $R^1$ represents the radicals described above except for hydrogen.

The conversion, known from the literature, of (II-1-1) into (II-1) can take place inter alia via reductive amination [Bioorganic & Medicinal Chemistry Letters 2005, 15(21), 4752-4756; WO2010-142402; US2010-0324056] or direct alkylation [Tetrahedron Letters 1977, (9), 771-774; Journal of the American Chemical Society 1997, 119(9), 2315-2316; Journal of Combinatorial Chemistry 2006, 8(6), 834-840].

Compounds of the general formula (II-2) can be prepared from compounds of the general formula (II-1) by established synthesis processes. A possible synthesis route for the cyclic aminocarboxylic acids of the general formula (II-2) is shown in Reaction Scheme 7.

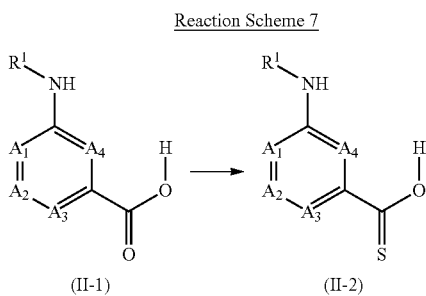

The radicals $A_1$-$A_4$ and $R^1$ have the meanings described above.

The conversion of compounds of the general formula (II-1) into compounds of the general formula (II-2) can be carried out analogously to reactions known from the literature [US2009-0023798; WO2009-044200; WO2010-085352].

Possible syntheses for the heterocyclic carboxylic acid derivatives of the general formula (V) are shown in Reaction Scheme 8.

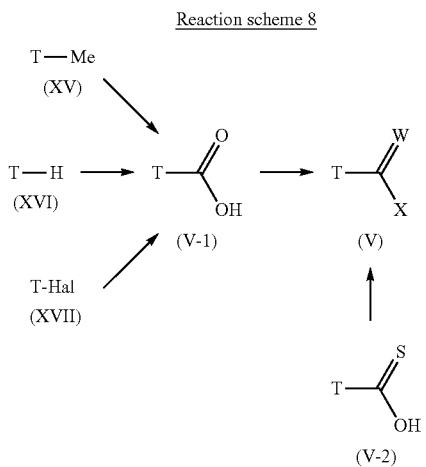

The radical W has the meanings described above. Hal represents a suitable halogen, for example bromine or iodine. X represents a suitable leaving group such as, for example, chlorine. T represents the grouping

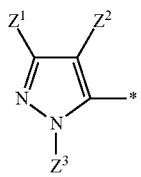

where the radicals $Z^1$, $Z^2$ and $Z^3$ have the meaning given above and the asterisk represents the point of attachment to the groupings Me, H, Hal, COOH, C(=S)OH or C(=W)X.

Heterocyclic carboxylic acids of the general structure (V-1) can be prepared inter alia from methyl derivatives of the general formula (XV) by oxidation of the methyl function. To this end, it is possible to employ the processes already mentioned for the oxidation of methyl groups of the compounds of the general structure (X).

Heterocyclic carboxylic acids of the general structure (V-1) can be prepared from precursors of the general structure (XVI) by deprotonation using a suitable base and by scavenging the corresponding carbanion with carbon dioxide [Journal of Medicinal Chemistry 2008, 51(4), 937-947; Bioorganic & Medicinal Chemistry Letters 2007, 17(22), 6274-6279]. Suitable bases are, for example, lithium diisopropylamide, n-butyllithium, s-butyllithium and compounds similar to these.

Also suitable for the process described above for preparing heterocyclic carboxylic acids of the general structure (V-1) are the appropriately halogenated heterocycles (XVII). However, here the carbanion is not generated by deprotonation but by a metallation reaction [Angewandte Chemie, International Edition 2008, 47(2), 311-315]. Preferred for these metallation reactions are n-butyllithium, t-butyllithium and isopropylmagnesium chloride.

Heterocyclic carboxylic acids of the general structure (V-1) can also be converted from halogenated precursors of the general structure (XVII) with the aid of palladium-catalyzed reactions known from the literature into the corresponding heterocyclic carboxylic esters [Russian Journal of Applied Chemistry 2007, 80(4), 571-575].

Heterocyclic carboxylic acids of the general structure (V-1) can furthermore be prepared from halogenated compounds of the general structure (XVII) by a substitution reaction of the halogens with cyanides and subsequent hydrolysis of the nitrile function with strong acid or bases [WO 2005079801].

Heterocyclic thiocarboxylic acids of the general structure (V-2) can be prepared from (V-1) analogously to the methods, known from the literature, described for the preparation of compounds of the general formula (II-2).

Heterocyclic activated carboxylic acid derivatives such as, for example, carbonyl halides as represented by the general structure (V) can be prepared by reacting a cyclic (thio)carboxylic acid represented by the formulae (V-1) and (V-2) with halogenating agents such as thionyl chloride, thionyl bromide, phosphoryl chloride, oxalyl chloride, phosphorus trichloride etc. [Organikum, Wiley-VCH, 22. Edition, 496ff].

Activated carboxylic acid derivatives of the general structure (II) can be prepared by generally known literature processes from carboxylic acids of the formula (II-1) [Organikum, Wiley-VCH, 22. Edition, 496ff; Chem. Ber. 1970, 788; J. Am. Chem. Soc 1967, 5012]. The compounds of the formula (II-1) are commercially available or can be prepared by known literature processes [Synthesis 2006, (4), 594-596; Tetrahedron Letters 1995, 36(25), 4369-72; Bioorganic & Medicinal Chemistry Letters 2007, 17(4), 1043-1046; PCT Int. Appl., 9502061, Journal of Organic Chemistry 1954, 19, 357-64; WO 2001083459].

Compounds of the general structures (III) are commercially available and/or can be prepared by the following processes, which are known from the literature or analogous [Journal of Organic Chemistry 1990, 55(14), 4276-81; WO 2005028429; WO 2005021485; Organic Letters 2010, 12(9), 1944-1947; Tetrahedron 1999, 55(24), 7625-7644].

Compounds of the general structure (V) are generally commercially available and/or can be prepared by known literature processes [Journal of Medicinal Chemistry 2008, 51(4), 937-947; Bioorganic & Medicinal Chemistry Letters 2007, 17(22), 6274-6279; Russian Journal of Applied Chemistry 2007, 80(4), 571-575; WO 2005079801; Journal of Organic Chemistry 2008, 73(9), 3523-3529; Bioorganic & Medicinal Chemistry Letters 2005, 15(22), 4898-4906; US2006069270]

The compounds of the general structure (VI) can be prepared by processes known from the literature from the compounds of the general structure (II) [Journal of the American Chemical Society 2001, 123(34), 8177-8188; Inorganica Chimica Acta 2006, 359(6), 1912-1922].

Compounds of the general structures (IX) to (XVII) are commercially available and/or known from the relevant specialist literature.

Oxidizing agents for the oxidation of alcoholic groups are known (cf., for example, oxidizing agents in Organic Synthesis by Oxidation with Metal Compounds, Mijs, de Jonge, Plenum Verlag, New York, 1986; Manganese Compounds as Oxidizing Agens in Organic Chemistry, Arndt, Open Court Publishing Company, La Salle, Ill., 1981; The Oxidation of Organic Compounds by Permanganate Ion and Hexavalent Chromium, Lee, Open Court Publishing Company, La Salle, Ill., 1980). An oxidation can be carried out, for example, in the presence of permanganates (for example potassium permanganate), metal oxides (for example manganese dioxide, chromium oxides which are used, for example, in dipyridinechromium(VI) oxide as Collins reagent (cf. J. C. Collins et al., Tetrahedron Lett. 30, 3363-3366, 1968)). Likewise in the presence of pyridinium chlorochromate (for example Corey's reagent) (cf. also R. O. Hutchins et al., Tetrahedron Lett. 48, 4167-4170, 1977; D. Landini et al. Synthesis 134-136, 1979) or ruthenium tetroxide (cf. S.-I. Murahashi, N. Komiya Ruthenium-catalyzed Oxidation of Alkenes, Alcohols, Amines, Amides, β-Lactams, Phenols and Hydrocarbons, in: Modern Oxidation Methods, Baeckvall, Jan-Erling (Eds.), Wiley-VCH-Verlag GmbH & Co. KGaA, 2004). Likewise suitable are ultrasound-induced oxidation reactions and the use of potassium permanganate (cf. J. Yamawaki et al., Chem. Lett. 3, 379-380, 1983).

All known suitable acidic or basic reaction auxiliaries can be used according to the procedures described in the literature to deblock/remove the protective group SG. When protective groups of the carbamate type are used for amino groups, preference is given to using acidic reaction auxiliaries. When the t-butylcarbamate protective group (BOC group) is employed, for example, mixtures of mineral acids such as hydrochloric acid, hydrobromic acid, nitric acid, sulphuric acid, phosphoric acid or organic acids such as benzoic acid, formic acid, acetic acid, trifluoroacetic acid, methanesulphonic acid, benzenesulphonic acid or toluenesulphonic acid and a suitable diluent such as water and/or an organic solvent such as tetrahydrofuran, dioxane, dichloromethane, chloroform, ethyl acetate, ethanol or methanol are used. Preference is given to mixture of hydrochloric acid or acetic acid with water and/or an organic solvent such as ethyl acetate.

It is known that certain reactions and preparation processes can be carried out particularly efficiently in the presence of diluents or solvents and basic or acidic reaction auxiliaries. It is also possible to use mixtures of the diluents or solvents. The diluents or solvents are advantageously employed in such an amount that the reaction mixture remains readily stirrable during the entire process.

Suitable diluents or solvents for carrying out the processes according to the invention are, in principle, all organic solvents which are inert under the specific reaction conditions. Examples include: halohydrocarbons (for example chlorohydrocarbons such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene), alcohols (for example methanol, ethanol, isopropanol, butanol), ethers (for example ethyl propyl ether, methyl tert-butyl ether, n-butyl ether, anisole, phenetole, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, dioxane, dichlorodiethyl ether and polyethers of ethylene oxide and/or propylene oxide), amines (for example trimethyl-, triethyl-, tripropyl-, tributylamine, N-methylmorpholine, pyridine and tetramethylenediamine), nitrohydrocarbons (for example nitromethane, nitroethane, nitropropane, nitrobenzene, chloronitrobenzene, o-nitrotoluene); nitriles (for example acetonitrile, propionitrile, butyronitrile, isobutyronitrile, benzonitrile, m-chlorobenzonitrile), tetrahydrothiophene dioxide, dimethyl sulphoxide, tetramethylene sulphoxide, dipropyl sulphoxide, benzyl methyl sulphoxide, diisobutyl sulphoxide, dibutyl sulphoxide, diisoamyl sulphoxide, sulphones (for example dimethyl, diethyl, dipropyl, dibutyl, diphenyl, dihexyl, methyl ethyl, ethyl propyl, ethyl isobutyl and pentamethylene sulphone), aliphatic, cycloaliphatic or aromatic hydrocarbons (for example pentane, hexane, heptane, octane, nonane and technical hydrocarbons), and also what are called "white spirits" with components having boiling points in the range from, for example, 40° C. to 250° C., cymene, petroleum fractions within a boiling range from 70° C. to 190° C., cyclohexane, methylcyclohexane, petroleum ether, ligroin, octane, benzene, toluene, chlorobenzene, bromobenzene, nitrobenzene, xylene, esters (for example methyl, ethyl, butyl and isobutyl acetate, dimethyl, dibutyl and ethylene carbonate); amides (for example hexamethylphosphoric triamide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-diformylpiperazine) and ketones (for example acetone, acetophenone, methyl ethyl ketone, methyl butyl ketone).

The basic reaction auxiliaries used to perform the process according to the invention may be all suitable acid binders. Examples include: alkaline earth metal or alkali metal compounds (e.g. hydroxides, hydrides, oxides and carbonates of lithium, sodium, potassium, magnesium, calcium and barium), amidine bases or guanidine bases (e.g. 7-methyl-1,5,7-triazabicyclo[4.4.0]dec-5-ene (MTBD); diazabicyclo[4.3.0]nonene (DBN), diazabicyclo[2.2.2]octane (DABCO), 1,8-diazabicyclo[5.4.0]undecene (DBU), cyclohexyltetrabutylguanidine (CyTBG), cyclohexyltetramethylguanidine (CyTMG), N,N,N,N-tetramethyl-1,8-naphthalenediamine, pentamethylpiperidine) and amines, especially tertiary amines (e.g. triethylamine, trimethylamine, tribenzylamine, triisopropylamine, tributylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylimidazole, N-methylpyrazole, N-methylmorpholine, N-methylhexamethylenediamine, pyridine, 4-pyrrolidinopyridine, 4-dimethylaminopyridine, quinoline, α-picoline, β-picoline, isoquinoline, pyrimidine, acridine, N,N,N',N'-tetramethylenediamine, N,N,N',N'-tetraethylenediamine, quinoxaline, N-propyldiisopropylamine, N-ethyldiisopropylamine, N,N'-dimethylcyclohexylamine, 2,6-lutidine, 2,4-lutidine or triethyldiamine).

The acidic reaction auxiliaries used to perform the process according to the invention include all mineral acids (e.g. hydrohalic acids such as hydrofluoric acid, hydrochloric acid, hydrobromic acid or hydriodic acid, and also sulphuric acid, phosphoric acid, phosphorous acid, nitric acid), Lewis acids (e.g. aluminium(III) chloride, boron trifluoride or its etherate, titanium(IV) chloride, tin(IV) chloride) and organic acids (e.g. formic acid, acetic acid, propionic acid, malonic acid, lactic acid, oxalic acid, fumaric acid, adipic acid, stearic acid, tartaric acid, oleic acid, methanesulphonic acid, benzoic acid, benzenesulphonic acid or para-toluenesulphonic acid).

If protective groups are intended in the reactions schemes, all generally known protective groups may be used. In particular those described by Greene T. W., Wuts P. G. W. in Protective Groups in Organic Synthesis; John Wiley & Sons, Inc. 1999, "Protection for the hydroxyl group including 1,2- and 1,3-diols".

Also suitable are protective groups
of the substituted methyl ether type (for example methoxymethyl ether (MOM), methylthiomethyl ether (MTM), (phenyldimethylsilyl)methoxymethyl ether (SNOM-OR), benzyloxymethyl ether (BOM-OR) para-methoxybenzyloxymethyl ether (PMBM-OR), para-nitrobenzyloxymethyl ether, ortho-nitrobenzyloxymethyl ether (NBOM-OR), (4-methoxyphenoxy)methyl ether (p-AOM-OR), guaiacolmethyl ether (GUM-OR), t-butoxymethyl ether, 4-pentyloxymethyl ether (POM-OR), silyloxymethyl ether, 2-methoxyethoxymethyl ether (MEM-OR), 2,2,2-trichloroethoxymethyl ether, bis(2-chloroethoxy)methyl ether, 2-(trimethylsilyl)ethoxymethyl ether (SEM-OR), methoxymethyl ether (MM-OR));
of the substituted ethyl ether type (for example 1-ethoxyethyl ether (EE-OR), 1-(2-chloroethoxy)ethyl ether (CEE-OR), 1-[2-(trimethylsilyl)ethoxy]ethyl ether (SEE-OR), 1-methyl-1-methoxyethyl ether (MIP-OR), 1-methyl-1-benzyloxyethyl ether (MBE-OR), 1-methyl-1-benzyloxy-2-fluoroethyl ether (MIP-OR), 1-methyl-1-phenoxyethyl ether, 2,2,2-trichloroethyl ether, 1,1-dianisyl-2,2,2-trichloroethyl ether (DATE-OR), 1,1,1,3,3,3-hexafluoro-2-phenylisopropyl ether (HIP-OR), 2-trimethylsilylethyl ether, 2-(benzylthio)ethyl ether, 2-(phenylselenyl)ethyl ether), an ether (for example tetrahydropyranyl ether (THP-OR), 3-bromotetrahydropyranyl ether (3-BrTHP-OR), tetrahydrothiopyranyl ether, 1-methoxycyclohexyl ether, 2- and 4-picolyl ether, 3-methyl-2-picolyl-N-oxido ether, 2-quinolinylmethyl ether (Qm-OR), 1-pyrenylmethyl ether, diphenylmethyl ether (DPM-OR), para,para'-dinitrobenzhydryl ether (DNB-OR), 5-dibenzosuberyl ether, triphenylmethyl ether (Tr-OR), alpha-naphthyldiphenylmethyl ether, para-methoxyphenyldiphenylmethyl ether (MMTrOR), di(para-methoxyphenyl)phenylmethyl ether (DMTr-OR), tri(para-methoxyphenyl)phenylmethyl ether (TMTr-OR), 4-(4'-bromophenacyloxy)phenyldiphenylmethyl ether, 4,4',4"-tris(4,5-dichlorophthalimidophenyl)methyl ether (CPTr-OR), 4,4',4"-tris(benzoyloxyphenyl)methyl ether (TBTr-OR), 4,4'-dimethoxy-3"-[N-(imidazolylmethyl)]trityl ether (IDTr-OR), 4,4'-dimethoxy-3"-[N-(imidazolyl-ethyl)carbamoyl] trityl ether (IETr-OR), 1,1-bis(4-methoxyphenyl)-1'-pyrenylmethyl ether (Bmpm-OR), 9-anthryl ether, 9-(9-phenyl)xanthenyl ether (Pixyl-OR), 9-(9-phenyl-10-oxo)anthryl ether (tritylone ether), 4-methoxytetrahydropyranyl ether (MTHP-OR), 4-methoxytetrahydrothiopyranyl ether, 4-methoxytetrahydrothiopyranyl S,S-dioxide, 1-[(2-chloro-4-methyl)phenyl]-4-methoxypiperidin-4-yl ether (CTMP-OR), 1-(2-fluorophenyl)-4-methoxypiperidin-4-yl ether (Fpmp-OR), 1,4-dioxan-2-yl ether, tetrahydrofuranyl ether, tetrahydrothiofuranyl ether, 2,3,3a,4,5,6,7,7a-octahydro-7,8,8-trimethyl-4,7-methanebenzofuran-2-yl ether (MBF-OR), t-butyl ether, allyl ether, propargyl ether, para-chlorophenyl ether, para-methoxyphenyl ether, para-nitrophenyl ether, para-2,4-dinitrophenyl ether (DNP-OR), 2,3,5,6-tetrafluoro-4-(trifluoromethyl)phenyl ether, benzyl ether (Bn-OR));
of the substituted benzyl ether type (for example para-methoxybenzyl ether (MPM-OR), 3,4-dimethoxybenzyl ether (DMPM-OR), ortho-nitrobenzyl ether, para-nitrobenzyl ether, para-halobenzyl ether, 2,6-dichlorobenzyl ether, para-aminoacylbenzyl ether (PAB-OR), para-azidobenzyl ether (Azb-OR), 4-azido-3-chlorobenzyl ether, 2-trifluoromethylbenzyl ether, para-(methylsulphinyl)benzyl ether (Msib-OR));
of a silyl ether type (for example trimethylsilyl ether (TMS-OR), triethylsilyl ether (TES-OR), triisopropylsilyl ether (TIPS-OR), dimethylisopropylsilyl ether (IPDMS-OR), diethylisopropylsilyl ether (DEIPS-OR), dimethylhexylsilyl ether (TDS-OR), t-butyldimethylsilyl ether (TBDMS-OR), t-butyldiphenylsilyl ether (TBDPS-OR), tribenzylsilyl ether, tri-para-xylylsilyl ether, triphenylsilyl ether (TPS-OR), diphenylmethylsilyl ether (DPMS-OR), di-t-butylmethylsilyl ether (DTBMS-OR), tris(trimethylsilyl)silyl ether (sisyl ether), di-t-butylmethylsilyl ether (DTBMS-OR), tris(trimethylsilyl)silyl ether (sisyl ether), (2-hydroxystyryl)dimethylsilyl ether (HSDMS-OR), (2-hydroxystyryl)diisopropylsilyl ether (HSDIS-OR), t-butylmethoxyphenylsilyl ether (TBMPS-OR), t-butoxydiphenylsilyl ether (DPTBOS-OR));
of the ester type (for example formate ester, benzoylformate ester, acetate ester (Ac-OR), chloroacetate ester, dichloroacetate ester, trichloroacetate ester, trifluoroacetate ester, (TFA-OR), methoxyacetate ester, triphenylmethoxyacetate ester, phenoxyacetate ester, para-chlorophenoxyacetate ester, phenylacetate ester, diphenylacetate ester (DPA-OR), nicotinate ester, 3-phenylpropionate ester, 4-pentoate ester, 4-oxopentoate ester (levulinate) (Lev-OR) 4,4-(ethylenedithio)pentanoate ester (LevS-OR), 5-[3-bis(4-methoxyphenyl)hydroxymethoxyphenoxy]levulinate ester, pivaloate ester (Pv-OR), 1-adamantanoate ester, crotonate ester, 4-methoxycrotonate ester, benzoate ester (Bz-OR), para-phenylbenzoate ester, 2,4,6-trimethylbenzoate ester (mesitoate), 4-(methylthiomethoxy)butyrate ester (MTMB-OR), 2-(methylthiomethoxymethyl)benzoate ester (MTMT-OR),
of the ester type (for example methyl carbonate, methoxymethyl carbonate, 9-fluorenylmethyl carbonate (Fmoc-OR), ethyl carbonate, 2,2,2-trichloroethyl carbonate (Troc-OR), 1,1-dimethyl-2,2,2-trichloroethyl carbonate (TCBOC-OR), 2-(trimethylsilyl)ethyl carbonate (TMS-OR), 2-(phenylsulphonyl)ethyl carbonate (Ps-OR), 2-(triphenylphosphonio)ethyl carbonate (Peoc-OR), t-butyl carbonate (Boc-OR), isobutyl carbonate, vinyl carbonate, allyl carbonate (Alloc-OR), para-nitrophenyl carbonate, benzyl carbonate (Z-OR), para-methoxybenzyl carbonate, 3,4-dimethoxybenzyl carbonate, ortho-nitrobenzyl carbonate, para-nitrobenzyl carbonate, 2-dansylethyl carbonate (Dnseoc-OR), 2-(4-nitrophenyl)ethyl carbonate (Npeoc-OR), 2-(2,4-dinitrophenyl)ethyl carbonate (Dnpeoc)), and
of the sulphate type (for example allylsulphonate (Als-OR), methanesulphonate (Ms-OR), benzylsulphonate, tosylate (Ts-OR), 2-[(4-nitrophenyl)ethyl]sulphonate (Npes-OR)).

Suitable catalysts for carrying out a catalytic hydrogenation in the process according to the invention are all customary hydrogenation catalysts such as, for example, platinum catalysts (for example platinum plate, platinum sponge, platinum black, colloidal platinum, platinum oxide, platinum wire), palladium catalysts (for example palladium sponge, palladium black, palladium oxide, palladium/carbon, colloidal palladium, palladium/barium sulphate, palladium/barium carbonate, palladium hydroxide, nickel catalysts (for example reduced nickel, nickel oxide, Raney nickel), ruthenium catalysts, cobalt catalysts (for example reduced cobalt, Raney cobalt), copper catalysts (for example reduced copper, Raney copper, Ullmann copper). Preference is given to using noble metal catalysts (for example platinum and palladium or ruthenium catalysts), which may be applied to a suitable support (for example carbon or silicon), rhodium catalysts (for example tris(triphenylphosphine)rhodium(I) chloride in the presence of triphenylphosphine). Furthermore, it is possible to use "chiral hydrogenation catalysts" (for example those comprising chiral diphosphine ligands such as (2S,3S)-(−)-2,3-bis(diphenylphosphino)butane [(S,S)-chiraphos] or (R)-(+)-2,2'- or (S)-(−)-2,2'-bis(diphenylphosphino)-1,1'-binaphthalene [R(+)-BINAP or S(−)-BINAP]), whereby the proportion of an isomer in the isomer mixture is increased or the formation of another isomer is virtually completely suppressed.

Salts of the compounds according to the invention are prepared by standard methods. Representative acid addition salts are, for example, those formed by reaction with inorganic acids, such as, for example, sulphuric acid, hydrochloric acid, hydrobromic acid, phosphoric acid, or organic carboxylic acids such as acetic acid, trifluoroacetic acid, citric acid, succinic acid, butyric acid, lactic acid, formic acid, fumaric acid, maleic acid, malonic acid, camphoric acid, oxalic acid, phthalic acid, propionic acid, glycolic acid, glutaric acid, stearic acid, salicylic acid, sorbic acid, tartaric acid, cinnamic acid, valeric acid, picric acid, benzoic acid or organic sulphonic acids such as methanesulphonic acid and 4-toluenesulphonic acid.

Also representative are salts of compounds according to the invention formed from organic bases such as, for example, pyridine or triethylamine, or those formed from inorganic bases such as, for example, hydrides, hydroxides or carbonates of sodium, lithium, calcium, magnesium or barium, provided the compounds of the general formula (I) have a structural element suitable for this salt formation.

Synthesis methods for preparing heterocyclic N-oxides and t-amines are known. They can be obtained using peroxy acids (for example peracetic acid and meta-chloroperbenzoic acid (MCPBA), hydrogen peroxide, alkyl hydroperoxides (for example t-butyl hydroperoxide), sodium perborate and dioxiranes (for example dimethyldioxirane). These methods have been described, for example, by T. L. Gilchrist, in Comprehensive Organic Synthesis, Vol. 7, pp. 748-750, 1992, S. V. Ley, (Ed.), Pergamon Press; M. Tisler, B. Stanovnik, in Comprehensive Heterocyclic Chemistry, Vol. 3, pp. 18-20, 1984, A. J. Boulton, A. McKillop, (Eds.), Pergamon Press; M. R. Grimmett, B. R. T. Keene in Advances in Heterocyclic Chemistry, Vol. 43, pp. 149-163, 1988, A. R. Katritzky, (Ed.), Academic Press; M. Tisler, B. Stanovnik, in Advances in Heterocyclic Chemistry, Vol. 9, pp. 285-291, 1968, A. R. Katritzky, A. J. Boulton (Eds.), Academic Press; G. W. H. Cheeseman, E. S. G. Werstiuk in Advances in Heterocyclic Chemistry, Vol. 22, pp. 390-392, 1978, A. R. Katritzky, A. J. Boulton, (Eds.), Academic Press.

EXPERIMENTAL PART

Preparation Process A

Example (1)

4-Bromo-N-{4-chloro-3-[(1-cyanocyclopropyl)carbamoyl]phenyl}-3-(1-fluorocyclopropyl)-1-methyl-1H-pyrazole-5-carboxamide

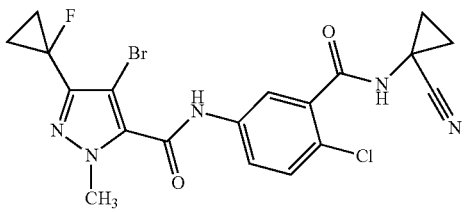 [SMILES: Cn1nc(C2(F)CC2)c(Br)c1C(=O)Nc1ccc(Cl)c(C(=O)NC2(C#N)CC2)c1]

120 mg (0.45 mmol) of 4-bromo-3-(1-fluorocyclopropyl)-1-methyl-1H-pyrazole-5-carboxylic acid are suspended in 20 ml of dichloromethane p.a., and 0.02 ml of N,N-dimethylformamide p.a. is added. 0.119 ml (1.36 mmol) of oxalyl chloride is added dropwise to this mixture. The mixture is then stirred at room temperature for 30 minutes and then under reflux for 30 minutes. After cooling, the reaction mixture is concentrated under reduced pressure on a rotary evaporator. The crude product obtained in this way is reacted further without further purification.

108 mg (0.45 mmol) of 5-amino-2-chloro-N-(1-cyanocyclopropyl)benzamide and 92 mg (0.68 mmol) of silver(I) cyanide are initially charged in 10 ml of dichlormethane p.a. A solution of 129 mg (0.45 mmol) of 4-bromo-3-(1-fluorocyclopropyl)-1-methyl-1H-pyrazole-5-carbonyl chloride in 10 ml of dichloromethane p.a. is added dropwise to this suspension. The reaction mixture is stirred at room temperature for 16 h and then filtered through silica gel, and the filter cake is washed with ethyl acetate. The solvents are removed under reduced pressure on a rotary evaporator.

This gives 170 mg (78%) of 4-bromo-N-{4-chloro-3-[(1-cyanocyclopropyl)carbamoyl]phenyl}-3-(1-fluorocyclopropyl)-1-methyl-1H-pyrazole-5-carboxamide as a colourless solid.

$^1$H-NMR (400 MHz, $d_6$-DMSO): δ=10.96 (s, 1H), 9.49 (s, 1H), 7.85 (d, 1H), 7.74 (dd, 1H), 7.55 (d, 1H), 3.93 (s, 3H), 1.57-1.61 (m, 2H), 1.40-1.45 (m, 2H), 1.23-1.28 (m, 2H), 1.08-1.11 (m, 2H) ppm.

HPLC-MS$^{a)}$: log P=2.50, mass (m/z)=482 [M+H]$^+$.

Preparation Process B

Example (2)

N-{4-Chloro-3-[(1-cyanocyclopropyl)carbamoyl]phenyl}-N,1-dimethyl-3,4-bis(trifluoromethyl)-1H-pyrazole-5-carboxamide

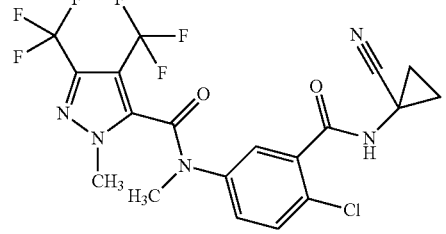

150.0 mg (0.29 mmol) of 2-chloro-5-(methyl{[1-methyl-3,4-bis(trifluoromethyl)-1H-pyrazol-5-yl]carbonyl}amino)benzoic acid are suspended in 5.0 ml of dichlormethane p.a. 0.02 ml of N,N-dimethylformamide p.a. and 0.075 ml (0.86 mmol) oxalyl chloride are then added successively to the suspension. The reaction mixture is stirred at room temperature for 0.5 h and then heated under reflux for 40 minutes. The solvent is removed under reduced pressure on a rotary evaporator. The 2-chloro-5-(methyl{[1-methyl-3,4-bis(trifluoromethyl)-1H-pyrazol-5-yl]carbonyl}amino)benzoyl chloride formed is used for the subsequent synthesis step without further purification.

68.3 mg (0.58 mmol) of 1-aminocyclopropanecarbonitrile hydrochloride are initially charged in 5.0 ml of dichloromethane p.a., and 0.148 ml (0.86 mmol) of N-ethyldiisopropylamine and 156 mg of 2-chloro-5-(methyl{[1-methyl-3,4-bis(trifluoromethyl)-1H-pyrazol-5-yl]carbonyl}amino)benzoyl chloride (0.29 mmol) dissolved in 5.0 ml of dichloromethane p.a. are then added in succession. The reaction is stirred at room temperature for 16 hours. The reaction solution is diluted with 30 ml of ethyl acetate. The organic phase is washed twice with 1 N hydrochloric acid, once with 1 N aqueous sodium hydroxide solution and once with saturated sodium chloride solution. The organic phase is dried over magnesium sulphate and filtered and the solvent is removed on a rotary evaporator under reduced pressure.

The crude product is purified by preparative HPLC. This gives 64 mg (45%) of N-{4-chloro-3-[(1-cyanocyclopropyl)carbamoyl]phenyl}-N,1-dimethyl-3,4-bis(trifluoromethyl)-1H-pyrazole-5-carboxamide as a colourless solid.

$^1$H-NMR (400 MHz, $d_3$-acetonitrile, mixture of cis- and trans-configured amides): δ=7.42-7.66 (m, 2H), 7.40 (d, 1H), 7.29 (d, 2H), 7.18 (dd, 1H), 3.83 & 3.99 (2 s, together 3H), 3.46 & 3.23 (2 s, together 3H), 1.54-1.60 (m, 2H), 1.25-1.37 (m, 2H) ppm.

HPLC-MS$^{a)}$: log P=2.81, mass (m/z)=494 [M+H]$^+$.

Preparation Process C

Example (50)

N-{4-Chloro-3-[(1-cyanocyclopropyl)carbamoyl]phenyl}-N-ethyl-3-(pentafluoroethyl)-1-propyl-4-(trifluoromethyl)-1H-pyrazole-5-carboxamide

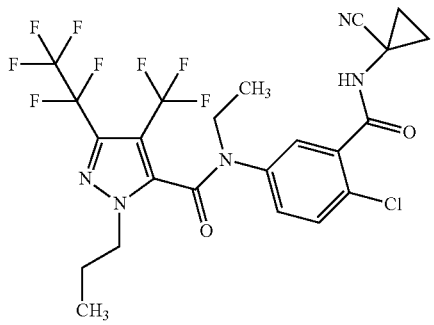 [SMILES: CCCn1nc(C(F)(F)C(F)(F)F)c(C(F)(F)F)c1C(=O)N(CC)c1ccc(Cl)c(C(=O)NC2(C#N)CC2)c1]

70 mg (0.13 mmol) of N-{4-chloro-3-[(1-cyanocyclopropyl)carbamoyl]phenyl}-3-(pentafluoroethyl)-1-propyl-4-(trifluoromethyl)-1H-pyrazole-5-carboxamide and 35 mg (0.14 mmol) of potassium carbonate are suspended in 1.4 ml of N,N-dimethylformamide p.a. Over a period of 16 h, a total of 29 mg (0.19 mmol) of iodoethane are added gradually to the mixture. After the addition has ended, the reaction solution is stirred at room temperature for 20 h. The reaction mixture is diluted with water, and the aqueous phase is extracted three times with ethyl acetate. The combined organic phases are washed twice with saturated sodium chloride solution, dried over sodium sulphate and filtered. The solvents are removed on a rotary evaporator under reduced pressure.

The crude product is purified by column chromatography on silica gel. This gives 30 mg (41%) of N-{4-chloro-3-[(1-cyanocyclopropyl)carbamoyl]phenyl}-N-ethyl-3-(pentafluoroethyl)-1-propyl-4-(trifluoromethyl)-1H-pyrazole-5-carboxamide as a colourless solid.

$^1$H-NMR (400 MHz, $d_6$-DMSO, mixture of cis- and trans-configured amides): δ=9.56 & 9.42 (2s, together 1H), 7.69 & 7.56 (2d, together 1H), 7.63 & 7.42 (2d, together 1H), 7.48 & 7.28 (2dd, together 1H), 3.52-4.32 (m, 4H), 0.79-1.87 (m, 12H) ppm.

HPLC-MS$^{a)}$: log P=4.06, mass (m/z)=586 [M+H]$^+$.

Preparation Process D

Example (40)

N-{3-[Acetyl(1-cyanocyclopropyl)carbamoyl]-4-chlorophenyl}-1-methyl-3-(pentafluoroethyl)-4-(trifluoromethyl)-1H-pyrazole-5-carboxamide

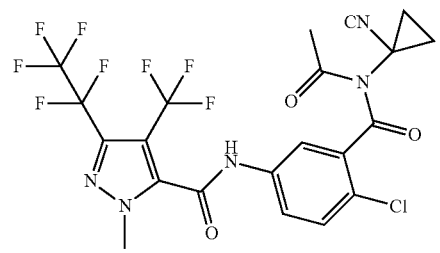

300 mg (0.57 mmol) of N-{4-chloro-3-[(1-cyanocyclopropyl)carbamoyl]phenyl}-1-methyl-3-(pentafluoroethyl)-4-(trifluoromethyl)-1H-pyrazole-5-carboxamide are dissolved in 6.0 ml of dichloromethane p.a. and cooled in an ice bath. 0.17 ml (0.99 mmol) of N-ethyldiisopropylamine and 49 mg (0.62 mmol) of acetyl chloride are added successively to the solution. The reaction is then warmed to room temperature and stirred for 16 h. The reaction solution is diluted with dichloromethane and then washed with water. The organic phase is dried over sodium sulphate and filtered, and the solvent is removed on a rotary evaporator under reduced pressure.

The crude product is purified by preparative HPLC. This gives 130 mg (40%) of N-{3-[acetyl(1-cyanocyclopropyl)carbamoyl]-4-chlorophenyl}-1-methyl-3-(pentafluoroethyl)-4-(trifluoromethyl)-1H-pyrazole-5-carboxamide as a colourless solid.

$^1$H-NMR (400 MHz, $d_6$-DMSO): δ=11.49 (s, 1H), 7.90 (d, 1H), 7.70 (dd, 1H), 7.57 (d, 1H), 4.03 (s, 3H), 2.49 (s, 3H), 1.85-1.91 (m, 2H), 1.57-1.67 (m, 2H) ppm.

HPLC-MS$^{a)}$: log P=3.81, Masse (m/z)=572 [M+H]$^+$.

$^{a)}$ Note regarding the determination of the log P values and mass detection The determination of the given log P values was carried out in accordance with EEC Directive 79/831 Annex V.A8 by HPLC (High Performance Liquid Chromatography) on a reversed-phase column (C18). Agilent 1100 LC system; 50*4.6 Zorbax Eclipse Plus C18 1.8 micron; mobile phase A: acetonitrile (0.1% formic acid); mobile phase B: water (0.09% formic acid); linear gradient from 10% acetonitrile to 95% acetonitrile in 4.25 min, then 95% acetonitrile for a further 1.25 min; oven temperature 55° C.; flow rate: 2.0 ml/min Mass detection is via an Agilend MSD system.

$^{b)}$ Note regarding the determination of the log P values and mass detection The stated log P values were determined in accordance with EEC Directive 79/831 Annex V.A8 by HPLC (High Performance Liquid Chromatography) using a reversed-phase column (C18). HP1100; 50*4.6 Zorbax Eclipse Plus C18 1.8 micron; mobile phase A: acetonitrile (0.1% formic acid); mobile phase B: water (0.08% formic acid); linear gradient from 5% acetonitrile to 95% acetonitrile in 1.70 min, then 95% acetonitrile for a further 1.00 min; oven temperature 55° C.; flow rate: 2.0 ml/min Mass detection is via the mass detector Micromass ZQ2000 from Waters.

The compounds listed in Tables 1 & 2 were prepared using the Preparation Processes A to D described above.

TABLE 1

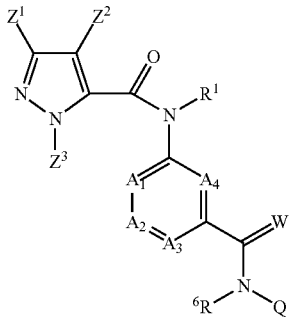

(I-1)

| Ex. No | $Z^1$ | $Z^2$ | $Z^3$ | $R^1$ | $A^1$ | $A^2$ | $A^3$ | $A^4$ | W | $R^6$ | Q | logP | Mass [m/z] 1 |
|---|---|---|---|---|---|---|---|---|---|---|---|---|---|
| 1 | 1-fluoro-cyclopropyl | Br | Me | H | CH | CH | CCl | CH | O | H | 1-cyano-cyclopropyl | 2.50 [a] | 482 [a] |
| 2 | $CF_3$ | $CF_3$ | Me | Me | CH | CH | CCl | CH | O | H | 1-cyano-cyclopropyl | 2.81 [a] | 494 [a] |
| 3 | 1-chloro-cyclopropyl | Cl | Me | Me | CH | CH | CCl | CH | O | H | 1-cyano-cyclopropyl | 2.46 [a] | 466 [a] |
| 4 | penta-fluoroethyl | $CF_3$ | Me | Me | CH | CH | CCl | CH | O | Et | 1-cyano-cyclopropyl | 3.77 [a] | 572 [a] |
| 5 | penta-fluoroethyl | $CF_3$ | Me | Me | CH | CH | CCl | CH | O | Me | 1-cyano-cyclopropyl | 3.59 [a] | 558 [a] |
| 6 | penta-fluoroethyl | $CF_3$ | Me | Et | CH | CH | CCl | CH | O | H | 1-cyano-cyclopropyl | 3.36 [a] | 558 [a] |
| 7 | penta-fluoroethyl | $CF_3$ | Me | H | CH | CH | CCl | CH | O | H | 1-cyano-cyclobutyl | 3.55 [a] | 544 [a] |
| 8 | penta-fluoroethyl | $CF_3$ | Me | Me | CH | CH | CCl | CH | O | H | 1-cyano-cyclopropyl | 3.21 [a] | 544 [a] |
| 9 | $CF_3$ | $CF_3$ | Me | H | CH | CH | CCl | CH | O | H | 1-cyano-cyclopropyl | 2.85 [a] | 480 [a] |
| 10 | penta-fluoroethyl | $CF_3$ | Me | H | CH | CH | CCl | CH | O | H | 1-cyano-cyclopropyl | 3.27 [a] | 530 [a] |
| 11 | $CF_3$ | $CF_3$ | Me | H | CH | CBr | CBr | CH | O | H | 1-cyano-cyclopropyl | 3.30 | 604 |
| 12 | $CF_3$ | $CF_3$ | Me | H | CH | CCl | CBr | CH | O | H | 1-cyano-cyclopropyl | 3.27 | 560 |
| 13 | penta-fluoroethyl | $CF_3$ | Me | H | CH | CBr | CCl | CH | O | H | 1-cyano-cyclopropyl | 3.67 | 610 |
| 14 | penta-fluoroethyl | $CF_3$ | Me | H | CH | CH | CBr | CH | O | H | 1-cyano-cyclopropyl | 3.31 | 576 |
| 15 | penta-fluoroethyl | $CF_3$ | Me | H | CH | CH | CCl | CH | O | propionyl | 1-cyano-cyclopropyl | 4.17 | 584 [2] |
| 16 | penta-fluoroethyl | $CF_3$ | Me | H | CH | CCl | CBr | CH | O | H | 1-cyano-cyclopropyl | 3.73 | 610 |
| 17 | 1-fluoro-cyclopropyl | Cl | Me | H | CH | CH | CCl | CH | O | H | 1-cyano-cyclopropyl | 2.50 | 436 |
| 18 | penta-fluoroethyl | $CF_3$ | Me | acetyl | CH | CH | CCl | CH | O | acetyl | 1-cyano-cyclopropyl | 4.04 | |
| 19 | penta-fluoroethyl | $CF_3$ | Me | methoxy-carbonyl | CH | CH | CCl | CH | O | H | 1-cyano-cyclopropyl | 3.69 | 588 |
| 20 | penta-fluoroethyl | $CF_3$ | Me | ethoxy-carbonyl | CH | CH | CCl | CH | O | H | 1-cyano-cyclopropyl | 3.95 | 602 |
| 21 | penta-fluoroethyl | $CF_3$ | Me | methoxy-carbonyl | CH | CH | CCl | CH | O | methoxy-carbonyl | 1-cyano-cyclopropyl | 4.32 | 646 |
| 22 | penta-fluoroethyl | $CF_3$ | Me | ethoxy-carbonyl | CH | CH | CCl | CH | O | ethoxy-carbonyl | 1-cyano-cyclopropyl | 4.80 | 674 |
| 23 | penta-fluoroethyl | $CF_3$ | Me | 2,2-dimethyl-propanoyl | CH | CH | CCl | CH | O | H | 1-cyano-cyclopropyl | 4.40 | 614 |
| 24 | penta-fluoroethyl | $CF_3$ | Me | H | CH | CMe | CCl | CH | O | H | 1-cyano-cyclopropyl | 3.51 | 544 |
| 25 | penta-fluoroethyl | $CF_3$ | Me | H | CH | CH | Cl | CH | O | H | 1-cyano-cyclopropyl | 3.43 | 620 [2] |
| 26 | penta-fluoroethyl | $CF_3$ | Me | prop-2-yn-1-yl | CH | CH | CCl | CH | O | H | 1-cyano-cyclopropyl | 3.41 | 568 |
| 27 | penta-fluoroethyl | $CF_3$ | Me | H | CH | CH | CF | CH | O | H | 1-cyano-cyclopropyl | 3.21 | 514 |
| 28 | penta-fluoroethyl | $CF_3$ | Me | 4-chloro-benzyl | CH | CH | CCl | CH | O | H | 1-cyano-cyclopropyl | 4.30 | 654 |
| 29 | penta-fluoroethyl | $CF_3$ | Me | isobutyryl | CH | CH | CCl | CH | O | H | 1-cyano-cyclopropyl | 4.38 | 600 |
| 30 | penta-fluoroethyl | $CF_3$ | Me | but-2-yn-1-yl | CH | CH | CCl | CH | O | H | 1-cyano-cyclopropyl | 3.60 | 582 |

TABLE 1-continued

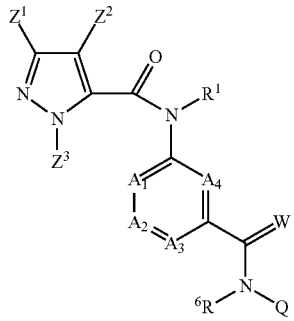

(I-1)

| Ex. No | $Z^1$ | $Z^2$ | $Z^3$ | $R^1$ | $A^1$ | $A^2$ | $A^3$ | $A^4$ | W | $R^6$ | Q | logP | Mass [m/z] 1 |
|---|---|---|---|---|---|---|---|---|---|---|---|---|---|
| 31 | penta-fluoroethyl | $CF_3$ | Me | benzyl | CH | CH | CCl | CH | O | H | 1-cyano-cyclopropyl | 3.97 | 620 |
| 32 | penta-fluoroethyl | $CF_3$ | Me | pyridin-2-ylmethyl | CH | CH | CCl | CH | O | H | 1-cyano-cyclopropyl | 3.53 | 621 |
| 33 | penta-fluoroethyl | $CF_3$ | Me | propionyl | CH | CH | CCl | CH | O | H | 1-cyano-cyclopropyl | 3.91 | 586 |
| 34 | penta-fluoroethyl | $CF_3$ | Et | H | CH | CH | CCl | CH | O | H | 1-cyano-cyclopropyl | 3.53 | 544 |
| 35 | penta-fluoroethyl | $CF_3$ | Pr | H | CH | CH | CCl | CH | O | H | 1-cyano-cyclopropyl | 3.87 | 558 |
| 36 | penta-fluoroethyl | $CF_3$ | Pr | H | CH | CH | CF | CH | O | H | 1-cyano-cyclopropyl | 3.74 | 542 |
| 37 | penta-fluoroethyl | $CF_3$ | Et | H | CH | CH | CF | CH | O | H | 1-cyano-cyclopropyl | 3.44 | 528 |
| 38 | penta-fluoroethyl | $CF_3$ | Et | Me | CH | CH | CCl | CH | O | H | 1-cyano-cyclopropyl | 3.57 | 558 |
| 39 | penta-fluoroethyl | $CF_3$ | Me | Et | CH | CBr | CCl | CH | O | H | 1-cyano-cyclopropyl | 3.92 | 638 |
| 40 | penta-fluoroethyl | $CF_3$ | Me | H | CH | CH | CCl | CH | O | acetyl | 1-cyano-cyclopropyl | 3.81 | 572 |
| 41 | penta-fluoroethyl | $CF_3$ | Et | Me | CH | CH | CCl | CH | O | Me | 1-cyano-cyclopropyl | 3.85 | 572 |
| 42 | penta-fluoroethyl | methyl-sulphanyl | Me | H | CH | CH | CCl | CH | O | H | 1-cyano-cyclopropyl | 3.43 | 508 |
| 43 | penta-fluoroethyl | $CF_3$ | Et | Et | CH | CH | CCl | CH | O | H | 1-cyano-cyclopropyl | 3.68 | 572 |
| 44 | penta-fluoroethyl | $CF_3$ | Me | cyano-methyl | CH | CH | CCl | CH | O | H | 1-cyano-cyclopropyl | 3.25 | 569 |
| 45 | penta-fluoroethyl | methyl-sulphinyl | Me | H | CH | CH | CCl | CH | O | H | 1-cyano-cyclopropyl | 2.91 | 524 |
| 46 | penta-fluoroethyl | $CF_3$ | Pr | Me | CH | CH | CCl | CH | O | Me | 1-cyano-cyclopropyl | 4.26 | 586 |
| 47 | penta-fluoroethyl | $CF_3$ | Pr | Me | CH | CH | CF | CH | O | Me | 1-cyano-cyclopropyl | 4.05 | 570 |
| 48 | penta-fluoroethyl | $CF_3$ | Et | Me | CH | CH | CF | CH | O | Me | 1-cyano-cyclopropyl | 3.76 | 556 |
| 49 | penta-fluoroethyl | methyl-sulphonyl | Me | H | CH | CH | CCl | CH | O | H | 1-cyano-cyclopropyl | 2.47 | 540 |
| 50 | penta-fluoroethyl | $CF_3$ | Pr | Et | CH | CH | CCl | CH | O | H | 1-cyano-cyclopropyl | 4.06 | 586 |
| 51 | penta-fluoroethyl | $CF_3$ | Pr | Et | CH | CH | CCl | CH | O | Et | 1-cyano-cyclopropyl | 4.68 | 614 |
| 52 | penta-fluoroethyl | $CF_3$ | Et | Et | CH | CH | CCl | CH | O | Et | 1-cyano-cyclopropyl | 4.26 | 600 |
| 53 | penta-fluoroethyl | $CF_3$ | Me | acetyl | CH | CH | CCl | CH | O | H | 1-cyano-cyclopropyl | 3.63 | 572 |
| 54 | penta-fluoroethyl | $CF_3$ | Me | pyridin-3-ylmethyl | CH | CH | CCl | CH | O | H | 1-cyano-cyclopropyl | 2.85 | 621 |
| 55 | penta-fluoroethyl | $CF_3$ | Me | 2-methylprop-2-en-1-yl | CH | CH | CCl | CH | O | H | 1-cyano-cyclopropyl | 3.78 | 584 |
| 56 | penta-fluoroethyl | $CF_3$ | Me | pyridin-4-ylmethyl | CH | CH | CCl | CH | O | H | 1-cyano-cyclopropyl | 2.52 | 621 |
| 57 | penta-fluoroethyl | $CF_3$ | prop-2-yn-1-yl | H | CH | CH | CCl | CH | O | H | 1-cyano-cyclopropyl | 3.58 | 554 |
| 58 | penta-fluoroethyl | $CF_3$ | prop-2-en-1-yl | H | CH | CH | CCl | CH | O | H | 1-cyano-cyclopropyl | 3.65 | 556 |
| 59 | penta-fluoroethyl | $CF_3$ | Me | H | CH | CF | CBr | CH | O | H | 1-cyano-cyclopropyl | 3.58 | 592 |
| 60 | penta-fluoroethyl | $CF_3$ | Me | propionyl | CH | CH | CCl | CH | O | propionyl | 1-cyano-cyclopropyl | 4.68 | |

TABLE 1-continued

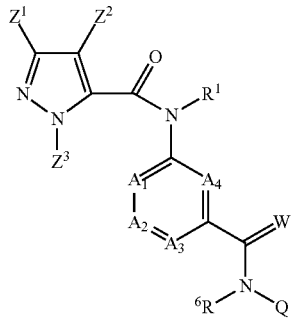

(I-1)

| Ex. No | $Z^1$ | $Z^2$ | $Z^3$ | $R^1$ | $A^1$ | $A^2$ | $A^3$ | $A^4$ | W | $R^6$ | Q | logP | Mass [m/z] 1 |
|---|---|---|---|---|---|---|---|---|---|---|---|---|---|
| 61 | pentafluoroethyl | $CF_3$ | Me | H | CH | CH | CCl | CH | O | Et | 1-cyanocyclopropyl | 3.86 | 558 |
| 62 | pentafluoroethyl | $CF_3$ | Me | H | CH | CH | CCl | CH | O | Me | 1-cyanocyclopropyl | 3.66 | 544 |
| 63 | pentafluoroethyl | $CF_3$ | Me | isopropoxycarbonyl | CH | CH | CCl | CH | O | H | 1-cyanocyclopropyl | 4.19 | 616 |
| 64 | pentafluoroethyl | $CF_3$ | 2,2,2-trifluoroethyl | H | CH | CH | CCl | CH | O | H | 1-cyanocyclopropyl | 3.60 | 598 |
| 65 | $CF_3$ | $CF_3$ | Me | H | CH | CH | CCl | CH | S | H | 1-cyanocyclopropyl | | |
| 66 | pentafluoroethyl | $CF_3$ | Me | Me | CH | CH | CCl | CH | S | H | 1-cyanocyclopropyl | | |
| 67 | pentafluoroethyl | $CF_3$ | Me | H | CH | CH | CCl | CH | S | H | 1-cyanocyclobutyl | | |
| 68 | pentafluoroethyl | $CF_3$ | Me | Et | CH | CH | CCl | CH | S | H | 1-cyanocyclopropyl | | |
| 69 | pentafluoroethyl | $CF_3$ | Me | Me | CH | CH | CCl | CH | S | Me | 1-cyanocyclopropyl | | |
| 70 | pentafluoroethyl | $CF_3$ | Me | Me | CH | CH | CCl | CH | S | Et | 1-cyanocyclopropyl | | |
| 71 | 1-chlorocyclopropyl | Cl | Me | Me | CH | CH | CCl | CH | S | H | 1-cyanocyclopropyl | | |
| 72 | $CF_3$ | $CF_3$ | Me | Me | CH | CH | CCl | CH | S | H | 1-cyanocyclopropyl | | |
| 73 | pentafluoroethyl | $CF_3$ | Me | H | CH | CH | CCl | CH | S | H | 1-cyanocyclopropyl | | |
| 74 | 1-fluorocyclopropyl | Br | Me | H | CH | CH | CCl | CH | S | H | 1-cyanocyclopropyl | | |
| 75 | $CF_3$ | $CF_3$ | Me | H | CH | CBr | CBr | CH | S | H | 1-cyanocyclopropyl | | |
| 76 | $CF_3$ | $CF_3$ | Me | H | CH | CCl | CBr | CH | S | H | 1-cyanocyclopropyl | | |
| 77 | pentafluoroethyl | $CF_3$ | Me | H | CH | CBr | CCl | CH | S | H | 1-cyanocyclopropyl | | |
| 78 | pentafluoroethyl | $CF_3$ | Me | H | CH | CH | CBr | CH | S | H | 1-cyanocyclopropyl | | |
| 79 | pentafluoroethyl | $CF_3$ | Me | H | CH | CH | CCl | CH | S | propionyl | 1-cyanocyclopropyl | | |
| 80 | pentafluoroethyl | $CF_3$ | Me | H | CH | CCl | CBr | CH | S | H | 1-cyanocyclopropyl | | |
| 81 | 1-fluorocyclopropyl | Cl | Me | H | CH | CH | CCl | CH | S | H | 1-cyanocyclopropyl | | |
| 82 | pentafluoroethyl | $CF_3$ | Me | acetyl | CH | CH | CCl | CH | S | acetyl | 1-cyanocyclopropyl | | |
| 83 | pentafluoroethyl | $CF_3$ | Me | methoxycarbonyl | CH | CH | CCl | CH | S | H | 1-cyanocyclopropyl | | |
| 84 | pentafluoroethyl | $CF_3$ | Me | ethoxycarbonyl | CH | CH | CCl | CH | S | H | 1-cyanocyclopropyl | | |
| 85 | pentafluoroethyl | $CF_3$ | Me | methoxycarbonyl | CH | CH | CCl | CH | S | methoxycarbonyl | 1-cyanocyclopropyl | | |
| 86 | pentafluoroethyl | $CF_3$ | Me | ethoxycarbonyl | CH | CH | CCl | CH | S | ethoxycarbonyl | 1-cyanocyclopropyl | | |
| 87 | pentafluoroethyl | $CF_3$ | Me | 2,2-dimethylpropanoyl | CH | CH | CCl | CH | S | H | 1-cyanocyclopropyl | | |
| 88 | pentafluoroethyl | $CF_3$ | Me | H | CH | CMe | CCl | CH | S | H | 1-cyanocyclopropyl | | |
| 89 | pentafluoroethyl | $CF_3$ | Me | H | CH | CH | Cl | CH | S | H | 1-cyanocyclopropyl | | |
| 90 | pentafluoroethyl | $CF_3$ | Me | prop-2-yn-1-yl | CH | CH | CCl | CH | S | H | 1-cyanocyclopropyl | | |

TABLE 1-continued

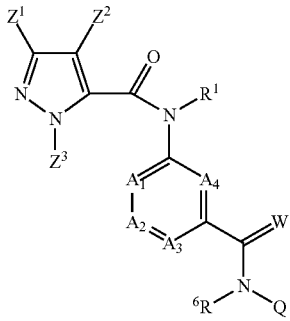

(I-1)

| Ex. No | $Z^1$ | $Z^2$ | $Z^3$ | $R^1$ | $A^1$ | $A^2$ | $A^3$ | $A^4$ | W | $R^6$ | Q | logP | Mass [m/z] 1 |
|---|---|---|---|---|---|---|---|---|---|---|---|---|---|
| 91 | pentafluoroethyl | $CF_3$ | Me | H | CH | CH | CF | CH | S | H | 1-cyanocyclopropyl | | |
| 92 | pentafluoroethyl | $CF_3$ | Me | 4-chlorobenzyl | CH | CH | CCl | CH | S | H | 1-cyanocyclopropyl | | |
| 93 | pentafluoroethyl | $CF_3$ | Me | isobutyryl | CH | CH | CCl | CH | S | H | 1-cyanocyclopropyl | | |
| 94 | pentafluoroethyl | $CF_3$ | Me | but-2-yn-1-yl | CH | CH | CCl | CH | S | H | 1-cyanocyclopropyl | | |
| 95 | pentafluoroethyl | $CF_3$ | Me | benzyl | CH | CH | CCl | CH | S | H | 1-cyanocyclopropyl | | |
| 96 | pentafluoroethyl | $CF_3$ | Me | pyridin-2-ylmethyl | CH | CH | CCl | CH | S | H | 1-cyanocyclopropyl | | |
| 97 | pentafluoroethyl | $CF_3$ | Me | propionyl | CH | CH | CCl | CH | S | H | 1-cyanocyclopropyl | | |
| 98 | pentafluoroethyl | $CF_3$ | Et | H | CH | CH | CCl | CH | S | H | 1-cyanocyclopropyl | | |
| 99 | pentafluoroethyl | $CF_3$ | Pr | H | CH | CH | CCl | CH | S | H | 1-cyanocyclopropyl | | |
| 100 | pentafluoroethyl | $CF_3$ | Pr | H | CH | CH | CF | CH | S | H | 1-cyanocyclopropyl | | |
| 101 | pentafluoroethyl | $CF_3$ | Et | H | CH | CH | CF | CH | S | H | 1-cyanocyclopropyl | | |
| 102 | pentafluoroethyl | $CF_3$ | Et | Me | CH | CH | CCl | CH | S | H | 1-cyanocyclopropyl | | |
| 103 | pentafluoroethyl | $CF_3$ | Me | Et | CH | CBr | CCl | CH | S | H | 1-cyanocyclopropyl | | |
| 104 | pentafluoroethyl | $CF_3$ | Me | H | CH | CH | CCl | CH | S | acetyl | 1-cyanocyclopropyl | | |
| 105 | pentafluoroethyl | $CF_3$ | Et | Me | CH | CH | CCl | CH | S | Me | 1-cyanocyclopropyl | | |
| 106 | pentafluoroethyl | methylsulphanyl | Me | H | CH | CH | CCl | CH | S | H | 1-cyanocyclopropyl | | |
| 107 | pentafluoroethyl | $CF_3$ | Et | Et | CH | CH | CCl | CH | S | H | 1-cyanocyclopropyl | | |
| 108 | pentafluoroethyl | $CF_3$ | Me | cyanomethyl | CH | CH | CCl | CH | S | H | 1-cyanocyclopropyl | | |
| 109 | pentafluoroethyl | methylsulphinyl | Me | H | CH | CH | CCl | CH | S | H | 1-cyanocyclopropyl | | |
| 110 | pentafluoroethyl | $CF_3$ | Pr | Me | CH | CH | CCl | CH | S | Me | 1-cyanocyclopropyl | | |
| 111 | pentafluoroethyl | $CF_3$ | Pr | Me | CH | CH | CF | CH | S | Me | 1-cyanocyclopropyl | | |
| 112 | pentafluoroethyl | $CF_3$ | Et | Me | CH | CH | CF | CH | S | H | 1-cyanocyclopropyl | | |
| 113 | pentafluoroethyl | methylsulphonyl | Me | H | CH | CH | CCl | CH | S | H | 1-cyanocyclopropyl | | |
| 114 | pentafluoroethyl | $CF_3$ | Pr | Et | CH | CH | CCl | CH | S | H | 1-cyanocyclopropyl | | |
| 115 | pentafluoroethyl | $CF_3$ | Pr | Et | CH | CH | CCl | CH | S | Et | 1-cyanocyclopropyl | | |
| 116 | pentafluoroethyl | $CF_3$ | Et | Et | CH | CH | CCl | CH | S | Et | 1-cyanocyclopropyl | | |
| 117 | pentafluoroethyl | $CF_3$ | Me | acetyl | CH | CH | CCl | CH | S | H | 1-cyanocyclopropyl | | |
| 118 | pentafluoroethyl | $CF_3$ | Me | pyridin-3-ylmethyl | CH | CH | CCl | CH | S | H | 1-cyanocyclopropyl | | |
| 119 | pentafluoroethyl | $CF_3$ | Me | 2-methylprop-2-en-1-yl | CH | CH | CCl | CH | S | H | 1-cyanocyclopropyl | | |
| 120 | pentafluoroethyl | $CF_3$ | Me | pyridin-4-ylmethyl | CH | CH | CCl | CH | S | H | 1-cyanocyclopropyl | | |

TABLE 1-continued

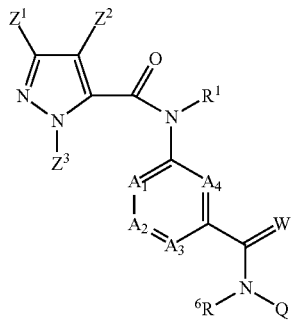

(I-1)

| Ex. No | $Z^1$ | $Z^2$ | $Z^3$ | $R^1$ | $A^1$ | $A^2$ | $A^3$ | $A^4$ | W | $R^6$ | Q | logP | Mass [m/z] 1 |
|---|---|---|---|---|---|---|---|---|---|---|---|---|---|
| 121 | penta-fluoroethyl | $CF_3$ | prop-2-yn-1-yl | H | CH | CH | CCl | CH | S | H | 1-cyano-cyclopropyl | | |
| 122 | penta-fluoroethyl | $CF_3$ | prop-2-en-1-yl | H | CH | CH | CCl | CH | S | H | 1-cyano-cyclopropyl | | |
| 123 | penta-fluoroethyl | $CF_3$ | Me | H | CH | CF | CBr | CH | S | H | 1-cyano-cyclopropyl | | |
| 124 | penta-fluoroethyl | $CF_3$ | Me | propionyl | CH | CH | CCl | CH | S | propionyl | 1-cyano-cyclopropyl | | |
| 125 | penta-fluoroethyl | $CF_3$ | Me | H | CH | CH | CCl | CH | S | Et | 1-cyano-cyclopropyl | | |
| 126 | penta-fluoroethyl | $CF_3$ | Me | H | CH | CH | CCl | CH | S | Me | 1-cyano-cyclopropyl | | |
| 127 | penta-fluoroethyl | $CF_3$ | Me | isopropoxy-carbonyl | CH | CH | CCl | CH | S | H | 1-cyano-cyclopropyl | | |
| 128 | penta-fluoroethyl | $CF_3$ | 2,2,2-tri-fluoroethyl | H | CH | CH | CCl | CH | S | H | 1-cyano-cyclopropyl | | |

TABLE 2

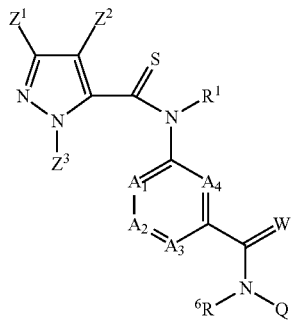

(Ib)

| Ex. No | $Z^1$ | $Z^2$ | $Z^3$ | $R^1$ | $A^1$ | $A^2$ | $A^3$ | $A^4$ | W | $R^6$ | Q | logP | Mass [m/z] 1 |
|---|---|---|---|---|---|---|---|---|---|---|---|---|---|
| 129 | 1-fluoro-cyclopropyl | Br | Me | H | CH | CH | CCl | CH | O | H | 1-cyano-cyclopropyl | | |
| 130 | $CF_3$ | $CF_3$ | Me | Me | CH | CH | CCl | CH | O | H | 1-cyano-cyclopropyl | | |
| 131 | 1-chloro-cyclopropyl | Cl | Me | Me | CH | CH | CCl | CH | O | H | 1-cyano-cyclopropyl | | |
| 132 | penta-fluoroethyl | $CF_3$ | Me | Me | CH | CH | CCl | CH | O | Et | 1-cyano-cyclopropyl | | |
| 133 | penta-fluoroethyl | $CF_3$ | Me | Me | CH | CH | CCl | CH | O | Me | 1-cyano-cyclopropyl | | |
| 134 | penta-fluoroethyl | $CF_3$ | Me | Et | CH | CH | CCl | CH | O | H | 1-cyano-cyclopropyl | | |
| 135 | penta-fluoroethyl | $CF_3$ | Me | H | CH | CH | CCl | CH | O | H | 1-cyano-cyclobutyl | | |
| 136 | penta-fluoroethyl | $CF_3$ | Me | Me | CH | CH | CCl | CH | O | H | 1-cyano-cyclopropyl | | |
| 137 | $CF_3$ | $CF_3$ | Me | H | CH | CH | CCl | CH | O | H | 1-cyano-cyclopropyl | | |

TABLE 2-continued

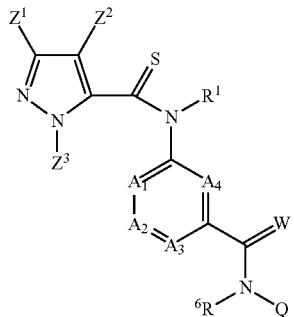

(Ib)

| Ex. No | $Z^1$ | $Z^2$ | $Z^3$ | $R^1$ | $A^1$ | $A^2$ | $A^3$ | $A^4$ | W | $R^6$ | Q | logP | Mass [m/z] 1 |
|---|---|---|---|---|---|---|---|---|---|---|---|---|---|
| 138 | pentafluoroethyl | $CF_3$ | Me | H | CH | CH | CCl | CH | O | H | 1-cyanocyclopropyl | | |
| 139 | $CF_3$ | $CF_3$ | Me | H | CH | CBr | CBr | CH | O | H | 1-cyanocyclopropyl | | |
| 140 | $CF_3$ | $CF_3$ | Me | H | CH | CCl | CBr | CH | O | H | 1-cyanocyclopropyl | | |
| 141 | pentafluoroethyl | $CF_3$ | Me | H | CH | CBr | CCl | CH | O | H | 1-cyanocyclopropyl | | |
| 142 | pentafluoroethyl | $CF_3$ | Me | H | CH | CH | CBr | CH | O | H | 1-cyanocyclopropyl | | |
| 143 | pentafluoroethyl | $CF_3$ | Me | H | CH | CH | CCl | CH | O | propionyl | 1-cyanocyclopropyl | | |
| 144 | pentafluoroethyl | $CF_3$ | Me | H | CH | CCl | CBr | CH | O | H | 1-cyanocyclopropyl | | |
| 145 | 1-fluorocyclopropyl | Cl | Me | H | CH | CH | CCl | CH | O | H | 1-cyanocyclopropyl | | |
| 146 | pentafluoroethyl | $CF_3$ | Me | acetyl | CH | CH | CCl | CH | O | acetyl | 1-cyanocyclopropyl | | |
| 147 | pentafluoroethyl | $CF_3$ | Me | methoxycarbonyl | CH | CH | CCl | CH | O | H | 1-cyanocyclopropyl | | |
| 148 | pentafluoroethyl | $CF_3$ | Me | ethoxycarbonyl | CH | CH | CCl | CH | O | H | 1-cyanocyclopropyl | | |
| 149 | pentafluoroethyl | $CF_3$ | Me | methoxycarbonyl | CH | CH | CCl | CH | O | methoxycarbonyl | 1-cyanocyclopropyl | | |
| 150 | pentafluoroethyl | $CF_3$ | Me | ethoxycarbonyl | CH | CH | CCl | CH | O | ethoxycarbonyl | 1-cyanocyclopropyl | | |
| 151 | pentafluoroethyl | $CF_3$ | Me | 2,2-dimethyl-propanoyl | CH | CH | CCl | CH | O | H | 1-cyanocyclopropyl | | |
| 152 | pentafluoroethyl | $CF_3$ | Me | H | CH | CMe | CCl | CH | O | H | 1-cyanocyclopropyl | | |
| 153 | pentafluoroethyl | $CF_3$ | Me | H | CH | CH | Cl | CH | O | H | 1-cyanocyclopropyl | | |
| 154 | pentafluoroethyl | $CF_3$ | Me | prop-2-yn-1-yl | CH | CH | CCl | CH | O | H | 1-cyanocyclopropyl | | |
| 155 | pentafluoroethyl | $CF_3$ | Me | H | CH | CH | CF | CH | O | H | 1-cyanocyclopropyl | | |
| 156 | pentafluoroethyl | $CF_3$ | Me | 4-chlorobenzyl | CH | CH | CCl | CH | O | H | 1-cyanocyclopropyl | | |
| 157 | pentafluoroethyl | $CF_3$ | Me | isobutyryl | CH | CH | CCl | CH | O | H | 1-cyanocyclopropyl | | |
| 158 | pentafluoroethyl | $CF_3$ | Me | but-2-yn-1-yl | CH | CH | CCl | CH | O | H | 1-cyanocyclopropyl | | |
| 159 | pentafluoroethyl | $CF_3$ | Me | benzyl | CH | CH | CCl | CH | O | H | 1-cyanocyclopropyl | | |
| 160 | pentafluoroethyl | $CF_3$ | Me | pyridin-2-ylmethyl | CH | CH | CCl | CH | O | H | 1-cyanocyclopropyl | | |
| 161 | pentafluoroethyl | $CF_3$ | Me | propionyl | CH | CH | CCl | CH | O | H | 1-cyanocyclopropyl | | |
| 162 | pentafluoroethyl | $CF_3$ | Et | H | CH | CH | CCl | CH | O | H | 1-cyanocyclopropyl | | |
| 163 | pentafluoroethyl | $CF_3$ | Pr | H | CH | CH | CCl | CH | O | H | 1-cyanocyclopropyl | | |
| 164 | pentafluoroethyl | $CF_3$ | Pr | H | CH | CH | CF | CH | O | H | 1-cyanocyclopropyl | | |
| 165 | pentafluoroethyl | $CF_3$ | Et | H | CH | CH | CF | CH | O | H | 1-cyanocyclopropyl | | |
| 166 | pentafluoroethyl | $CF_3$ | Et | Me | CH | CH | CCl | CH | O | H | 1-cyanocyclopropyl | | |
| 167 | pentafluoroethyl | $CF_3$ | Me | Et | CH | CBr | CCl | CH | O | H | 1-cyanocyclopropyl | | |

TABLE 2-continued

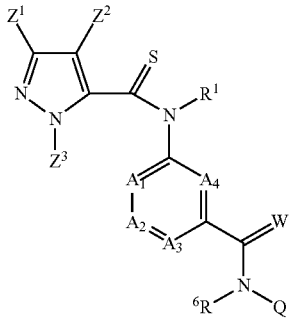

(Ib)

| Ex. No | $Z^1$ | $Z^2$ | $Z^3$ | $R^1$ | $A^1$ | $A^2$ | $A^3$ | $A^4$ | W | $R^6$ | Q | logP | Mass [m/z] 1 |
|---|---|---|---|---|---|---|---|---|---|---|---|---|---|
| 168 | pentafluoroethyl | $CF_3$ | Me | H | CH | CH | CCl | CH | O | acetyl | 1-cyanocyclopropyl | | |
| 169 | pentafluoroethyl | $CF_3$ | Et | Me | CH | CH | CCl | CH | O | Me | 1-cyanocyclopropyl | | |
| 170 | pentafluoroethyl | methylsulphanyl | Me | H | CH | CH | CCl | CH | O | H | 1-cyanocyclopropyl | | |
| 171 | pentafluoroethyl | $CF_3$ | Et | Et | CH | CH | CCl | CH | O | H | 1-cyanocyclopropyl | | |
| 172 | pentafluoroethyl | $CF_3$ | Me | cyanomethyl | CH | CH | CCl | CH | O | H | 1-cyanocyclopropyl | | |
| 173 | pentafluoroethyl | methylsulphinyl | Me | H | CH | CH | CCl | CH | O | H | 1-cyanocyclopropyl | | |
| 174 | pentafluoroethyl | $CF_3$ | Pr | Me | CH | CH | CCl | CH | O | Me | 1-cyanocyclopropyl | | |
| 175 | pentafluoroethyl | $CF_3$ | Pr | Me | CH | CH | CF | CH | O | Me | 1-cyanocyclopropyl | | |
| 176 | pentafluoroethyl | $CF_3$ | Et | Me | CH | CH | CF | CH | O | H | 1-cyanocyclopropyl | | |
| 177 | pentafluoroethyl | methylsulphonyl | Me | H | CH | CH | CCl | CH | O | H | 1-cyanocyclopropyl | | |
| 178 | pentafluoroethyl | $CF_3$ | Pr | Et | CH | CH | CCl | CH | O | H | 1-cyanocyclopropyl | | |
| 179 | pentafluoroethyl | $CF_3$ | Pr | Et | CH | CH | CCl | CH | O | Et | 1-cyanocyclopropyl | | |
| 180 | pentafluoroethyl | $CF_3$ | Et | Et | CH | CH | CCl | CH | O | Et | 1-cyanocyclopropyl | | |
| 181 | pentafluoroethyl | $CF_3$ | Me | acetyl | CH | CH | CCl | CH | O | H | 1-cyanocyclopropyl | | |
| 182 | pentafluoroethyl | $CF_3$ | Me | pyridin-3-ylmethyl | CH | CH | CCl | CH | O | H | 1-cyanocyclopropyl | | |
| 183 | pentafluoroethyl | $CF_3$ | Me | 2-methylprop-2-en-1-yl | CH | CH | CCl | CH | O | H | 1-cyanocyclopropyl | | |
| 184 | pentafluoroethyl | $CF_3$ | Me | pyridin-4-ylmethyl | CH | CH | CCl | CH | O | H | 1-cyanocyclopropyl | | |
| 185 | pentafluoroethyl | $CF_3$ | prop-2-yn-1-yl | H | CH | CH | CCl | CH | O | H | 1-cyanocyclopropyl | | |
| 186 | pentafluoroethyl | $CF_3$ | prop-2-en-1-yl | H | CH | CH | CCl | CH | O | H | 1-cyanocyclopropyl | | |
| 187 | pentafluoroethyl | $CF_3$ | Me | H | CH | CF | CBr | CH | O | H | 1-cyanocyclopropyl | | |
| 188 | pentafluoroethyl | $CF_3$ | Me | propionyl | CH | CH | CCl | CH | O | propionyl | 1-cyanocyclopropyl | | |
| 189 | pentafluoroethyl | $CF_3$ | Me | H | CH | CH | CCl | CH | O | Et | 1-cyanocyclopropyl | | |
| 190 | pentafluoroethyl | $CF_3$ | Me | H | CH | CH | CCl | CH | O | Me | 1-cyanocyclopropyl | | |
| 191 | pentafluoroethyl | $CF_3$ | Me | isopropoxycarbonyl | CH | CH | CCl | CH | O | H | 1-cyanocyclopropyl | | |
| 192 | pentafluoroethyl | $CF_3$ | 2,2,2-trifluoroethyl | H | CH | CH | CCl | CH | O | H | 1-cyanocyclopropyl | | |
| 193 | $CF_3$ | $CF_3$ | Me | H | CH | CH | CCl | CH | S | H | 1-cyanocyclopropyl | | |
| 194 | pentafluoroethyl | $CF_3$ | Me | Me | CH | CH | CCl | CH | S | H | 1-cyanocyclopropyl | | |
| 195 | pentafluoroethyl | $CF_3$ | Me | H | CH | CH | CCl | CH | S | H | 1-cyanocyclobutyl | | |
| 196 | pentafluoroethyl | $CF_3$ | Me | Et | CH | CH | CCl | CH | S | H | 1-cyanocyclopropyl | | |

TABLE 2-continued

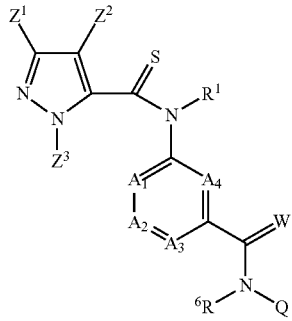

(Ib)

| Ex. No | $Z^1$ | $Z^2$ | $Z^3$ | $R^1$ | $A^1$ | $A^2$ | $A^3$ | $A^4$ | W | $R^6$ | Q | logP | Mass [m/z] 1 |
|---|---|---|---|---|---|---|---|---|---|---|---|---|---|
| 197 | pentafluoroethyl | $CF_3$ | Me | Me | CH | CH | CCl | CH | S | Me | 1-cyanocyclopropyl | | |
| 198 | pentafluoroethyl | $CF_3$ | Me | Me | CH | CH | CCl | CH | S | Et | 1-cyanocyclopropyl | | |
| 199 | 1-chlorocyclopropyl | Cl | Me | Me | CH | CH | CCl | CH | S | H | 1-cyanocyclopropyl | | |
| 200 | $CF_3$ | $CF_3$ | Me | Me | CH | CH | CCl | CH | S | H | 1-cyanocyclopropyl | | |
| 201 | pentafluoroethyl | $CF_3$ | Me | H | CH | CH | CCl | CH | S | H | 1-cyanocyclopropyl | | |
| 202 | 1-fluorocyclopropyl | Br | Me | H | CH | CH | CCl | CH | S | H | 1-cyanocyclopropyl | | |
| 203 | $CF_3$ | $CF_3$ | Me | H | CH | CBr | CBr | CH | S | H | 1-cyanocyclopropyl | | |
| 204 | $CF_3$ | $CF_3$ | Me | H | CH | CCl | CBr | CH | S | H | 1-cyanocyclopropyl | | |
| 205 | pentafluoroethyl | $CF_3$ | Me | H | CH | CBr | CCl | CH | S | H | 1-cyanocyclopropyl | | |
| 206 | pentafluoroethyl | $CF_3$ | Me | H | CH | CH | CBr | CH | S | H | 1-cyanocyclopropyl | | |
| 207 | pentafluoroethyl | $CF_3$ | Me | H | CH | CH | CCl | CH | S | propionyl | 1-cyanocyclopropyl | | |
| 208 | pentafluoroethyl | $CF_3$ | Me | H | CH | CCl | CBr | CH | S | H | 1-cyanocyclopropyl | | |
| 209 | 1-fluorocyclopropyl | Cl | Me | H | CH | CH | CCl | CH | S | H | 1-cyanocyclopropyl | | |
| 210 | pentafluoroethyl | $CF_3$ | Me | acetyl | CH | CH | CCl | CH | S | acetyl | 1-cyanocyclopropyl | | |
| 211 | pentafluoroethyl | $CF_3$ | Me | methoxycarbonyl | CH | CH | CCl | CH | S | H | 1-cyanocyclopropyl | | |
| 212 | pentafluoroethyl | $CF_3$ | Me | ethoxycarbonyl | CH | CH | CCl | CH | S | H | 1-cyanocyclopropyl | | |
| 213 | pentafluoroethyl | $CF_3$ | Me | methoxycarbonyl | CH | CH | CCl | CH | S | methoxycarbonyl | 1-cyanocyclopropyl | | |
| 214 | pentafluoroethyl | $CF_3$ | Me | ethoxycarbonyl | CH | CH | CCl | CH | S | ethoxycarbonyl | 1-cyanocyclopropyl | | |
| 215 | pentafluoroethyl | $CF_3$ | Me | 2,2-dimethylpropanoyl | CH | CH | CCl | CH | S | H | 1-cyanocyclopropyl | | |
| 216 | pentafluoroethyl | $CF_3$ | Me | H | CH | CMe | CCl | CH | S | H | 1-cyanocyclopropyl | | |
| 217 | pentafluoroethyl | $CF_3$ | Me | H | CH | CH | Cl | CH | S | H | 1-cyanocyclopropyl | | |
| 218 | pentafluoroethyl | $CF_3$ | Me | prop-2-yn-1-yl | CH | CH | CCl | CH | S | H | 1-cyanocyclopropyl | | |
| 219 | pentafluoroethyl | $CF_3$ | Me | H | CH | CH | CF | CH | S | H | 1-cyanocyclopropyl | | |
| 220 | pentafluoroethyl | $CF_3$ | Me | 4-chlorobenzyl | CH | CH | CCl | CH | S | H | 1-cyanocyclopropyl | | |
| 221 | pentafluoroethyl | $CF_3$ | Me | isobutyryl | CH | CH | CCl | CH | S | H | 1-cyanocyclopropyl | | |
| 222 | pentafluoroethyl | $CF_3$ | Me | but-2-yn-1-yl | CH | CH | CCl | CH | S | H | 1-cyanocyclopropyl | | |
| 223 | pentafluoroethyl | $CF_3$ | Me | benzyl | CH | CH | CCl | CH | S | H | 1-cyanocyclopropyl | | |
| 224 | pentafluoroethyl | $CF_3$ | Me | pyridin-2-ylmethyl | CH | CH | CCl | CH | S | H | 1-cyanocyclopropyl | | |
| 225 | pentafluoroethyl | $CF_3$ | Me | propionyl | CH | CH | CCl | CH | S | H | 1-cyanocyclopropyl | | |
| 226 | pentafluoroethyl | $CF_3$ | Et | H | CH | CH | CCl | CH | S | H | 1-cyanocyclopropyl | | |

TABLE 2-continued (Ib)

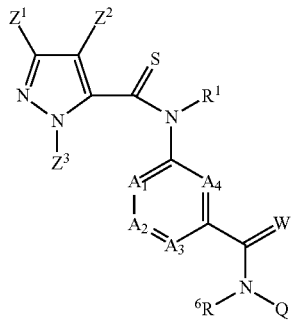

| Ex. No | $Z^1$ | $Z^2$ | $Z^3$ | $R^1$ | $A^1$ | $A^2$ | $A^3$ | $A^4$ | W | $R^6$ | Q | logP | Mass [m/z] 1 |
|---|---|---|---|---|---|---|---|---|---|---|---|---|---|
| 227 | pentafluoroethyl | CF$_3$ | Pr | H | CH | CH | CCl | CH | S | H | 1-cyanocyclopropyl | | |
| 228 | pentafluoroethyl | CF$_3$ | Pr | H | CH | CH | CF | CH | S | H | 1-cyanocyclopropyl | | |
| 229 | pentafluoroethyl | CF$_3$ | Et | H | CH | CH | CF | CH | S | H | 1-cyanocyclopropyl | | |
| 230 | pentafluoroethyl | CF$_3$ | Et | Me | CH | CH | CCl | CH | S | H | 1-cyanocyclopropyl | | |
| 231 | pentafluoroethyl | CF$_3$ | Me | Et | CH | CBr | CCl | CH | S | H | 1-cyanocyclopropyl | | |
| 232 | pentafluoroethyl | CF$_3$ | Me | H | CH | CH | CCl | CH | S | acetyl | 1-cyanocyclopropyl | | |
| 233 | pentafluoroethyl | CF$_3$ | Et | Me | CH | CH | CCl | CH | S | Me | 1-cyanocyclopropyl | | |
| 234 | pentafluoroethyl | methylsulphanyl | Me | H | CH | CH | CCl | CH | S | H | 1-cyanocyclopropyl | | |
| 235 | pentafluoroethyl | CF$_3$ | Et | Et | CH | CH | CCl | CH | S | H | 1-cyanocyclopropyl | | |
| 236 | pentafluoroethyl | CF$_3$ | Me | cyanomethyl | CH | CH | CCl | CH | S | H | 1-cyanocyclopropyl | | |
| 237 | pentafluoroethyl | methylsulphinyl | Me | H | CH | CH | CCl | CH | S | H | 1-cyanocyclopropyl | | |
| 238 | pentafluoroethyl | CF$_3$ | Pr | Me | CH | CH | CCl | CH | S | Me | 1-cyanocyclopropyl | | |
| 239 | pentafluoroethyl | CF$_3$ | Pr | Me | CH | CH | CF | CH | S | Me | 1-cyanocyclopropyl | | |
| 240 | pentafluoroethyl | CF$_3$ | Et | Me | CH | CH | CF | CH | S | H | 1-cyanocyclopropyl | | |
| 241 | pentafluoroethyl | methylsulphonyl | Me | H | CH | CH | CCl | CH | S | H | 1-cyanocyclopropyl | | |
| 242 | pentafluoroethyl | CF$_3$ | Pr | Et | CH | CH | CCl | CH | S | H | 1-cyanocyclopropyl | | |
| 243 | pentafluoroethyl | CF$_3$ | Pr | Et | CH | CH | CCl | CH | S | Et | 1-cyanocyclopropyl | | |
| 244 | pentafluoroethyl | CF$_3$ | Et | Et | CH | CH | CCl | CH | S | Et | 1-cyanocyclopropyl | | |
| 245 | pentafluoroethyl | CF$_3$ | Me | acetyl | CH | CH | CCl | CH | S | H | 1-cyanocyclopropyl | | |
| 246 | pentafluoroethyl | CF$_3$ | Me | pyridin-3-ylmethyl | CH | CH | CCl | CH | S | H | 1-cyanocyclopropyl | | |
| 247 | pentafluoroethyl | CF$_3$ | Me | 2-methylprop-2-en-1-yl | CH | CH | CCl | CH | S | H | 1-cyanocyclopropyl | | |
| 248 | pentafluoroethyl | CF$_3$ | Me | pyridin-4-ylmethyl | CH | CH | CCl | CH | S | H | 1-cyanocyclopropyl | | |
| 249 | pentafluoroethyl | CF$_3$ | prop-2-yn-1-yl | H | CH | CH | CCl | CH | S | H | 1-cyanocyclopropyl | | |
| 250 | pentafluoroethyl | CF$_3$ | prop-2-en-1-yl | H | CH | CH | CCl | CH | S | H | 1-cyanocyclopropyl | | |
| 251 | pentafluoroethyl | CF$_3$ | Me | H | CH | CF | CBr | CH | S | H | 1-cyanocyclopropyl | | |
| 252 | pentafluoroethyl | CF$_3$ | Me | propionyl | CH | CH | CCl | CH | S | propionyl | 1-cyanocyclopropyl | | |
| 253 | pentafluoroethyl | CF$_3$ | Me | H | CH | CH | CCl | CH | S | Et | 1-cyanocyclopropyl | | |
| 254 | pentafluoroethyl- | CF$_3$ | Me | H | CH | CH | CCl | CH | S | Me | 1-cyanocyclopropyl | | |
| 255 | pentafluoroethyl | CF$_3$ | Me | isopropoxycarbonyl | CH | CH | CCl | CH | S | H | 1-cyanocyclopropyl | | |

TABLE 2-continued

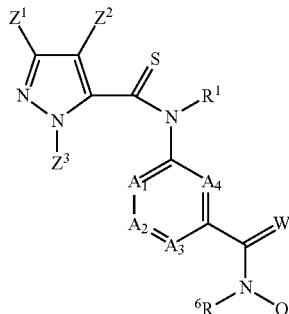

(Ib)

| Ex. No | $Z^1$ | $Z^2$ | $Z^3$ | $R^1$ | $A^1$ | $A^2$ | $A^3$ | $A^4$ | W | $R^6$ | Q | logP | Mass [m/z] 1 |
|---|---|---|---|---|---|---|---|---|---|---|---|---|---|
| 256 | penta-fluoroethyl | $CF_3$ | 2,2,2-tri-fluoro-ethyl | H | CH | CH | CCl | CH | S | H | 1-cyano-cyclopropyl | | |

The stated mass is the peak of the isotope pattern of the [M+H]$^+$ ion of the highest intensity; if the [M−H]$^−$ ion was detected, the stated mass is marked with $^2$.

$^2$ The stated mass is the peak of the isotope pattern of the [M−H]$^−$ ion of the highest intensity.

$^{a)}$ Note regarding the determination of the log P values and mass detection: The determination of the given log P values was carried out in accordance with EEC Directive 79/831 Annex V.A8 by HPLC (High Performance Liquid Chromatography) on a reversed-phase column (C18). Agilent 1100 LC system; 50*4.6 Zorbax Eclipse Plus C18 1.8 micron; mobile phase A: acetonitrile (0.1% formic acid); mobile phase B: water (0.09% formic acid); linear gradient from 10% acetonitrile to 95% acetonitrile in 4.25 min, then 95% acetonitrile for a further 1.25 min; oven temperature 55° C.; flow rate: 2.0 ml/min. Mass detection is via an Agilend MSD system.

$^{b)}$ Note regarding the determination of the log P values and mass detection: The stated log P values were determined in accordance with EEC Directive 79/831 Annex V.A8 by HPLC (High Performance Liquid Chromatography) using a reversed-phase column (C18). HP1100; 50*4.6 Zorbax Eclipse Plus C18 1.8 micron; mobile phase A: acetonitrile (0.1% formic acid); mobile phase B: water (0.08% formic acid); linear gradient from 5% acetonitrile to 95% acetonitrile in 1.70 min, then 95% acetonitrile for a further 1.00 min; oven temperature 55° C.; flow rate: 2.0 ml/min Mass detection is via the mass detector Micromass ZQ2000 from Waters.

NMR Data of Selected Examples

The $^1$H-NMR data of selected examples are stated in the form of $^1$H-NMR peak lists. For each signal peak, the δ-value in ppm and the signal intensity in brackets are listed.

Ex. 3, solvent: [DMSO], spectrometer: 600.13 MHz 11.2357 (5.81); 9.4015 (2.32); 7.9529 (0.33); 7.9112 (0.33); 7.6345 (0.34); 7.4603 (2.39); 7.3952 (0.42); 7.3764 (0.35); 7.3658 (0.38); 7.3009 (0.7); 7.2887 (0.72); 4.4308 (0.59); 4.4236 (0.6); 4.0461 (1.28); 4.0342 (3.7); 4.0223 (3.71); 4.0105 (1.26); 3.853 (0.6); 3.8474 (0.42); 3.8307 (0.44); 3.7989 (0.86); 3.788 (1.25); 3.7603 (10.68); 3.7331 (1.16); 3.726 (1.01); 3.7196 (0.75); 3.7116 (0.53); 3.7053 (0.33); 3.459 (0.59); 3.4058 (13.82); 3.3755 (1.92); 3.3496 (164.63); 3.3259 (1.89); 3.2237 (0.45); 2.8908 (2.26); 2.7309 (1.92); 2.6212 (0.39); 2.6184 (0.58); 2.6154 (0.72); 2.6125 (0.61); 2.5427 (1.49); 2.5244 (3.1); 2.5214 (3.56); 2.5182 (3.84); 2.5093 (28.51); 2.5064 (58.78); 2.5034 (80.56); 2.5004 (60.43); 2.4975 (29.82); 2.3903 (0.38); 2.3873 (0.5); 2.3843 (0.39); 2.2647 (0.57); 2.2538 (0.97); 2.2442 (0.58); 2.2423 (0.63); 2.0871 (0.62); 2.0233 (0.41); 2.0152 (0.44); 2.0134 (0.46); 1.9905 (16); 1.9096 (1.12); 1.851 (0.52); 1.8378 (0.99); 1.7685 (0.38); 1.7588 (0.55); 1.7475 (0.49); 1.7373 (0.4); 1.7288 (0.34); 1.7133 (0.34); 1.7077 (0.35); 1.6908 (0.37); 1.6852 (0.36); 1.6645 (0.89); 1.6546 (1.09); 1.6502 (1.34); 1.6452 (1.8); 1.6419 (1.74); 1.637 (1.45); 1.6253 (1.25); 1.6174 (0.98); 1.6101 (0.88); 1.5994 (5.38); 1.5901 (11.8); 1.5856 (12.84); 1.5767 (5.21); 1.55 (0.56); 1.4866 (0.63); 1.473 (0.68); 1.467 (0.7); 1.4621 (0.62); 1.4595 (0.61); 1.4523 (0.5); 1.4479 (0.41); 1.4361 (0.35); 1.3967 (1.99); 1.3471 (5.81); 1.2984 (1.34); 1.2782 (1.83); 1.2518 (6.83); 1.2423 (12.83); 1.2384 (14.34); 1.2293 (8.19); 1.2043 (2.47); 1.1864 (5.57); 1.1746 (9.7); 1.1627 (5.14); 1.1493 (0.89); 1.1396 (0.87); 1.1361 (0.62); 1.1312 (0.65); 1.1158 (0.53); 1.111 (0.55); 1.108 (0.57); 1.1022 (0.42); 1.0935 (0.51); 1.0875 (0.48); 1.0847 (0.45); 1.0749 (0.38); 1.0668 (0.41); 1.0552 (0.36); 0.8965 (0.36); 0.8891 (1.06); 0.8851 (0.68); 0.8808 (0.62); 0.8743 (0.76); 0.8695 (0.73); 0.8627 (0.7); 0.8536 (0.94); 0.8421 (0.6); 0.8361 (0.4); 0.8234 (0.34); −0.0001 (1.54)

Ex. 4, solvent: [DMSO], spectrometer: 399.95 MHz 19.9995 (0.35); 11.1852 (0.43); 7.6987 (0.97); 7.6759 (1.26); 7.5988 (1.74); 7.5752 (1.65); 7.4867 (2.1); 7.3938 (0.43); 7.3652 (0.84); 7.2019 (0.66); 5.7464 (4.97); 4.0662 (6.84); 4.0391 (1.88); 4.0214 (2.04); 3.9933 (16); 3.595 (0.77); 3.5647 (0.67); 3.4575 (11.78); 3.3059 (1902.13); 3.2823 (28.24); 3.251 (7.34); 3.1867 (1.32); 3.0111 (0.86); 2.9377 (0.79); 2.9232 (0.87); 2.8698 (1.22); 2.7378 (0.55); 2.6938 (0.68); 2.6741 (2.27); 2.6694 (2.78); 2.6647 (2.28); 2.5392 (5.5); 2.5089 (156.27); 2.5047 (278.63); 2.5003 (354.49); 2.496 (248.83); 2.3948 (0.32); 2.3317 (1.82); 2.327 (2.38); 2.0693 (1.78); 2.0088 (0.37); 1.9867 (5.95); 1.9077 (1.11); 1.7114 (5.17); 1.6397 (0.5); 1.5825 (0.5); 1.4849 (1.82);

1.3986 (7.92); 1.3522 (3.78); 1.2986 (3.52); 1.259 (3.75); 1.2366 (4.08); 1.2171 (1.92); 1.1981 (2.64); 1.1928 (3.24); 1.1751 (4.15); 1.1572 (2.51); 1.1005 (2.54); 0.8906 (0.33); 0.8673 (0.4); 0.8547 (0.48); −0.0002 (5.05)
Ex. 5, solvent: [DMSO], spectrometer: 601.6 MHz 7.7016 (0.47); 7.6872 (0.61); 7.646 (0.57); 7.6419 (0.64); 7.6063 (0.37); 7.6024 (0.36); 7.5921 (0.54); 7.5882 (0.56); 7.579 (0.6); 7.3776 (1.3); 7.3475 (0.34); 5.7617 (16); 4.0701 (2.56); 4.0607 (0.79); 4.0345 (0.58); 4.0227 (0.63); 4.0108 (0.48); 3.9904 (2.73); 3.4829 (0.66); 3.4608 (9.78); 3.4259 (0.46); 3.3469 (320.39); 3.3232 (1.5); 3.2777 (0.75); 3.2493 (2.86); 3.2349 (0.66); 3.1106 (0.9); 3.076 (0.68); 2.8649 (2.78); 2.6213 (0.57); 2.6183 (0.8); 2.6153 (0.97); 2.6122 (0.82); 2.6093 (0.59); 2.543 (0.42); 2.5246 (1.24); 2.5215 (1.51); 2.5184 (1.42); 2.5096 (29.65); 2.5066 (65.23); 2.5035 (89.35); 2.5005 (63.63); 2.4975 (28.79); 2.3908 (0.39); 2.3877 (0.55); 2.3847 (0.39); 2.0771 (1); 1.9902 (1.99); 1.6767 (1.95); 1.6734 (2.2); 1.424 (0.34); 1.2981 (0.62); 1.2582 (0.83); 1.2356 (0.77); 1.1865 (0.59); 1.1747 (1.16); 1.1629 (0.58); −0.0002 (5.52)
Ex. 6, solvent: [DMSO], spectrometer: 399.95 MHz 9.5105 (1.11); 9.37 (2.71); 7.6861 (0.89); 7.6648 (1.1); 7.6188 (1.04); 7.6126 (1.08); 7.5402 (2.64); 7.5188 (3.08); 7.5037 (0.69); 7.4974 (0.6); 7.4823 (0.53); 7.4761 (0.48); 7.4235 (2.42); 7.4171 (2.51); 7.2689 (1.57); 7.2623 (1.43); 7.2476 (1.35); 7.2409 (1.22); 4.1197 (0.76); 4.1021 (1.01); 4.0852 (1.27); 4.0686 (4.88); 4.0575 (1.57); 4.0496 (0.54); 4.0397 (3.72); 4.0219 (3.71); 4.0041 (1.27); 3.8782 (10.99); 3.835 (0.33); 3.817 (0.89); 3.7993 (1.08); 3.7824 (0.96); 3.7647 (0.74); 3.6837 (0.33); 3.6654 (0.43); 3.6475 (0.38); 3.5854 (0.39); 3.5673 (0.46); 3.5489 (0.39); 3.3007 (145.63); 3.2772 (2.79); 2.6695 (0.34); 2.5395 (0.82); 2.5225 (1.85); 2.5092 (19.84); 2.5049 (35.06); 2.5004 (44.17); 2.4961 (30.18); 2.4917 (14.34); 1.987 (16); 1.6127 (0.63); 1.6036 (1.61); 1.5987 (1.68); 1.5905 (3.88); 1.5832 (3.24); 1.57 (1.36); 1.3041 (0.63); 1.2906 (1.18); 1.2841 (1.18); 1.2696 (0.62); 1.2594 (0.5); 1.2375 (1.04); 1.2307 (1.64); 1.2171 (3.03); 1.2106 (3.03); 1.1931 (4.97); 1.1753 (9.03); 1.1575 (7.71); 1.1395 (7.05); 1.1216 (3.13); 0.962 (1.16); 0.9444 (2.37); 0.9267 (1.1); −0.0002 (4.85)
Ex. 7, solvent: [DMSO], spectrometer: 399.95 MHz 11.4754 (1.96); 9.5774 (3.66); 7.8103 (3.62); 7.804 (4.04); 7.7228 (1.61); 7.7165 (1.38); 7.701 (2.26); 7.6946 (2.08); 7.606 (3.39); 7.5841 (2.38); 4.0559 (1.18); 4.0345 (16); 4.0204 (3.51); 4.0025 (1.13); 3.3203 (18.4); 2.7184 (0.84); 2.7027 (1.21); 2.6977 (1.45); 2.6851 (1.56); 2.6827 (1.57); 2.6699 (2.11); 2.6503 (1.2); 2.5102 (14.26); 2.5059 (28.52); 2.5014 (37.33); 2.4969 (26.79); 2.4927 (12.96); 2.4835 (1.57); 2.4608 (2.15); 2.4525 (1.25); 2.4404 (1.55); 2.4316 (1.5); 2.4084 (0.97); 2.1036 (0.56); 2.0953 (0.6); 2.085 (1.52); 2.0732 (1.03); 2.0651 (2.45); 2.058 (1.57); 2.0451 (1.65); 2.0352 (0.77); 2.0288 (0.39); 2.0252 (0.41); 2.0196 (0.4); 1.9889 (13.81); 1.1925 (3.78); 1.1747 (7.53); 1.1569 (3.66); −0.0002 (0.53)
Ex. 8, solvent: [CD3CN], spectrometer: 399.95 MHz 7.6396 (0.36); 7.5867 (0.51); 7.5653 (0.89); 7.544 (0.65); 7.5381 (0.86); 7.5157 (0.67); 7.5093 (0.52); 7.4941 (0.53); 7.4875 (0.63); 7.4768 (0.79); 7.3968 (2.11); 7.3753 (2.53); 7.3065 (1.94); 7.2998 (2.09); 7.1716 (1.4); 7.1649 (1.32); 7.1502 (1.17); 7.1434 (1.07); 3.9903 (3.54); 3.8495 (10.24); 3.4568 (16); 3.2228 (4.6); 2.1412 (168.83); 2.1318 (2.24); 2.1187 (0.37); 2.1125 (0.33); 2.1063 (0.38); 1.9749 (1.26); 1.9632 (92.07); 1.9513 (18.04); 1.9451 (33.99); 1.9389 (49.06); 1.9328 (33.45); 1.9266 (16.89); 1.7909 (0.5); 1.5939 (0.45); 1.5781 (1.51); 1.5737 (1.53); 1.5637 (2.7); 1.5577 (3.02); 1.5476 (0.89); 1.5443 (0.86); 1.3605 (0.47); 1.3468 (0.97); 1.3398 (1.12); 1.3254 (0.39); 1.2938 (1.35); 1.2881 (1.36); 1.2837 (1.68); 1.2798 (2.1); 1.2733 (1.74); 1.2636 (1.03); −0.0002 (5.39)
Ex. 9, solvent: [CD3CN], spectrometer: 601.6 MHz 9.3097 (0.56); 7.77 (3.79); 7.7657 (4.14); 7.6801 (2.48); 7.6757 (2.25); 7.6656 (2.92); 7.6612 (2.72); 7.6146 (1.14); 7.4969 (4.24); 7.4825 (3.68); 3.981 (16); 2.1615 (181.62); 2.0874 (0.35); 2.0771 (1.5); 2.0604 (0.46); 2.0563 (0.85); 2.0522 (1.16); 2.048 (0.87); 2.044 (0.44); 1.9735 (2.01); 1.9659 (259.46); 1.9576 (3.22); 1.9536 (3.65); 1.9499 (74.77); 1.9457 (141.93); 1.9416 (218.7); 1.9375 (150.41); 1.9334 (73.06); 1.9287 (2.12); 1.9246 (0.98); 1.8507 (1.44); 1.8351 (0.43); 1.831 (0.84); 1.8269 (1.17); 1.8227 (0.83); 1.8186 (0.43); 1.5805 (1.94); 1.5707 (4.1); 1.5665 (4.32); 1.5572 (2.31); 1.351 (2.23); 1.3416 (4); 1.3375 (4.07); 1.3276 (1.81); 0.9112 (1.45); 0.0053 (0.53); −0.0002 (20.71); −0.0057 (0.61)
Ex. 10, solvent: [DMSO], spectrometer: 600.13 MHz 11.4592 (3.78); 9.4859 (4.45); 7.7721 (3.8); 7.7678 (4.24); 7.7112 (2.06); 7.7068 (1.78); 7.6966 (2.55); 7.6922 (2.36); 7.5881 (4.49); 7.5736 (3.69); 4.0356 (0.65); 4.0285 (16); 3.3215 (12.57); 2.5227 (0.37); 2.5196 (0.46); 2.5165 (0.45); 2.5077 (11.12); 2.5047 (24.25); 2.5017 (33.57); 2.4986 (24.06); 2.4956 (10.94); 1.989 (1.5); 1.6018 (1.64); 1.5924 (3.8); 1.5879 (4.14); 1.5789 (1.69); 1.2696 (1.81); 1.2604 (3.74); 1.256 (4.13); 1.2464 (1.5); 1.1871 (0.41); 1.1753 (0.83); 1.1634 (0.41); 0.0053 (0.46); −0.0001 (14.7); −0.0057 (0.44)
Ex. 11, solvent: [CD3CN], spectrometer: 601.6 MHz 9.4276 (0.94); 8.1604 (0.81); 8.1562 (0.84); 8.0909 (3.21); 8.0868 (3.24); 7.8499 (0.65); 7.8457 (0.65); 7.6042 (1.17); 7.5896 (3.34); 7.5855 (3.31); 3.99 (0.48); 3.9775 (16); 2.2102 (11.21); 2.0881 (0.39); 2.0779 (0.4); 2.0656 (0.66); 2.0611 (0.41); 2.057 (0.54); 2.0529 (0.65); 2.0486 (0.62); 2.048 (0.62); 2.0447 (0.36); 1.9732 (0.39); 1.9666 (16.06); 1.9584 (0.96); 1.9542 (1.36); 1.9506 (29.13); 1.9464 (53.99); 1.9423 (82.18); 1.9382 (57.22); 1.9341 (28.42); 1.9294 (1.09); 1.9253 (0.59); 1.8317 (0.39); 1.8276 (0.51); 1.8234 (0.37); 1.5826 (1.54); 1.5728 (3.25); 1.5686 (3.38); 1.5593 (1.89); 1.3599 (1.74); 1.3506 (3.08); 1.3464 (3.24); 1.3366 (1.49); 0.911 (0.48); −0.0002 (0.46)
Ex. 12, solvent: [CD3CN], spectrometer: 601.6 MHz 9.4577 (0.94); 7.9506 (3.67); 7.9465 (3.74); 7.6252 (1.29); 7.6178 (0.41); 7.5485 (3.85); 7.5444 (3.76); 5.4498 (1.24); 4.1225 (0.39); 3.9907 (0.48); 3.9784 (16); 2.2016 (26.81); 2.0656 (0.9); 2.0571 (0.36); 2.053 (0.47); 2.0479 (0.79); 1.9732 (1.48); 1.9668 (2.89); 1.9586 (0.78); 1.9572 (0.41); 1.9544 (1.17); 1.9507 (24.16); 1.9466 (45.51); 1.9424 (67.8); 1.9383 (46.53); 1.9342 (23.27); 1.9296 (0.68); 1.8277

(0.39); 1.5858 (1.78); 1.576 (3.73); 1.5718 (3.9); 1.5625 (2.15); 1.3635 (2.04); 1.3541 (3.59); 1.3499 (3.77); 1.3401 (1.77); 1.269 (0.34); 1.2159 (0.42); 1.2041 (0.83); 1.1922 (0.4); 0.911 (0.44)
Ex. 13, solvent: [CD3CN], spectrometer: 399.95 MHz 9.425 (1.09); 8.1057 (3.59); 8.0995 (3.63); 8.089 (0.38); 8.0828 (0.33); 7.9667 (0.34); 7.6477 (3.95); 7.6415 (4.02); 7.626 (1.54); 7.6058 (0.49); 7.5997 (0.42); 7.5882 (0.4); 7.582 (0.48); 7.4416 (0.5); 4.1118 (0.33); 4.0862 (1.68); 4.0683 (4.78); 4.0505 (4.77); 4.0327 (1.64); 3.9761 (16); 3.8931 (3.57); 2.1489 (347.53); 2.1318 (7.91); 2.1127 (2.21); 2.1065 (2.07); 2.1003 (1.56); 2.0941 (1.09); 2.0486 (0.56); 2.0434 (0.54); 1.9712 (32.63); 1.9634 (416.05); 1.9514 (67.15); 1.9453 (119.86); 1.9391 (167.42); 1.9329 (114.6); 1.9267 (58.47); 1.7911 (2.41); 1.7799 (0.49); 1.7737 (0.78); 1.7675 (1.01); 1.7614 (0.72); 1.7553 (0.42); 1.6282 (0.54); 1.6129 (1.02); 1.6069 (1.1); 1.604 (0.72); 1.5923 (0.84); 1.5869 (1.9); 1.5726 (4.35); 1.5656 (4.47); 1.5518 (2.49); 1.5116 (0.39); 1.3551 (2.45); 1.3413 (4.31); 1.3343 (4.21); 1.3295 (1.9); 1.3202 (2.1); 1.3078 (0.68); 1.2852 (0.55); 1.2708 (1.26); 1.2216 (6.04); 1.2038 (11.75); 1.1859 (5.85); 0.9117 (0.79); 0.008 (0.82); −0.0002 (18.6); −0.0085 (0.72)
Ex. 14, solvent: [DMSO], spectrometer: 601.6 MHz 11.475 (2.8); 9.482 (4.01); 7.7377 (4.18); 7.7332 (5.35); 7.7173 (3.05); 7.6669 (0.49); 7.6647 (0.45); 7.6299 (2.01); 7.6257 (1.86); 7.6155 (1.61); 7.6111 (1.54); 4.046 (0.85); 4.0342 (3.8); 4.0263 (16); 4.0225 (3.74); 4.0105 (0.89); 3.3858 (0.71); 3.3809 (1.58); 3.3784 (1.63); 3.3578 (1678.47); 3.3341 (3.39); 3.0116 (0.41); 2.8065 (0.44); 2.6184 (0.64); 2.6153 (0.91); 2.6123 (0.64); 2.543 (0.47); 2.5247 (1.22); 2.5216 (1.5); 2.5185 (1.46); 2.5097 (46.46); 2.5066 (102.74); 2.5036 (142.42); 2.5006 (100.14); 2.4975 (44.69); 2.3908 (0.62); 2.3877 (0.87); 2.3847 (0.62); 2.0764 (1.87); 1.99 (10.94); 1.6062 (1.8); 1.5968 (4.05); 1.5923 (4.48); 1.5834 (1.81); 1.3972 (8.53); 1.272 (1.92); 1.2628 (3.88); 1.2584 (4.36); 1.2489 (1.8); 1.1863 (2.99); 1.1745 (5.92); 1.1626 (2.92); 0.0053 (0.68); −0.0002 (22.51); −0.0058 (0.62)
Ex. 15, solvent: [CD3CN], spectrometer: 601.6 MHz 7.6736 (3.25); 7.6594 (3.63); 7.6529 (0.62); 7.6383 (0.67); 7.5026 (1.73); 7.476 (1.42); 7.4719 (1.04); 7.4618 (1.32); 7.4578 (1.01); 7.4501 (0.41); 7.4349 (0.37); 5.3097 (0.35); 5.2976 (0.39); 4.0762 (0.87); 4.0644 (2.65); 4.0525 (2.74); 4.0407 (0.93); 3.9757 (0.91); 3.9408 (5.26); 3.9313 (16); 2.8568 (0.62); 2.8452 (1.86); 2.8333 (1.86); 2.8212 (0.7); 2.5123 (0.35); 2.4998 (1.1); 2.4874 (1.07); 2.4749 (0.42); 2.2936 (1.21); 2.2824 (1.31); 2.2699 (0.62); 2.2265 (0.62); 2.2149 (0.61); 2.1802 (0.36); 2.1739 (0.55); 2.1673 (0.84); 2.1535 (644.37); 2.1294 (0.59); 2.1215 (0.48); 2.0601 (0.87); 2.0561 (1.51); 2.0519 (2.22); 2.0478 (1.52); 2.0437 (0.77); 1.9727 (12.69); 1.9656 (21.18); 1.9575 (11.83); 1.9534 (14.58); 1.9496 (147.5); 1.9454 (266.85); 1.9413 (402.32); 1.9372 (276.01); 1.9331 (137.69); 1.9244 (1.96); 1.8503 (0.47); 1.8347 (1.84); 1.8307 (2.73); 1.8266 (3.2); 1.8225 (2.22); 1.8184 (1.32); 1.7246 (0.62); 1.7188 (0.99); 1.7132 (0.82); 1.6902 (1.73); 1.6658 (1); 1.6361 (0.55); 1.6214 (0.44); 1.6159 (0.49); 1.5864 (0.66); 1.5822 (0.66); 1.5728 (0.47); 1.5666 (0.46); 1.5571 (0.39); 1.5334 (1.65); 1.5063 (1.02); 1.5029 (0.92); 1.4777 (0.65); 1.4659 (0.65); 1.3852 (0.49); 1.3515 (0.42); 1.3403 (1.5); 1.3284 (0.54); 1.2851 (2.14); 1.2701 (1.88); 1.2384 (0.36); 1.2227 (0.53); 1.2158 (4.13); 1.2039 (7.13); 1.1963 (1.02); 1.1921 (4.09); 1.1765 (0.52); 1.1568 (0.64); 1.1488 (1.95); 1.1363 (4.5); 1.1315 (0.55); 1.1238 (2.55); 1.1152 (0.75); 1.1112 (1.54); 1.1021 (0.47); 1.0987 (0.78); 1.0915 (6.22); 1.0797 (12.97); 1.0677 (6.14); 1.0509 (0.37); 1.0462 (0.5); 1.0418 (0.48); 1.0022 (0.57); 0.9849 (0.79); 0.9637 (0.69); 0.949 (4.67); 0.9431 (1.35); 0.9371 (10.26); 0.9313 (2.24); 0.9244 (5.69); 0.9194 (1.11); 0.9121 (1.74); 0.8817 (0.48); 0.0964 (0.45); 0.0053 (3.79); −0.0002 (131.79); −0.0058 (3.52); −0.1 (0.49)
Ex. 16, solvent: [DMSO], spectrometer: 601.6 MHz 11.6171 (2.98); 9.5642 (4.11); 8.0041 (4.64); 8.0001 (4.81); 7.5795 (3.62); 7.5754 (3.58); 4.377 (0.35); 4.3686 (0.7); 4.3601 (0.34); 4.0417 (16); 4.0342 (2.77); 4.0223 (2.5); 4.0105 (0.81); 3.9261 (1.01); 3.4494 (0.63); 3.4409 (0.64); 3.4378 (0.67); 3.4293 (0.66); 3.3467 (410.03); 3.3231 (3.18); 2.6178 (0.42); 2.6148 (0.6); 2.6118 (0.44); 2.5425 (0.44); 2.524 (1.29); 2.521 (1.64); 2.5178 (1.9); 2.509 (30.94); 2.5061 (65.8); 2.5031 (89.43); 2.5 (63.28); 2.497 (28.23); 2.3902 (0.42); 2.3872 (0.55); 2.3842 (0.39); 2.0769 (0.6); 1.99 (10.77); 1.9093 (0.47); 1.6161 (1.9); 1.6067 (4.15); 1.6022 (4.51); 1.5933 (1.81); 1.3972 (13.57); 1.3139 (0.32); 1.2846 (2.01); 1.2754 (3.98); 1.271 (4.39); 1.2614 (1.64); 1.1863 (2.93); 1.1745 (6.06); 1.1627 (2.93); 1.0665 (1.46); 1.0549 (2.75); 1.0433 (1.33); 0.0052 (0.71); −0.0002 (20.09); −0.0057 (0.51)
Ex. 17, solvent: [DMSO], spectrometer: 399.95 MHz 10.9164 (2.69); 9.4701 (3.13); 7.8379 (2.16); 7.8316 (2.46); 7.7664 (1.22); 7.76 (1.05); 7.7445 (1.48); 7.7381 (1.32); 7.5569 (3.32); 7.5351 (2.79); 5.7527 (16); 4.0382 (0.59); 4.0204 (0.58); 3.9311 (10.48); 3.9291 (10.23); 3.4476 (0.32); 3.4238 (0.79); 3.3995 (1.41); 3.3529 (444.16); 3.2649 (0.45); 2.6723 (0.35); 2.5255 (1.04); 2.5123 (20.85); 2.5078 (42.03); 2.5032 (55.95); 2.4986 (40.59); 2.4941 (19.88); 2.3299 (0.35); 2.0728 (0.88); 1.9887 (2.51); 1.6084 (1.2); 1.5942 (2.85); 1.5874 (2.99); 1.5741 (1.42); 1.4794 (0.54); 1.4586 (1.66); 1.4548 (1.64); 1.4399 (0.7); 1.4294 (0.58); 1.4133 (1.6); 1.4094 (1.68); 1.3975 (0.83); 1.3948 (0.79); 1.2663 (1.44); 1.2525 (2.82); 1.246 (3.04); 1.2314 (1.24); 1.1927 (0.77); 1.1749 (1.45); 1.1571 (0.71); 1.129 (0.6); 1.1124 (1.86); 1.1085 (2.26); 1.0923 (2.2); 1.0884 (1.8); 1.0706 (0.5)
Ex. 18, solvent: [DMSO], spectrometer: 601.6 MHz 7.8045 (2.23); 7.7904 (2.42); 7.6562 (0.38); 4.0456 (0.8); 4.0338 (2.39); 4.0304 (0.69); 4.0219 (3.08); 4.015 (16); 3.3608 (569.24); 3.3375 (3.07); 2.6187 (0.62); 2.6157 (0.85); 2.6127 (0.62); 2.5434 (0.54); 2.525 (1.66); 2.5219 (2.15); 2.5188 (2.4); 2.51 (45.96); 2.507 (97.64); 2.504 (134.23); 2.5009 (97.3); 2.4979 (44.27); 2.4056 (15.53); 2.3974 (1.27); 2.3945 (0.66); 2.3911 (0.88); 2.3882 (1.2); 2.3851 (0.77); 2.3823 (0.42); 2.2183 (1.21); 2.0872 (0.45); 2.0779 (2.65); 2.0487 (3.59); 2.0305 (0.77); 2.0256 (0.48); 1.9905 (10.01); 1.9538 (0.39); 1.9098 (4.41); 1.8867 (0.87); 1.8814 (0.87); 1.3969 (14.61); 1.2345 (0.46); 1.1862 (2.73); 1.1744 (5.37); 1.1653 (0.38); 1.1625 (2.65); −0.0002 (9.42)
Ex. 19, solvent: [DMSO], spectrometer: 399.95 MHz 9.6008 (2.87); 7.7336 (2.68); 7.7122 (3.27); 7.6828 (2.15); 7.6766 (2.25); 7.518 (1.37); 7.5117 (1.26); 7.4968 (1.12); 7.4904 (1.05); 4.066 (10.48); 4.0381 (0.83); 4.0203 (1.07); 4.0026 (0.33); 3.6767 (16);

3.487 (0.45); 3.4643 (0.44); 3.4467 (0.79); 3.4391 (0.81); 3.4231 (1.05); 3.4136 (1.13); 3.3468
(882.82); 3.3224 (20.56); 3.2828 (0.63); 2.6764 (0.54); 2.6718 (0.74); 2.6674 (0.52); 2.542 (0.61);
2.5249 (2.21); 2.5118 (42.56); 2.5073 (85.34); 2.5028 (113.7); 2.4982 (82.44); 2.4937 (40); 2.3341
(0.49); 2.3295 (0.72); 2.3249 (0.52); 2.0729 (3.68); 1.9886 (3.32); 1.6558 (0.33); 1.6144 (1.37); 1.6001
(2.7); 1.5932 (2.9); 1.5801 (1.41); 1.2938 (1.3); 1.2802 (2.57); 1.2735 (2.8); 1.2588 (1.33); 1.2356
(0.78); 1.1925 (0.98); 1.1748 (2); 1.1569 (1); 0.008 (1.05); −0.0002 (28.19); −0.0085 (1.08)
Ex. 20, solvent: [DMSO], spectrometer: 601.6 MHz 9.6087 (4.57); 7.7293 (4.27); 7.7152 (4.9); 7.6801 (2.65); 7.676 (2.67); 7.4972 (1.63); 7.493 (1.51);
7.4831 (1.43); 7.4788 (1.38); 4.3682 (0.58); 4.1597 (0.43); 4.1483 (1); 4.1369 (1.24); 4.1257 (1.28);
4.1143 (1); 4.1025 (0.47); 4.0779 (16); 4.0458 (0.46); 4.0339 (1.37); 4.0221 (1.98); 4.0103 (0.59);
3.449 (0.49); 3.4406 (0.49); 3.4374 (0.48); 3.429 (0.51); 3.3716 (1.66); 3.3457 (1847.32); 3.3222
(24.12); 2.6205 (0.63); 2.6176 (1.47); 2.6145 (2.05); 2.6115 (1.48); 2.6085 (0.63); 2.5422 (0.95);
2.5239 (2.46); 2.5208 (3.15); 2.5177 (3.1); 2.5088 (106.25); 2.5058 (238.45); 2.5028 (334.46); 2.4997
(242.59); 2.4967 (110.57); 2.393 (0.68); 2.39 (1.49); 2.3869 (2.09); 2.3839 (1.49); 2.3808 (0.69);
2.0766 (4.02); 1.9898 (5.37); 1.6109 (1.83); 1.6016 (3.88); 1.5971 (4.4); 1.5882 (2.19); 1.5763 (0.45);
1.2977 (0.37); 1.2859 (1.83); 1.2767 (3.71); 1.2723 (4.13); 1.2627 (1.75); 1.2579 (0.87); 1.2535 (1.01);
1.2499 (0.7); 1.2416 (1.16); 1.2342 (1.17); 1.23 (0.84); 1.1861 (1.54); 1.1742 (3.2); 1.1624 (1.62);
1.1496 (0.36); 1.0663 (1.12); 1.0546 (2); 1.043 (1.01); 0.9965 (6.51); 0.9847 (13.73); 0.973 (6.33);
0.0965 (0.41); 0.0053 (3.4); −0.0002 (125.56); −0.0058 (3.65); −0.1001 (0.45)
Ex. 21, solvent: [DMSO], spectrometer: 399.95 MHz 7.7082 (2.45); 7.6866 (3.64); 7.6836 (2.1); 7.6766 (1.8); 7.663 (0.46); 7.5662 (0.33); 7.5492 (1.41);
7.5429 (1.29); 7.5279 (1.11); 7.5216 (1.06); 4.0591 (10.46); 4.038 (1.4); 4.0203 (2.19); 4.0025 (0.48);
3.7168 (0.33); 3.679 (15.83); 3.6733 (4.07); 3.6676 (16); 3.4322 (0.35); 3.3435 (321.55); 3.3363
(458.6); 3.2717 (0.52); 3.1751 (0.88); 3.162 (0.79); 2.6807 (0.32); 2.676 (0.65); 2.6714 (0.93); 2.6667
(0.65); 2.5415 (0.74); 2.5246 (2.58); 2.5114 (50.63); 2.5069 (102.7); 2.5023 (137.44); 2.4977 (99.21);
2.4931 (48.14); 2.3337 (0.63); 2.3291 (0.88); 2.3244 (0.63); 2.0731 (1.7); 1.9885 (5.54); 1.9008 (1.74);
1.8954 (2.04); 1.6574 (0.47); 1.6142 (1.05); 1.5995 (1.75); 1.5933 (1.89); 1.2728 (0.35); 1.2585 (0.57);
1.2522 (0.48); 1.2358 (0.96); 1.1925 (1.64); 1.1747 (3.39); 1.1569 (1.68); −0.0002 (6.5)
Ex. 22, solvent: [DMSO], spectrometer: 601.6 MHz 7.7596 (0.35); 7.711 (3.38); 7.6968 (4.08); 7.6797 (1.48); 7.5444 (1.6); 7.5402 (1.49); 7.5303 (1.29);
7.526 (1.24); 4.3683 (0.44); 4.2593 (0.33); 4.2476 (0.33); 4.1566 (0.43); 4.1449 (0.94); 4.1332 (1.15);
4.1243 (1.15); 4.1129 (1.05); 4.1045 (0.75); 4.0946 (1.48); 4.0828 (3.99); 4.0686 (16); 4.0595 (1.27);
4.034 (0.45); 4.0221 (0.58); 4.0158 (0.43); 4.0103 (0.4); 3.449 (0.38); 3.4406 (0.38); 3.4374 (0.4);
3.429 (0.41); 3.3742 (1.02); 3.3457 (1563.22); 3.322 (28.53); 2.6206 (0.69); 2.6176 (1.46); 2.6146
(2.04); 2.6115 (1.44); 2.6085 (0.64); 2.5423 (1.22); 2.5239 (3.79); 2.5208 (5.05); 2.5176 (5.93); 2.5089
(109.54); 2.5059 (236.08); 2.5028 (323.23); 2.4997 (233.05); 2.4967 (103.3); 2.4766 (0.35); 2.3931
(0.66); 2.39 (1.43); 2.387 (2); 2.3839 (1.38); 2.3809 (0.63); 2.0767 (3.48); 1.9899 (1.42); 1.9031 (2.58);
1.6908 (0.35); 1.6696 (0.36); 1.6437 (0.33); 1.6184 (0.43); 1.5761 (1.67); 1.2579 (0.49); 1.2485 (0.35);
1.2344 (1.07); 1.2265 (0.65); 1.2146 (1.08); 1.2029 (0.52); 1.1861 (0.52); 1.1743 (1.03); 1.1705 (0.37);
1.1625 (0.52); 1.1492 (0.42); 1.0663 (0.87); 1.0547 (1.54); 1.043 (0.81); 1.0013 (6.44); 0.9895 (13.63);
0.9848 (1.07); 0.9817 (2.21); 0.9778 (6.34); 0.97 (0.97); 0.9557 (6.62); 0.9439 (14.2); 0.9321 (6.4);
0.0052 (3.03); −0.0002 (83.54); −0.0058 (2.47)
Ex. 23, solvent: [DMSO], spectrometer: 399.95 MHz 9.5605 (1.88); 7.757 (1.46); 7.7355 (1.78); 7.6605 (0.8); 7.545 (0.66); 7.5386 (0.61); 7.5238 (0.55);
7.5174 (0.52); 4.058 (1.05); 4.0402 (3.29); 4.0271 (6.99); 4.0225 (4.44); 4.0046 (1.09); 3.3924 (24.23);
3.386 (32.63); 3.3799 (54.59); 3.377 (71.91); 2.5111 (7.26); 2.5069 (9.99); 2.5034 (6.54); 1.9898
(14.31); 1.6154 (0.75); 1.6011 (1.63); 1.5941 (1.77); 1.5811 (0.79); 1.3053 (0.83); 1.2917 (1.6); 1.2849
(1.74); 1.2704 (0.67); 1.2049 (0.71); 1.1943 (4); 1.1765 (8.08); 1.1587 (3.94); 1.1133 (2.92); 1.012 (16);
−0.0002 (1.63)
Ex. 24, solvent: [DMSO], spectrometer: 399.95 MHz 19.0481 (0.34); 12.999 (0.34); 11.6718 (0.32); 11.3817 (2.98); 11.2103 (0.33); 10.7432 (0.44); 10.1704
(0.38); 9.4484 (4.12); 9.4182 (0.34); 7.674 (2.45); 7.6678 (2.75); 7.5767 (3.19); 7.5699 (2.9); 7.471
(0.33); 4.1638 (0.77); 4.0557 (0.89); 4.0379 (3.26); 4.0189 (16); 4.0023 (1.06); 3.9243 (2.59); 3.4462
(0.32); 3.409 (0.48); 3.3939 (0.61); 3.3326 (387.86); 3.3263 (665.26); 3.3027 (8.07); 2.675 (1.43);
2.6705 (2.09); 2.6661 (1.44); 2.5406 (0.85); 2.5238 (3.39); 2.5178 (218.8); 2.5017 (290.84); 2.4581
(0.39); 2.4169 (0.78); 2.3781 (14.51); 2.3549 (0.74); 2.3328 (1.45); 2.3283 (2.04); 2.3241 (1.4); 2.3115
(0.8); 2.2563 (0.65); 2.0733 (1.71); 1.9884 (10.86); 1.6699 (0.36); 1.6549 (0.65); 1.6463 (0.63); 1.6341
(0.43); 1.6004 (1.6); 1.5859 (3.6); 1.5791 (3.91); 1.5661 (1.86); 1.3966 (0.4); 1.3312 (0.52); 1.318
(0.62); 1.3117 (0.71); 1.2978 (0.44); 1.2651 (1.73); 1.2518 (3.47); 1.2451 (3.89); 1.2311 (1.8); 1.217
(0.45); 1.1924 (3.07); 1.1745 (5.77); 1.1568 (2.92); 0.0081 (1.01); −0.0002 (34.96); −0.0085 (1.17); −3.0246
(0.33)
Ex. 25, solvent: [CD3CN], spectrometer: 601.6 MHz 7.9022 (3.82); 7.8879 (4.08); 7.6652 (3.91); 7.6609 (4.01); 7.52 (1.53); 7.4355 (2.47); 7.4312 (2.34);
7.4212 (2.34); 7.4169 (2.23); 4.0758 (0.58); 4.064 (1.8); 4.0521 (1.78); 4.0403 (0.62); 3.9724 (16);
3.893 (0.72); 2.1596 (251.61); 2.0611 (0.72); 2.057 (1.25); 2.0529 (1.77); 2.0487 (1.27); 2.0447 (0.68);
1.9732 (8.88); 1.9666 (29.58); 1.9584 (12.1); 1.9543 (16.7); 1.9505 (119.09); 1.9464 (214.31); 1.9423
(320.41); 1.9382 (222.08); 1.9341 (110.06); 1.9254 (2.33); 1.917 (0.76); 1.9128 (0.53); 1.9086 (0.36);
1.8357 (0.67); 1.8317 (1.23); 1.8275 (1.73); 1.8234 (1.22); 1.8193 (0.63); 1.5855 (1.79); 1.5758 (4.1);
1.5715 (4.17); 1.5623 (2.12); 1.382 (2.17); 1.3727 (4.02); 1.3684 (4.12); 1.3586 (1.71); 1.2691 (1.08);
1.2158 (2.25); 1.204 (4.73); 1.1922 (2.22); 0.0053 (1.55); −0.0002 (41.75); −0.0058 (1.45)

| Ex. 26, solvent: [DMSO], spectrometer: 399.95 MHz |
|---|

14.5618 (0.37); 14.1854 (0.35); 9.5578 (1.5); 9.4271 (4.93); 9.2998 (0.36); 9.182 (0.38); 7.7634 (0.46); 7.7069 (1.14); 7.6847 (2.16); 7.5756 (3.33); 7.5541 (4.12); 7.5266 (0.76); 7.4862 (3.47); 7.3446 (0.38); 7.3053 (0.47); 7.275 (2.4); 7.2683 (2.29); 7.2533 (2.08); 7.2469 (1.92); 6.2641 (0.37); 4.9734 (1.6); 4.9321 (1.8); 4.5811 (1.98); 4.537 (3.53); 4.1428 (0.59); 4.0566 (5.17); 4.0378 (2.79); 4.0204 (2.99); 4.0026 (0.88); 3.9185 (0.48); 3.8903 (16); 3.8573 (0.39); 3.427 (1.33); 3.3939 (4.28); 3.3402 (400.48); 3.3359 (525.28); 3.3323 (787.02); 3.3084 (5.46); 3.272 (0.61); 3.2561 (0.46); 3.247 (0.37); 3.1263 (0.42); 2.7317 (0.36); 2.6709 (1.52); 2.5869 (0.39); 2.5415 (0.81); 2.5019 (262.13); 2.3291 (1.73); 2.0734 (1.24); 1.9884 (10.84); 1.5957 (5.63); 1.5917 (5.18); 1.576 (1.96); 1.5443 (0.37); 1.3969 (0.85); 1.278 (1.69); 1.2718 (1.78); 1.2585 (0.99); 1.2348 (1.26); 1.2215 (2.19); 1.207 (4.49); 1.2015 (4.56); 1.1924 (3.48); 1.1863 (1.89); 1.1747 (5.89); 1.1566 (2.78); 1.1479 (0.43); 0.8742 (0.46); 0.8572 (0.47); −0.0002 (33.26); −3.0698 (0.43)

| Ex. 27, solvent: [DMSO], spectrometer: 399.95 MHz |
|---|

11.4041 (3.19); 9.3381 (2.87); 7.9571 (1.61); 7.9504 (1.81); 7.9418 (1.7); 7.9349 (1.72); 7.8013 (0.9); 7.7904 (0.92); 7.7832 (1.04); 7.7788 (0.95); 7.7717 (1.01); 7.7681 (1.07); 7.7609 (1.06); 7.7609 (0.81); 7.4187 (1.73); 7.3949 (2.44); 7.3715 (1.58); 4.0894 (4.37); 4.0563 (1.24); 4.0384 (4.43); 4.0308 (15.34); 4.0206 (4.05); 4.0029 (1.29); 3.5817 (0.36); 3.5615 (0.4); 3.5454 (0.49); 3.3749 (56.68); 3.1998 (0.54); 3.1712 (0.38); 3.0611 (0.42); 2.6762 (0.39); 2.6716 (0.49); 2.6674 (0.4); 2.5249 (0.94); 2.5068 (58.75); 2.5027 (78.81); 2.4986 (54.63); 2.3339 (0.38); 2.3294 (0.51); 2.325 (0.35); 1.9888 (16); 1.9093 (0.63); 1.5971 (1.56); 1.5828 (3.77); 1.5759 (3.95); 1.5626 (1.86); 1.2977 (2.14); 1.2839 (3.86); 1.2772 (4.13); 1.2626 (1.77); 1.2355 (1.38); 1.1928 (4.29); 1.175 (8.54); 1.1572 (4.24); −0.0002 (11.21); −0.0085 (0.33)

| Ex. 28, solvent: [DMSO], spectrometer: 399.95 MHz |
|---|

9.475 (0.97); 9.3642 (5.1); 9.3069 (0.43); 8.7987 (0.37); 7.6689 (0.73); 7.5838 (0.66); 7.5622 (0.78); 7.4575 (2.92); 7.4414 (4.62); 7.4312 (1.02); 7.4246 (5.68); 7.42 (6.85); 7.4037 (7.53); 7.3379 (0.95); 7.3163 (1.1); 7.2661 (6.47); 7.2452 (5.07); 7.0778 (1.07); 7.0631 (0.5); 7.0582 (0.85); 6.9726 (1.86); 6.966 (1.92); 6.9512 (1.68); 6.945 (1.6); 5.4201 (2.11); 5.3833 (2.31); 4.9665 (0.6); 4.9267 (2.61); 4.8893 (2.28); 4.0551 (0.77); 4.045 (2.59); 4.0382 (2.1); 4.02 (1.77); 4.0026 (0.63); 3.8971 (16); 3.4603 (0.41); 3.4347 (0.7); 3.4009 (1.13); 3.3491 (582.58); 3.3413 (1358.67); 3.2752 (0.66); 2.6758 (1.21); 2.6711 (1.86); 2.5416 (1.04); 2.5247 (3.14); 2.5068 (206.51); 2.5026 (285.02); 2.4985 (203.82); 2.3336 (1.4); 2.3291 (1.76); 2.073 (2.52); 1.9885 (7.71); 1.6108 (1.9); 1.5968 (4.8); 1.59 (5.1); 1.5767 (2.1); 1.2799 (0.58); 1.2589 (1.23); 1.2344 (1.37); 1.2154 (2.1); 1.2016 (4.33); 1.1931 (5.24); 1.1801 (1.87); 1.1748 (4.28); 1.1569 (2.03); 0.8595 (0.42); 0.6779 (0.36); −0.0002 (6.05)

| Ex. 29, solvent: [DMSO], spectrometer: 399.95 MHz |
|---|

11.5012 (3.45); 7.8648 (3.09); 7.8592 (3.49); 7.7164 (1.51); 7.7101 (1.37); 7.6943 (2.21); 7.6884 (2.2); 7.6159 (3.95); 7.594 (2.49); 4.0557 (0.65); 4.0379 (1.84); 4.0213 (16); 4.0026 (0.71); 3.4274 (0.34); 3.3515 (266.05); 3.349 (285.95); 3.3448 (214.54); 3.3422 (330.15); 3.3382 (346.98); 3.3349 (418.93); 3.293 (1.7); 3.2756 (1.97); 3.2593 (1.38); 3.2431 (0.63); 2.6712 (1.08); 2.6665 (0.8); 2.5414 (0.49); 2.5021 (170.74); 2.3288 (1.03); 2.3248 (0.78); 2.0733 (0.83); 1.9886 (6.8); 1.9206 (1.12); 1.8997 (3.5); 1.8826 (1.26); 1.5485 (1.15); 1.5306 (3.67); 1.5136 (0.94); 1.2328 (0.5); 1.1925 (1.89); 1.1747 (3.72); 1.1569 (1.93); 1.121 (14.9); 1.1043 (14.88); −0.0002 (10.09)

| Ex. 30, solvent: [DMSO], spectrometer: 399.95 MHz |
|---|

17.8767 (0.49); 16.7278 (0.5); 15.2907 (0.46); 14.6922 (0.48); 11.3194 (0.47); 9.9917 (0.45); 9.5478 (1.93); 9.4196 (4.84); 7.9522 (1.92); 7.697 (1.24); 7.6759 (1.54); 7.6545 (1.48); 7.6289 (0.45); 7.5637 (3.75); 7.5423 (4.82); 7.5163 (0.81); 7.4807 (3.23); 7.4748 (3.56); 7.2683 (2.26); 7.2621 (1.93); 7.2473 (1.94); 7.24 (1.91); 6.5709 (0.48); 6.1831 (0.45); 4.9061 (1.2); 4.8649 (1.59); 4.5294 (1.43); 4.5247 (1.64); 4.4875 (1.39); 4.4825 (1.3); 4.4256 (1.93); 4.1384 (0.72); 4.0647 (6.28); 4.0384 (0.58); 4.0199 (0.67); 3.9606 (0.54); 3.9181 (0.47); 3.8854 (16); 3.759 (0.48); 3.4178 (0.55); 3.3771 (1.43); 3.3282 (1057.25); 3.251 (0.64); 2.8906 (12.28); 2.7309 (10.63); 2.6754 (1.93); 2.6707 (2.33); 2.5407 (1.33); 2.5057 (285.9); 2.5017 (383.65); 2.4982 (282.92); 2.3283 (2.31); 2.0733 (2.62); 1.9883 (1.97); 1.8712 (0.61); 1.7761 (11.28); 1.7311 (4.12); 1.6113 (1.99); 1.5966 (6.09); 1.5904 (5.32); 1.5777 (2.22); 1.2931 (0.88); 1.279 (1.92); 1.273 (2.06); 1.2578 (0.96); 1.2365 (1.31); 1.2229 (1.94); 1.2088 (4.32); 1.2025 (4.5); 1.1879 (1.67); 1.1747 (0.96); 1.1567 (0.93); 0.0078 (1.82); −0.0002 (58.33); −0.0086 (1.83); −2.3925 (0.46); −2.4975 (0.45); −3.438 (0.46)

| Ex. 31, solvent: [DMSO], spectrometer: 399.95 MHz |
|---|

9.6271 (0.33); 9.4864 (1.04); 9.3652 (4.55); 7.6886 (0.76); 7.6822 (0.75); 7.5821 (0.72); 7.5605 (1.05); 7.4744 (2.86); 7.4687 (2.84); 7.4508 (0.45); 7.4243 (4.62); 7.4029 (5.04); 7.3666 (0.94); 7.362 (1.49); 7.3577 (0.73); 7.345 (4.29); 7.341 (2.48); 7.3269 (4.69); 7.3153 (1.34); 7.311 (2.53); 7.3074 (1.78); 7.3007 (0.69); 7.2937 (2.58); 7.2842 (0.59); 7.2752 (0.73); 7.2699 (0.96); 7.2509 (1.5); 7.2417 (3.98); 7.2377 (4.77); 7.2211 (3.59); 7.0343 (0.74); 7.0277 (0.66); 7.0153 (0.67); 6.96 (1.73); 6.9536 (1.69); 6.9387 (1.64); 6.9318 (1.6); 5.4626 (2.05); 5.4257 (2.49); 4.9216 (1.23); 4.9128 (2.37); 4.8762 (2.17); 4.0758 (0.37); 4.0556 (0.88); 4.0379 (2.56); 4.0201 (2.74); 4.0023 (0.88); 3.9667 (3.2); 3.9535 (0.34); 3.8996 (16); 3.3929 (0.35); 3.3332 (300.56); 3.3257 (628.51); 3.3027 (7.43); 2.6752 (1.18); 2.6706 (1.5); 2.6659 (1.01); 2.5407 (0.85); 2.524 (2.63); 2.5193 (3.68); 2.5058 (169.66); 2.5016 (233.25); 2.4977 (156.25); 2.3329 (1.14); 2.3282 (1.65); 2.3237 (1.1); 2.0733 (1.21); 1.9884 (11.36); 1.6066 (1.94); 1.5924 (4.57); 1.5856 (4.63); 1.5728 (2.04); 1.2823 (0.53); 1.2698 (0.96); 1.2621 (1.07); 1.2482 (0.71); 1.235 (1.64); 1.2116 (1.99); 1.198 (3.98); 1.1921 (7.04); 1.1746 (6.85); 1.1567 (3.11); 0.1462 (0.36); 0.0081 (2); −0.0002 (76.87); −0.0085 (2.13); −0.1493 (0.33)

| Ex. 32, solvent: [DMSO], spectrometer: 399.95 MHz |
|---|

19.4883 (0.33); 14.4743 (0.34); 9.9628 (0.33); 9.4772 (1.71); 9.366 (4.51); 8.5874 (0.8); 8.5782 (0.78); 8.5563 (2.19); 8.547 (2.12); 7.8384 (1.13); 7.8194 (2.22); 7.8147 (2.2); 7.8004 (1.32); 7.7955 (1.32); 7.7145 (0.49); 7.6895 (0.9); 7.6743 (0.51); 7.6709 (0.55); 7.5658 (1.2); 7.5441 (1.65); 7.5333 (1.55);

| |
|---|
| -continued |
| 7.5212 (3.6); 7.5155 (3.87); 7.4745 (3.75); 7.4531 (4.46); 7.4106 (3.5); 7.3909 (2.71); 7.3429 (1.51); 7.3315 (1.79); 7.3238 (1.72); 7.3124 (1.73); 7.2885 (0.58); 7.2779 (0.44); 7.2717 (2.25); 7.265 (2.21); 7.2499 (1.86); 7.2432 (1.77); 7.1046 (0.9); 7.0848 (0.86); 5.296 (1.4); 5.256 (3.53); 5.2123 (3.53); 5.1725 (1.5); 4.9686 (2.74); 4.1368 (5.32); 4.0557 (0.94); 4.0379 (2.86); 4.0202 (2.95); 3.9976 (16); 3.3915 (0.41); 3.3305 (304.35); 3.3279 (296.34); 3.3249 (391.32); 3.2506 (0.34); 2.6708 (1.53); 2.5409 (0.84); 2.5016 (246.17); 2.4386 (0.36); 2.4326 (0.43); 2.3282 (1.61); 2.0734 (1.6); 1.9885 (11.41); 1.9079 (0.43); 1.6004 (2.1); 1.5867 (5.4); 1.5798 (5.52); 1.5671 (2.28); 1.2692 (0.65); 1.2565 (1.56); 1.2491 (1.54); 1.235 (1.41); 1.2013 (1.93); 1.192 (5.11); 1.1816 (4.31); 1.1746 (6.69); 1.1672 (1.83); 1.1569 (3.02); 0.0075 (2.36); −0.0002 (43.57); −1.8063 (0.33)<br>Ex. 33, solvent: [DMSO], spectrometer: 399.95 MHz |
| 9.5775 (4.49); 9.5053 (0.45); 7.7786 (3.6); 7.7682 (0.92); 7.7572 (4.87); 7.7138 (0.34); 7.692 (0.35); 7.5946 (0.68); 7.573 (0.96); 4.0552 (0.63); 4.0374 (1.94); 4.0273 (2.07); 4.0163 (16); 4.002 (0.93); 3.4947 (0.62); 3.4821 (0.65); 3.3765 (615.2); 3.372 (488.62); 3.3684 (526.05); 3.3645 (546.77); 3.3625 (654.08); 3.359 (560.12); 3.2239 (0.35); 2.6782 (1.18); 2.6736 (1.67); 2.669 (1.25); 2.5438 (0.92); 2.527 (3); 2.5222 (4.56); 2.5136 (82.6); 2.5091 (180.41); 2.5045 (246.26); 2.5 (178.36); 2.4955 (86.07); 2.3358 (1.2); 2.3312 (1.65); 2.3267 (1.27); 2.2807 (1.71); 2.2634 (1.73); 2.2212 (0.46); 2.2023 (0.41); 2.0759 (1.71); 1.9902 (8.07); 1.6323 (1.61); 1.6181 (3.95); 1.6112 (4.4); 1.5979 (2.13); 1.3975 (0.64); 1.3544 (0.4); 1.2986 (2.04); 1.2849 (4.05); 1.2782 (4.47); 1.2636 (1.91); 1.2528 (0.8); 1.2356 (1.05); 1.1924 (2.24); 1.1746 (4.33); 1.1568 (2.15); 1.0046 (0.45); 0.9858 (0.8); 0.967 (0.39); 0.9035 (4.02); 0.8858 (8.59); 0.8681 (3.9); 0.008 (0.47); −0.0002 (15.07); −0.0086 (0.55)<br>Ex. 34, solvent: [DMSO], spectrometer: 601.6 MHz |
| 11.5357 (2.35); 9.5094 (2.93); 7.7744 (2.41); 7.7701 (2.69); 7.7094 (1.22); 7.7051 (1.07); 7.6949 (1.54); 7.6906 (1.44); 7.5923 (2.62); 7.5777 (2.13); 4.3468 (0.77); 4.3348 (2.43); 4.3228 (2.45); 4.3107 (0.79); 4.0465 (1.21); 4.0346 (3.71); 4.0228 (3.71); 4.011 (1.24); 3.3485 (39.29); 3.063 (1.4); 2.8638 (1.42); 2.5098 (6.24); 2.5069 (13.35); 2.5039 (18.23); 2.5009 (13.5); 2.498 (6.41); 1.991 (16); 1.6057 (1.04); 1.5963 (2.46); 1.5918 (2.7); 1.5829 (1.07); 1.4232 (3.53); 1.4112 (7.51); 1.3991 (3.52); 1.3831 (0.35); 1.371 (0.73); 1.359 (0.33); 1.2704 (1.14); 1.2612 (2.43); 1.2568 (2.67); 1.2472 (1); 1.1869 (4.33); 1.175 (8.76); 1.1632 (4.27); −0.0002 (1.62)<br>Ex. 35, solvent: [DMSO], spectrometer: 399.95 MHz |
| 11.5005 (4.87); 9.4951 (6.27); 7.7618 (4.81); 7.7554 (5.95); 7.7144 (2.63); 7.7078 (2); 7.6925 (3.37); 7.686 (2.85); 7.5904 (5.35); 7.5686 (3.92); 4.2725 (3.11); 4.2554 (8.27); 4.2381 (3.15); 4.0382 (0.36); 4.0188 (0.33); 3.4841 (0.32); 3.4614 (0.46); 3.4443 (0.55); 3.4137 (0.86); 3.3433 (1492.06); 3.2822 (3.03); 3.25 (1.84); 3.2136 (1.16); 3.1836 (0.68); 3.1568 (0.48); 3.0604 (1.58); 2.8553 (1.58); 2.6765 (0.88); 2.6715 (1.15); 2.6668 (0.89); 2.5808 (0.37); 2.5419 (0.94); 2.5068 (140.47); 2.5027 (192.83); 2.4986 (142.05); 2.4395 (1.46); 2.4062 (0.88); 2.4024 (0.84); 2.3507 (0.48); 2.3295 (1.39); 2.3251 (1.13); 2.3016 (0.38); 2.0748 (2.08); 1.9892 (1.51); 1.8724 (0.86); 1.8543 (2.3); 1.8363 (4.51); 1.8184 (4.61); 1.8002 (2.47); 1.7815 (0.63); 1.6082 (2.21); 1.5942 (5.23); 1.5868 (5.61); 1.5738 (2.55); 1.5334 (0.32); 1.3974 (9.15); 1.2748 (2.5); 1.2617 (5.29); 1.2545 (5.68); 1.24 (2.34); 1.1923 (0.45); 1.1741 (0.77); 1.1568 (0.42); 0.8614 (7.69); 0.8431 (16); 0.8244 (7.18); −0.0002 (12.56); −0.0087 (0.62)<br>Ex. 36, solvent: [DMSO], spectrometer: 601.6 MHz |
| 11.4548 (1.5); 9.3583 (1.27); 7.9479 (0.56); 7.9434 (0.64); 7.9378 (0.61); 7.9332 (0.58); 7.7878 (0.37); 7.7856 (0.39); 7.7807 (0.35); 7.7778 (0.36); 7.7728 (0.41); 7.771 (0.4); 7.4149 (0.55); 7.3992 (0.89); 7.3837 (0.52); 4.2745 (0.87); 4.2629 (1.71); 4.2513 (0.87); 4.0461 (1.23); 4.0343 (3.73); 4.0224 (3.73); 4.0106 (1.24); 3.3508 (5.32); 3.0615 (0.46); 2.857 (0.46); 2.5216 (0.38); 2.5067 (18.22); 2.5038 (24.1); 2.5008 (17.69); 1.9909 (16); 1.8508 (0.62); 1.8388 (1.21); 1.8269 (1.23); 1.8149 (0.65); 1.5953 (0.63); 1.5859 (1.53); 1.5813 (1.8); 1.5724 (0.68); 1.2932 (0.72); 1.2841 (1.56); 1.2796 (1.68); 1.2702 (0.7); 1.1866 (4.25); 1.1747 (8.49); 1.1629 (4.18); 0.9297 (0.46); 0.8596 (1.94); 0.8473 (4.1); 0.835 (1.9); 0.8263 (0.36); −0.0002 (1.87)<br>Ex. 37, solvent: [DMSO], spectrometer: 399.95 MHz |
| 11.4582 (4.4); 9.3437 (3.47); 7.9546 (1.99); 7.9477 (2.21); 7.9391 (2.06); 7.9323 (2.22); 7.7969 (1.11); 7.7896 (1.15); 7.7858 (1.31); 7.7786 (1.09); 7.7744 (1.19); 7.7674 (1.35); 7.7633 (1.35); 7.7565 (1.05); 7.4195 (2.16); 7.3953 (2.98); 7.3726 (1.97); 4.4209 (0.48); 4.402 (0.49); 4.3576 (1.39); 4.3397 (4.42); 4.3215 (4.47); 4.3031 (1.4); 4.2264 (0.44); 4.209 (0.72); 4.1911 (0.99); 4.1728 (0.68); 4.0554 (1.12); 4.0376 (3.61); 4.0198 (3.61); 4.002 (1.17); 3.4598 (0.4); 3.3366 (26.64); 3.2408 (0.63); 3.2327 (0.6); 3.18 (0.49); 3.0617 (7.35); 2.9068 (0.33); 2.862 (7.44); 2.6758 (0.84); 2.6713 (1.17); 2.6666 (0.87); 2.5416 (0.6); 2.5245 (2.07); 2.5199 (2.85); 2.5063 (123.98); 2.5022 (170.52); 2.4985 (114.01); 2.3384 (0.38); 2.3333 (0.8); 2.3286 (1.21); 2.3245 (0.85); 2.3194 (0.49); 2.0755 (0.47); 1.9893 (16); 1.9091 (0.6); 1.5982 (1.91); 1.5841 (4.44); 1.5769 (4.72); 1.5638 (2.26); 1.4339 (6.76); 1.4158 (15.95); 1.3976 (7.06); 1.3891 (2.15); 1.3757 (2.45); 1.371 (4.02); 1.3576 (1.14); 1.3528 (1.86); 1.2979 (2.59); 1.2842 (4.49); 1.2773 (4.85); 1.2627 (2.22); 1.2354 (0.95); 1.1923 (4.5); 1.1745 (8.88); 1.1567 (4.35); 0.8883 (0.35); 0.008 (0.92); −0.0002 (35.96); −0.0085 (1.05)<br>Ex. 38, solvent: [DMSO], spectrometer: 601.6 MHz |
| 9.5496 (0.57); 9.4141 (0.99); 7.9531 (2.11); 7.6736 (0.9); 7.6699 (0.6); 7.6588 (0.63); 7.5771 (0.34); 7.5534 (0.98); 7.5391 (1.1); 7.433 (0.87); 7.4286 (0.92); 7.2914 (0.53); 7.2868 (0.49); 7.2769 (0.48); 7.2725 (0.45); 4.3763 (0.46); 4.3643 (0.47); 4.2607 (0.37); 4.1747 (0.32); 4.1628 (0.38); 3.4447 (5.41); 3.3584 (170.61); 3.335 (1.41); 3.2387 (2.83); 2.8911 (16); 2.7312 (13.04); 2.7307 (12.77); 2.5251 (0.36); 2.522 (0.46); 2.5189 (0.48); 2.5099 (12.87); 2.507 (27.63); 2.504 (37.72); 2.501 (27.87); 2.4981 (13.11); 1.6046 (0.84); 1.6005 (0.7); 1.5953 (0.94); 1.5911 (1.16); 1.5824 (0.42); 1.4525 (0.74); 1.4405 (1.57); 1.4285 (0.74); 1.308 (1.26); 1.296 (2.69); 1.2908 (0.39); 1.284 (1.46); 1.2771 (0.59); 1.1964 (0.45); 1.1876 (0.87); 1.1835 (0.88); 1.1744 (0.48); −0.0002 (5.92) |

-continued

Ex. 39, solvent: [DMSO], spectrometer: 399.95 MHz 16.4832 (0.33); 15.8688 (0.33); 13.2954 (0.33); 9.6257 (0.34); 9.6097 (2.28); 9.4715 (4.25); 9.4357 (0.37); 9.3286 (0.34); 8.0115 (1.98); 8.0058 (2.14); 7.6392 (4.36); 7.6335 (3.82); 7.6013 (0.4); 7.5949 (0.44); 7.5777 (0.47); 7.5615 (0.48); 7.5253 (0.37); 7.4896 (3.22); 7.4834 (3.02); 7.4395 (0.43); 7.4325 (0.57); 7.4255 (0.52); 7.4196 (0.37); 5.7522 (0.33); 4.1774 (0.4); 4.1601 (0.99); 4.1421 (1.31); 4.1253 (1.47); 4.1073 (1.28); 4.0847 (8.62); 4.0554 (1.29); 4.0376 (3.86); 4.0199 (3.78); 4.0022 (1.25); 3.9064 (0.38); 3.8793 (1.92); 3.8664 (14.52); 3.8554 (1.87); 3.8367 (0.71); 3.8182 (1.21); 3.8004 (1.64); 3.7833 (1.43); 3.7657 (1.14); 3.7471 (0.43); 3.7013 (0.51); 3.6822 (0.73); 3.6642 (0.9); 3.6454 (1); 3.6338 (0.83); 3.6158 (0.91); 3.5968 (0.64); 3.5781 (0.38); 3.4622 (0.34); 3.4401 (0.39); 3.4079 (0.75); 3.3466 (768.76); 3.3431 (1758.18); 3.3199 (5.3); 3.2876 (0.84); 3.2746 (0.59); 3.2684 (0.52); 3.2291 (0.35); 3.2188 (0.44); 2.6767 (1.39); 2.6717 (1.92); 2.6678 (1.4); 2.5418 (0.89); 2.5252 (3.39); 2.5111 (113.97); 2.5071 (219.12); 2.5029 (302.49); 2.4987 (211.86); 2.4946 (105.8); 2.4557 (0.43); 2.3342 (1.35); 2.3295 (1.8); 2.3249 (1.43); 2.075 (2.09); 1.9893 (16); 1.6178 (2.02); 1.6037 (6.07); 1.5977 (5.35); 1.5842 (2.19); 1.5755 (0.39); 1.3835 (0.33); 1.3449 (0.36); 1.3127 (1.03); 1.298 (2.27); 1.2915 (2.11); 1.2761 (0.89); 1.2588 (0.57); 1.2327 (3.01); 1.2191 (4.19); 1.2121 (4.3); 1.1979 (1.6); 1.1924 (4.68); 1.1746 (8.79); 1.1567 (8.3); 1.1383 (9.27); 1.1204 (4.08); 1.0992 (0.35); 0.9885 (0.33); 0.9703 (2.29); 0.9523 (4.58); 0.9345 (2.19); −0.0002 (11.63); −0.0088 (0.43); −3.0168 (0.32)

Ex. 40, solvent: [DMSO], spectrometer: 399.95 MHz 11.491 (2.41); 7.8981 (2.63); 7.8918 (2.76); 7.7092 (1.29); 7.7028 (1.18); 7.6873 (1.79); 7.6809 (1.74); 7.5849 (3.2); 7.563 (2.31); 4.056 (0.73); 4.0381 (2.56); 4.0288 (11.26); 4.0205 (2.67); 4.0026 (0.76); 3.3518 (0.45); 3.3286 (152.33); 2.5244 (1.09); 2.5195 (1.69); 2.5109 (19.1); 2.5065 (38.19); 2.502 (49.79); 2.4974 (35.73); 2.493 (17.31); 2.3955 (16); 2.3286 (0.34); 2.074 (0.42); 1.9888 (9.22); 1.8766 (1.77); 1.6065 (0.84); 1.1926 (2.46); 1.1748 (4.87); 1.157 (2.4); −0.0002 (5.14)

Ex. 41, solvent: [DMSO], spectrometer: 601.6 MHz 9.4121 (0.42); 7.9528 (1.18); 7.7388 (0.36); 7.7028 (0.82); 7.6882 (1.07); 7.674 (0.37); 7.6583 (0.38); 7.6479 (0.99); 7.6438 (1.12); 7.6126 (1.11); 7.5995 (1.46); 7.5769 (0.36); 7.5533 (0.48); 7.5395 (0.48); 7.433 (0.5); 7.4291 (0.53); 7.3221 (0.64); 7.2903 (0.44); 7.2761 (0.33); 7.2716 (0.34); 4.3716 (1.39); 4.3595 (1.67); 4.272 (0.39); 4.2601 (0.39); 4.2481 (0.36); 4.1277 (0.42); 4.1191 (0.42); 4.0334 (0.56); 4.0216 (0.56); 3.5061 (0.42); 3.4808 (1.12); 3.4549 (16); 3.444 (2.94); 3.4284 (0.6); 3.3956 (1.34); 3.3758 (5.24); 3.3517 (4904.54); 3.3282 (80.11); 3.2755 (1.57); 3.2474 (4.78); 3.2383 (1.31); 3.1704 (1.74); 3.1617 (1.71); 3.1108 (1.82); 3.0743 (1.14); 2.8906 (8.65); 2.8645 (4.58); 2.7306 (7.07); 2.618 (10.41); 2.615 (14.06); 2.6121 (10.4); 2.5428 (5.84); 2.5243 (20.27); 2.5213 (25.42); 2.5182 (25.36); 2.5091 (738.32); 2.5062 (1554.79); 2.5033 (2093.86); 2.5003 (1556.28); 2.4974 (750.49); 2.3904 (9.64); 2.3874 (13.16); 2.3845 (9.61); 2.283 (0.4); 2.0787 (15.29); 1.9906 (2.25); 1.6777 (3.23); 1.6044 (0.51); 1.591 (0.77); 1.582 (0.49); 1.5066 (0.63); 1.4948 (0.86); 1.4825 (0.67); 1.4514 (2.04); 1.4394 (4.05); 1.4273 (2.94); 1.415 (1.05); 1.3496 (2.36); 1.3072 (1.28); 1.2954 (1.78); 1.2833 (1.18); 1.2666 (0.69); 1.2576 (1.03); 1.2338 (6.68); 1.1951 (0.48); 1.1859 (1.2); 1.174 (1.49); 1.1622 (0.72); 1.0541 (0.42); 0.8646 (0.43); 0.8535 (1.03); 0.8416 (0.52); 0.0965 (1.89); 0.0052 (14.67); −0.0002 (473.67); −0.0057 (19.93); −0.1 (1.92)

Ex. 42, solvent: [DMSO], spectrometer: 601.6 MHz 11.0933 (3.12); 10.6126 (0.51); 9.5132 (3.58); 9.5027 (0.8); 7.8641 (2.73); 7.86 (2.86); 7.8428 (1.09); 7.839 (0.51); 7.8313 (0.4); 7.7552 (1.31); 7.751 (1.2); 7.7406 (1.56); 7.7365 (1.44); 7.5785 (3.5); 7.564 (2.35); 7.5578 (0.51); 7.5418 (0.41); 4.1945 (2.61); 4.0334 (0.76); 4.0215 (0.81); 4.0064 (12.33); 3.3813 (1.49); 3.3561 (1038.24); 3.3325 (10.5); 2.6153 (1.84); 2.543 (0.72); 2.5245 (2.78); 2.5214 (3.59); 2.5181 (4.4); 2.5063 (218.81); 2.5036 (275.25); 2.3877 (1.67); 2.2932 (0.59); 2.2827 (16); 2.0785 (0.51); 1.9907 (3.1); 1.6109 (1.37); 1.6016 (3.69); 1.5971 (3.87); 1.5881 (1.44); 1.2646 (1.41); 1.2554 (3.39); 1.2511 (3.52); 1.2413 (1.86); 1.2344 (0.88); 1.1859 (0.82); 1.1741 (1.59); 1.1622 (0.81); 0.0049 (1.62); −0.0002 (30.57)

Ex. 43, solvent: [DMSO], spectrometer: 601.6 MHz 9.5611 (2.61); 9.4204 (5.99); 7.6917 (2.08); 7.6775 (2.5); 7.644 (2.35); 7.6398 (2.43); 7.5687 (5.27); 7.5544 (5.96); 7.5008 (1.35); 7.4967 (1.29); 7.4867 (1.16); 7.4825 (1.15); 7.4199 (4.23); 7.4158 (4.42); 7.2921 (2.65); 7.288 (2.5); 7.2779 (2.46); 7.2736 (2.33); 4.3914 (0.77); 4.3788 (2.21); 4.367 (2.26); 4.3549 (0.78); 4.268 (0.45); 4.2567 (1.31); 4.2449 (1.84); 4.2335 (2.3); 4.2217 (1.95); 4.21 (0.64); 4.1658 (0.64); 4.1541 (1.99); 4.1423 (2.5); 4.1343 (1.96); 4.1311 (2.19); 4.1224 (2.3); 4.1193 (1.88); 4.1114 (2.32); 4.0996 (1.8); 4.0878 (0.56); 4.0334 (0.37); 4.0216 (0.36); 3.7795 (0.53); 3.7678 (1.63); 3.7559 (2.07); 3.7448 (1.99); 3.7328 (1.56); 3.7214 (0.53); 3.6919 (0.56); 3.68 (0.78); 3.6676 (0.94); 3.6558 (0.78); 3.5796 (0.83); 3.5678 (1); 3.5556 (0.85); 3.5436 (0.6); 3.4046 (0.45); 3.3945 (1.21); 3.3858 (1.16); 3.3796 (1.18); 3.3518 (1984.37); 3.3279 (16.06); 3.3028 (0.46); 3.1702 (0.33); 3.1616 (0.43); 2.6179 (4.37); 2.6151 (5.71); 2.6123 (4.23); 2.5427 (2.81); 2.5332 (0.94); 2.5242 (9.59); 2.5211 (13.27); 2.5179 (16.58); 2.5062 (657.61); 2.5033 (846.44); 2.5005 (615.2); 2.4784 (2.21); 2.3903 (3.99); 2.3875 (5.24); 2.3847 (3.83); 2.0787 (4.37); 1.9906 (5.5); 1.6175 (1.12); 1.6056 (4.24); 1.5967 (6.28); 1.5925 (6.54); 1.5838 (2.53); 1.4508 (3.21); 1.4388 (6.55); 1.4268 (3.06); 1.306 (7.37); 1.2941 (16); 1.282 (9.65); 1.2721 (1.16); 1.2576 (0.69); 1.2338 (3.09); 1.2054 (2.8); 1.1965 (5.73); 1.1922 (5.97); 1.183 (2.39); 1.1741 (0.91); 1.1621 (0.47); 1.1436 (6.79); 1.1317 (13.97); 1.1198 (6.51); 0.9438 (2.6); 0.932 (5.36); 0.9202 (2.47); 0.8535 (0.4); 0.0967 (0.49); 0.005 (5.69); −0.0002 (104.53); −0.0999 (0.47)

Ex. 44, solvent: [DMSO], spectrometer: 601.6 MHz 9.4685 (3.13); 7.6186 (2.15); 7.6043 (2.37); 7.5156 (2.09); 7.5118 (2.18); 7.3065 (1.24); 7.3024 (1.24); 7.2923 (1.16); 7.2882 (1.12); 5.2573 (1.78); 5.2279 (2.2); 4.9892 (2.11); 4.9598 (1.74); 4.0648 (0.9); 4.0453 (1.36); 4.0335 (3.87); 4.0217 (3.86); 4.0098 (1.32); 3.9354 (10.54); 3.4336 (0.7); 3.3766 (1.21); 3.352 (365.17); 3.3252 (0.47); 2.6151 (0.96); 2.5429 (0.42); 2.5034 (150.98); 2.3876 (0.93); 1.9907

-continued (16); 1.6188 (1.49); 1.6097 (3.52); 1.6054 (3.55); 1.5965 (1.28); 1.2734 (0.4); 1.2338 (0.67); 1.217 (1.28); 1.2079 (2.97); 1.2038 (3.11); 1.1942 (1.13); 1.186 (4.37); 1.1742 (8.34); 1.1623 (4.17); −0.0002 (1.27)
Ex. 45, solvent: [DMSO], spectrometer: 399.95 MHz 11.5629 (3.17); 9.5197 (3.89); 7.8939 (0.68); 7.8145 (2.97); 7.8081 (3.34); 7.6813 (1.42); 7.675 (1.32); 7.6594 (2.05); 7.653 (2.01); 7.5849 (4.03); 7.563 (2.7); 7.5353 (0.32); 5.7625 (0.52); 4.1942 (1); 4.1104 (12.73); 4.0549 (0.57); 4.0371 (1.62); 4.0193 (1.67); 4.0016 (0.65); 3.3488 (381.8); 3.3413 (634.34); 3.0337 (16); 2.681 (0.92); 2.6766 (1.94); 2.672 (2.7); 2.6675 (1.97); 2.5421 (1.6); 2.5254 (4.95); 2.5207 (7.26); 2.512 (132.84); 2.5075 (285.73); 2.503 (383.95); 2.4984 (271.1); 2.4939 (125.41); 2.3389 (0.83); 2.3343 (1.83); 2.3297 (2.55); 2.3251 (1.84); 2.0772 (0.62); 1.99 (7.2); 1.612 (1.36); 1.5977 (3.37); 1.5909 (3.47); 1.5778 (1.53); 1.2731 (1.73); 1.2596 (3.49); 1.2529 (3.76); 1.2378 (2.87); 1.1921 (1.91); 1.1742 (3.78); 1.1565 (1.84); 0.8539 (0.37); 0.008 (1.19); −0.0002 (35.07); −0.0077 (1.04)
Ex. 45, solvent: [DMSO], spectrometer: 399.95 MHz 11.5617 (2.61); 9.5199 (2.8); 7.8135 (2.59); 7.8072 (2.92); 7.6806 (1); 7.6741 (0.94); 7.6586 (1.53); 7.6522 (1.56); 7.5846 (2.73); 7.5627 (1.8); 4.1102 (12.24); 4.0369 (0.87); 4.0191 (0.88); 4.0016 (0.61); 3.3499 (1797.52); 3.2245 (0.46); 3.033 (16); 2.6813 (0.63); 2.6767 (1.35); 2.6721 (1.89); 2.6675 (1.39); 2.6629 (0.67); 2.5424 (1.08); 2.5255 (3.44); 2.5208 (5.1); 2.5121 (94.77); 2.5076 (206.74); 2.503 (279.76); 2.4984 (197.63); 2.4939 (91.37); 2.3389 (0.58); 2.3343 (1.29); 2.3297 (1.81); 2.3252 (1.31); 2.0765 (2.83); 1.9898 (4.26); 1.6115 (1.29); 1.5972 (2.98); 1.5904 (3.18); 1.5772 (1.42); 1.273 (1.66); 1.2592 (3.23); 1.2526 (3.51); 1.2379 (1.98); 1.192 (1.13); 1.1742 (2.25); 1.1564 (1.08); −0.0002 (8.57)
Ex. 46, solvent: [DMSO], spectrometer: 399.95 MHz 9.5373 (0.47); 9.3983 (0.81); 7.7053 (0.41); 7.6838 (0.63); 7.6757 (0.42); 7.6635 (0.45); 7.6546 (0.75); 7.6313 (0.77); 7.6092 (1.26); 7.5886 (1.33); 7.5792 (0.79); 7.5486 (0.9); 7.527 (0.97); 7.4347 (0.79); 7.4282 (0.89); 7.3883 (0.47); 7.3078 (1.04); 7.2891 (0.66); 7.2824 (0.56); 7.2677 (0.47); 7.2612 (0.45); 4.2924 (1.02); 4.2751 (0.9); 4.182 (0.47); 4.1649 (0.51); 4.1476 (0.56); 4.1292 (0.35); 4.0547 (1.37); 4.0369 (3.7); 4.0191 (3.74); 4.0013 (1.31); 3.4557 (10.09); 3.4453 (5.02); 3.3427 (771.28); 3.319 (13.1); 3.2679 (1.37); 3.2419 (3.06); 3.2325 (2.72); 3.1112 (13.1); 3.072 (0.85); 2.8904 (0.43); 2.8646 (2.78); 2.7312 (0.35); 2.6764 (1.44); 2.6718 (2); 2.6673 (1.53); 2.5422 (1.53); 2.5253 (3.59); 2.5205 (5.22); 2.5117 (95.58); 2.5073 (207.41); 2.5028 (281.65); 2.4982 (204.86); 2.4938 (99.47); 2.334 (1.35); 2.3295 (1.9); 2.325 (1.43); 2.0769 (2.16); 1.9899 (16); 1.9015 (0.53); 1.8832 (1); 1.8655 (1.18); 1.847 (0.97); 1.8267 (0.75); 1.8103 (0.56); 1.7924 (0.52); 1.7738 (0.52); 1.8767 (2.49); 1.6439 (0.6); 1.6192 (0.38); 1.5969 (1.32); 1.5899 (1.04); 1.5768 (0.52); 1.4012 (0.6); 1.2967 (0.71); 1.2823 (0.75); 1.2755 (0.81); 1.258 (0.71); 1.2347 (1.66); 1.2004 (0.58); 1.192 (4.72); 1.1743 (9.08); 1.1564 (4.38); 0.8945 (1.45); 0.876 (3.76); 0.8567 (3.53); 0.8335 (2.44); 0.8148 (2.63); 0.7962 (1.13); 0.146 (0.39); 0.008 (2.78); −0.0002 (90.84); −0.0085 (3.33); −0.1499 (0.34)
Ex. 47, solvent: [DMSO], spectrometer: 601.6 MHz 7.6521 (0.53); 7.4488 (0.87); 7.4092 (0.79); 7.3946 (0.85); 7.3798 (0.87); 4.3079 (0.35); 4.2962 (0.64); 4.2842 (0.81); 4.2717 (0.82); 4.2604 (0.93); 4.2489 (1.03); 4.2369 (0.57); 4.1612 (0.58); 4.1506 (0.59); 4.1386 (0.49); 4.127 (0.54); 4.1149 (0.59); 4.1037 (0.33); 4.0456 (0.57); 4.0338 (1.71); 4.022 (1.73); 4.0101 (0.58); 3.4532 (16); 3.4036 (1.29); 3.3797 (0.39); 3.3536 (287.87); 3.33 (4.06); 3.2402 (1.45); 3.1042 (0.53); 3.095 (0.47); 3.0631 (0.57); 2.9405 (0.67); 2.6832 (2.06); 2.6186 (0.56); 2.6157 (0.74); 2.6128 (0.54); 2.5249 (1.23); 2.5218 (1.83); 2.5069 (84.85); 2.504 (111.28); 2.501 (80.94); 2.391 (0.55); 2.3881 (0.73); 2.3852 (0.53); 1.9909 (7.37); 1.8792 (0.58); 1.8669 (0.68); 1.8549 (0.61); 1.8371 (0.59); 1.7449 (0.46); 1.7341 (0.59); 1.7232 (0.61); 1.7109 (0.61); 1.6979 (0.68); 1.686 (0.86); 1.6637 (1.33); 1.4754 (0.37); 1.3882 (0.95); 1.2578 (0.37); 1.2343 (1.25); 1.1862 (2.13); 1.1744 (4.02); 1.1625 (2.03); 0.8889 (1.11); 0.8766 (2.26); 0.8638 (2.34); 0.8493 (3.1); 0.6607 (0.53); 0.6484 (1.06); 0.6361 (0.51); 0.0051 (1.29); −0.0002 (25.89); −0.0056 (0.98)
Ex. 48, solvent: [DMSO], spectrometer: 601.6 MHz 7.6625 (0.59); 7.6566 (0.58); 7.6531 (0.62); 7.441 (0.93); 7.4125 (0.97); 7.3978 (1.05); 4.3751 (0.97); 4.3634 (1.3); 4.3523 (1.07); 4.3412 (1.13); 4.3294 (0.96); 4.3174 (0.42); 4.2524 (0.53); 4.0335 (0.92); 4.0217 (0.91); 3.4526 (16); 3.3768 (0.53); 3.3522 (580.58); 3.3286 (7.62); 3.2446 (1.32); 3.1036 (0.51); 3.0656 (0.51); 2.9399 (0.7); 2.6805 (2.05); 2.6182 (1.09); 2.6153 (1.49); 2.6123 (1.1); 2.543 (0.62); 2.5245 (2.25); 2.5215 (3.05); 2.5183 (3.8); 2.5094 (79.16); 2.5065 (164.86); 2.5035 (221.76); 2.5005 (162.52); 2.4977 (78.12); 2.3906 (1.05); 2.3877 (1.43); 2.3847 (1.05); 2.0789 (0.5); 1.9907 (3.97); 1.9066 (0.38); 1.6608 (1.13); 1.4749 (0.38); 1.4506 (0.98); 1.4387 (1.81); 1.4266 (1.1); 1.3791 (0.88); 1.3467 (2.94); 1.2977 (0.44); 1.2577 (0.56); 1.2337 (1.42); 1.186 (1.28); 1.1742 (2.31); 1.1623 (1.19); 0.0052 (2.55); −0.0002 (61.56); −0.0057 (2.57)
Ex. 49, solvent: [DMSO], spectrometer: 399.95 MHz 11.3656 (3.86); 9.5142 (4.4); 7.7755 (3.59); 7.7692 (3.97); 7.6847 (1.75); 7.6783 (1.49); 7.6628 (2.52); 7.6564 (2.33); 7.5817 (4.49); 7.5599 (3.05); 4.0562 (1.15); 4.0384 (3.4); 4.0206 (3.6); 4.0034 (16); 3.3453 (94.9); 3.3448 (94.73); 3.3197 (17.97); 2.5245 (0.51); 2.511 (7.72); 2.5068 (14.99); 2.5023 (19.26); 2.4978 (13.84); 2.4937 (6.76); 2.0729 (0.59); 1.9887 (13.71); 1.6091 (1.56); 1.5949 (3.86); 1.588 (4.03); 1.5747 (1.73); 1.277 (1.86); 1.2635 (3.82); 1.2568 (4.07); 1.2422 (1.5); 1.1928 (3.82); 1.1749 (7.49); 1.1572 (3.7)
Ex. 50, solvent: [DMSO], spectrometer: 601.6 MHz 9.5618 (2.56); 9.4177 (6.18); 7.9529 (0.98); 7.6923 (2.28); 7.6781 (2.69); 7.635 (2.45); 7.6308 (2.6); 7.5617 (5.97); 7.5475 (6.73); 7.5004 (1.4); 7.4963 (1.31); 7.4863 (1.23); 7.482 (1.22); 7.4233 (4.05); 7.4191 (4.25); 7.2874 (2.63); 7.283 (2.53); 7.2731 (2.42); 7.2688 (2.31); 4.3107 (0.81); 4.3036 (0.87); 4.2993 (1.52); 4.2921 (1.53); 4.2806 (0.81); 4.1677 (0.49); 4.1596 (1.05); 4.1559 (1.81); 4.1474 (2.05); 4.144 (2.45); 4.1362 (2.11); 4.1329 (2.74); 4.1249 (2.63); 4.1211 (2.27); 4.1128 (1.37); 4.0421 (1.16); 4.0323 (1.53); 4.0297 (1.5); 4.0196 (1.98); 4.0097 (1.08); 4.0068 (1.07); 3.9968 (0.83); 3.7605 (0.48); 3.7486 (1.68); 3.7369 (2.16); 3.7256 (2.07); 3.7139 (1.61); 3.7018 (0.54); 3.6876 (0.53); 3.6756 (0.76);

-continued 3.6634 (0.93); 3.6514 (0.75); 3.5736 (0.78); 3.5616 (0.93); 3.5493 (0.81); 3.5373 (0.58); 3.4009 (0.71); 3.3887 (0.8); 3.3806 (1.37); 3.3578 (1317.4); 3.334 (5.83); 2.8908 (7.36); 2.7308 (5.98); 2.6185 (1.57); 2.6155 (2.16); 2.6126 (1.59); 2.5433 (0.92); 2.5248 (3.01); 2.5217 (4.1); 2.5186 (4.76); 2.5095 (118.16); 2.5067 (245.74); 2.5038 (330.23); 2.5009 (240.75); 2.4981 (114.58); 2.3909 (1.49); 2.3879 (2.06); 2.385 (1.48); 2.0787 (0.93); 1.8893 (1); 1.8773 (2.04); 1.8652 (2.07); 1.8532 (1.07); 1.8217 (0.59); 1.8094 (1.15); 1.7977 (1.5); 1.7863 (1.74); 1.7743 (1.53); 1.7621 (0.74); 1.6799 (0.65); 1.6676 (1.17); 1.6574 (1.68); 1.645 (1.65); 1.6348 (1.13); 1.6225 (0.67); 1.6179 (1.23); 1.6084 (4.94); 1.6039 (3.6); 1.5991 (6.24); 1.5947 (7.45); 1.5859 (2.64); 1.2954 (1.19); 1.2863 (2.43); 1.2819 (2.67); 1.2724 (1); 1.2578 (0.42); 1.2335 (1.57); 1.2037 (2.86); 1.1947 (5.93); 1.1903 (6.34); 1.181 (2.45); 1.1407 (7.11); 1.1288 (14.87); 1.1168 (6.89); 0.9415 (2.6); 0.9297 (5.46); 0.9179 (2.57); 0.8865 (3.17); 0.8743 (6.67); 0.862 (3.13); 0.8535 (0.38); 0.8172 (7.63); 0.8049 (16); 0.7926 (7.21); 0.0051 (1.34); −0.0002 (32.06); −0.0057 (1.19)
Ex. 51, solvent: [DMSO], spectrometer: 601.6 MHz 11.2435 (1); 9.3497 (0.74); 7.9531 (0.39); 7.7736 (0.6); 7.7601 (0.7); 7.7304 (2.91); 7.7161 (3.31); 7.6522 (3.79); 7.6386 (3.74); 7.6244 (3.53); 7.5889 (2.65); 7.5753 (2.41); 7.5207 (1.21); 7.4121 (11.62); 7.4027 (3.64); 7.3862 (2.56); 7.3118 (2.15); 7.2988 (1.8); 7.2009 (0.39); 6.8169 (0.48); 4.3007 (3.14); 4.2901 (3.3); 4.2794 (2.58); 4.2566 (2.26); 4.2028 (1.63); 4.1284 (3.82); 4.1178 (3.61); 4.107 (3.02); 4.0674 (1.32); 4.055 (1.55); 4.0456 (2.7); 4.0338 (4.82); 4.022 (4.4); 4.0102 (1.78); 3.9587 (1.64); 3.947 (2.06); 3.9353 (1.89); 3.9165 (1.96); 3.9041 (2.3); 3.8933 (1.94); 3.8468 (1.72); 3.7093 (1.04); 3.6044 (0.96); 3.3585 (2804.89); 3.3349 (16.31); 3.2711 (0.92); 3.2466 (0.88); 3.1423 (0.68); 3.0944 (0.54); 3.061 (1.47); 3.0465 (1.27); 2.9693 (1.33); 2.8912 (2.99); 2.8563 (1.82); 2.8399 (3.68); 2.8293 (3.66); 2.7312 (2.47); 2.6188 (3.62); 2.616 (4.79); 2.6132 (3.59); 2.5436 (1.95); 2.525 (9.26); 2.522 (12.69); 2.5186 (16.24); 2.507 (555.84); 2.5043 (726.37); 2.5015 (536.53); 2.3912 (3.62); 2.3884 (4.75); 2.3856 (3.53); 2.2958 (0.37); 2.2837 (0.81); 2.2716 (0.33); 2.0789 (2.13); 1.991 (15.17); 1.8862 (1.72); 1.8744 (3.51); 1.8624 (4.2); 1.8509 (3.63); 1.8425 (3.66); 1.8307 (3.67); 1.8188 (3.58); 1.8066 (2.89); 1.794 (2.27); 1.7812 (2.03); 1.7642 (2.22); 1.7173 (14.52); 1.6892 (3.36); 1.6419 (1.13); 1.5709 (1.75); 1.5668 (1.84); 1.5023 (3.27); 1.4837 (3.07); 1.374 (3.95); 1.3622 (2.97); 1.3502 (2.21); 1.3334 (3.83); 1.3217 (5.49); 1.3103 (4.13); 1.2978 (3.26); 1.2679 (4.55); 1.2579 (5.13); 1.2343 (9.67); 1.1974 (3.99); 1.1862 (10.63); 1.1743 (14.27); 1.1624 (12.11); 1.1558 (13.88); 1.1412 (16); 1.1295 (8.23); 1.1049 (6.61); 1.0708 (6); 1.0599 (8.58); 0.9401 (3.69); 0.9284 (5.1); 0.9172 (2.68); 0.8835 (5.11); 0.8713 (10.54); 0.865 (6.44); 0.8588 (10.32); 0.8536 (8.8); 0.845 (12.86); 0.8317 (12.07); 0.78 (1.98); 0.7676 (0.91); 0.0966 (0.62); 0.005 (6.46); −0.0002 (127.14); −0.0055 (5.46); −0.1 (0.6)
Ex. 52, solvent: [DMSO], spectrometer: 399.95 MHz 9.4063 (0.33); 7.7318 (0.72); 7.7103 (0.89); 7.6897 (0.37); 7.6725 (0.36); 7.6593 (1.1); 7.6531 (1.26); 7.6406 (1.06); 7.6247 (0.89); 7.5947 (0.61); 7.5698 (0.76); 7.5483 (0.56); 7.5048 (0.39); 7.4401 (0.74); 7.4106 (1.09); 7.3918 (1.37); 7.2958 (0.47); 7.2895 (0.56); 7.2747 (0.49); 7.2686 (0.49); 4.4001 (0.35); 4.3823 (1.01); 4.3643 (1.22); 4.2654 (0.77); 4.2473 (0.94); 4.2311 (0.91); 4.2129 (0.73); 4.1602 (0.44); 4.147 (0.55); 4.1419 (0.6); 4.1332 (0.55); 4.1246 (0.64); 4.1084 (0.36); 4.055 (1.34); 4.0461 (0.4); 4.0372 (3.72); 4.0282 (0.46); 4.0194 (3.81); 4.0016 (1.44); 3.9349 (0.82); 3.9199 (0.86); 3.6846 (0.33); 3.6661 (0.36); 3.6171 (0.37); 3.5995 (0.37); 3.5078 (0.35); 3.3637 (1.04); 3.3424 (804.32); 3.3186 (9.85); 3.2893 (0.5); 3.2722 (0.6); 3.2519 (0.38); 3.2175 (0.32); 3.0961 (0.41); 3.0623 (0.35); 2.9842 (0.35); 2.8907 (1.32); 2.83 (0.8); 2.8117 (0.8); 2.7313 (0.96); 2.6766 (1.05); 2.6721 (1.47); 2.6675 (1.09); 2.5424 (0.67); 2.5255 (2.36); 2.5208 (3.63); 2.512 (75.12); 2.5075 (162.37); 2.503 (218.4); 2.4984 (156.12); 2.494 (73.27); 2.3388 (0.55); 2.3342 (1.08); 2.3297 (1.5); 2.3252 (1.13); 1.99 (16); 1.7116 (3.31); 1.6105 (0.4); 1.5971 (0.55); 1.5894 (0.58); 1.4981 (0.96); 1.458 (1.92); 1.44 (3.22); 1.4221 (1.86); 1.4094 (0.97); 1.3406 (3.68); 1.3235 (3.33); 1.3135 (3.04); 1.2956 (3.01); 1.2777 (2.74); 1.2582 (2.19); 1.2343 (5.2); 1.2036 (1.29); 1.1922 (5.62); 1.1863 (2.32); 1.1744 (10.68); 1.1676 (3.46); 1.1566 (7.96); 1.1448 (5.05); 1.1332 (3.63); 1.1153 (1.98); 1.0491 (1.91); 0.9496 (1.15); 0.9317 (1.85); 0.914 (0.87); 0.8933 (0.63); 0.8748 (1.42); 0.8624 (1.03); 0.8539 (1.15); 0.8363 (0.42); 0.1459 (0.45); 0.008 (3.24); −0.0002 (113.96); −0.0085 (3.81); −0.1496 (0.43)
Ex. 53, solvent: [DMSO], spectrometer: 399.95 MHz 11.4811 (0.46); 9.5802 (3.86); 9.504 (0.61); 7.8067 (0.33); 7.7817 (3.36); 7.7747 (1.02); 7.7681 (1.19); 7.7604 (4.49); 7.7135 (0.41); 7.6917 (0.47); 7.6851 (0.47); 7.5943 (0.9); 7.5726 (1.01); 7.3651 (0.37); 4.106 (0.36); 4.0549 (0.76); 4.037 (2.46); 4.0205 (16); 4.0015 (0.98); 3.4808 (0.47); 3.4264 (0.76); 3.4141 (1.01); 3.366 (481.46); 3.3609 (380.93); 3.3594 (381.76); 3.3541 (595.63); 3.3505 (698.07); 3.0316 (0.61); 2.6772 (1.33); 2.6727 (1.85); 2.6681 (1.36); 2.5429 (0.97); 2.5261 (3.27); 2.5213 (4.97); 2.5126 (89.86); 2.5081 (194.5); 2.5036 (263.53); 2.4991 (189.65); 2.4946 (89.56); 2.4051 (1.69); 2.335 (1.23); 2.3303 (1.72); 2.3258 (1.27); 2.0763 (1.33); 2.0394 (9.05); 1.9899 (10.76); 1.9092 (0.76); 1.6335 (1.56); 1.6194 (3.67); 1.6124 (4.01); 1.5991 (1.94); 1.5775 (0.35); 1.3543 (0.43); 1.2973 (1.85); 1.2837 (3.68); 1.277 (4.01); 1.2623 (1.85); 1.2521 (0.95); 1.2369 (1.14); 1.1922 (2.96); 1.1744 (5.8); 1.1566 (2.83); 0.008 (0.76); −0.0002 (21.52); −0.0085 (0.61)
Ex. 54, solvent: [DMSO], spectrometer: 399.95 MHz 9.4882 (0.79); 9.3813 (4.43); 8.5176 (2.05); 8.5137 (2.27); 8.5056 (2.27); 8.5017 (2.28); 8.4323 (3.23); 8.4273 (3.41); 8.2561 (0.5); 8.2509 (0.53); 7.952 (0.59); 7.7143 (0.68); 7.7082 (0.72); 7.6847 (1.07); 7.6801 (1.7); 7.6753 (1.15); 7.6651 (1.28); 7.6603 (1.95); 7.6556 (1.27); 7.5766 (0.52); 7.555 (0.77); 7.5036 (2.71); 7.4973 (2.86); 7.4812 (0.43); 7.4689 (0.59); 7.4626 (0.76); 7.4508 (4.33); 7.4415 (0.51); 7.4293 (4.72); 7.4088 (1.88); 7.3969 (1.79); 7.3893 (1.66); 7.3773 (1.57); 6.9932 (1.56); 6.9868 (1.58); 6.9719 (1.46); 6.9654 (1.45); 5.4683 (2.14); 5.4307 (2.45); 5.0433 (0.53); 4.9816 (2.41); 4.9544 (0.36); 4.9441 (2.09); 4.0808 (2.62); 4.0555 (0.62); 4.0377 (1.82); 4.02 (1.85); 4.0022 (0.63); 3.9068 (16); 3.3269 (326.92); 3.322 (337.09); 2.8902 (5.17); 2.7304 (4.11); 2.6791 (0.48); 2.675 (1.04); 2.6704 (1.48); 2.6658 (1.11); 2.6613 (0.56); 2.5408 (0.86); 2.5237 (2.77); 2.5102 (73.18); 2.5058 (152.67); 2.5013 (207.94); 2.4967 (155.09); 2.4923 (79.01); 2.337 (0.46); 2.3326 (1.01); 2.3281 (1.42); 2.3235 (1.05); 2.3191 (0.53); 2.0737 (0.39); 1.9884 (7.83); 1.6127 (2.1); 1.5986 (4.95); 1.5917 (5.39); 1.5785 (2.38); 1.2787 (0.41); 1.2653 (0.83); 1.2583 (1.18); 1.2433 (0.76); 1.2353 (1.12); 1.2176 (1.97);

1.204 (4.14); 1.1973 (4.51); 1.1924 (3.36); 1.183 (1.78); 1.1745 (4.42); 1.1567 (2.17); 0.008 (1.38); −0.0002 (45.87); −0.0084 (2.11)
Ex. 55, solvent: [DMSO], spectrometer: 399.95 MHz 9.4969 (1.3); 9.3847 (4.47); 7.9522 (0.67); 7.6698 (0.96); 7.664 (1.17); 7.6364 (0.52); 7.615 (1.61); 7.6008 (1.05); 7.5951 (0.94); 7.5792 (0.35); 7.5731 (0.36); 7.507 (3.9); 7.4855 (4.65); 7.4513 (3.32); 7.4447 (3.77); 7.2367 (2.05); 7.2301 (2.11); 7.2153 (1.83); 7.2086 (1.89); 4.9577 (1.05); 4.9518 (1.43); 4.9482 (1.23); 4.8765 (3.22); 4.7971 (5.72); 4.7583 (2.3); 4.7061 (0.96); 4.3904 (2.06); 4.3516 (1.9); 4.3323 (0.37); 4.2925 (0.75); 4.2475 (0.75); 4.2081 (0.32); 4.0563 (5.38); 4.0379 (2.52); 4.0201 (2.62); 4.0023 (0.85); 3.9551 (0.69); 3.8648 (16); 3.6011 (0.36); 3.5766 (15.78); 3.3572 (0.33); 3.3255 (554.45); 2.8905 (5.77); 2.731 (4.53); 2.6751 (0.77); 2.6707 (1.1); 2.666 (0.83); 2.5407 (0.36); 2.524 (1.72); 2.5105 (54.47); 2.5061 (115.62); 2.5015 (158.95); 2.497 (121.97); 2.4927 (65.07); 2.3327 (0.86); 2.3283 (1.14); 2.3238 (0.89); 2.1326 (0.37); 2.1203 (5.45); 1.9886 (10.49); 1.7799 (6.3); 1.7121 (13.9); 1.6499 (0.4); 1.6077 (2.28); 1.5936 (5.52); 1.5872 (5.41); 1.5736 (3.14); 1.5679 (4.32); 1.2928 (0.62); 1.2791 (1.24); 1.2727 (1.44); 1.2583 (0.93); 1.2352 (1.63); 1.2184 (1.97); 1.205 (4.02); 1.1984 (4.28); 1.1924 (4); 1.1846 (1.85); 1.1745 (5.9); 1.1568 (3.09); 1.1023 (0.52); 1.0152 (11.7); 0.9974 (0.34); −0.0002 (0.61)
Ex. 56, solvent: [DMSO], spectrometer: 601.6 MHz 9.4759 (0.64); 9.3699 (3.96); 8.5556 (5.83); 8.5529 (3.5); 8.5482 (3.58); 8.5456 (6.22); 8.4651 (0.81); 8.4626 (0.53); 8.4577 (0.53); 8.4551 (0.83); 7.9522 (0.41); 7.7446 (0.57); 7.5812 (1.4); 7.5194 (2.55); 7.5151 (2.6); 7.4619 (4.25); 7.4476 (4.7); 7.2711 (4.79); 7.2612 (4.76); 7.1362 (0.73); 7.1264 (0.73); 7.1037 (1.56); 7.0993 (1.54); 7.0894 (1.48); 7.0849 (1.45); 5.4328 (2.05); 5.4068 (2.29); 5.0763 (0.44); 5.0253 (2.42); 4.9994 (2.01); 4.0725 (2.43); 4.0467 (1.03); 4.0348 (2.93); 4.023 (2.97); 4.0112 (0.99); 3.9285 (16); 3.3673 (0.36); 3.3234 (775.68); 3.2995 (6.23); 2.8904 (3.65); 2.7311 (2.88); 2.6191 (0.72); 2.6161 (1.53); 2.6131 (2.16); 2.61 (1.53); 2.607 (0.72); 2.5406 (0.65); 2.5377 (0.44); 2.5223 (5.37); 2.5193 (6.39); 2.5162 (5.82); 2.5074 (108.34); 2.5044 (234.17); 2.5013 (320.07); 2.4983 (230.08); 2.4953 (105.4); 2.3916 (0.64); 2.3885 (1.45); 2.3855 (2.03); 2.3824 (1.42); 2.3794 (0.63); 2.0737 (0.79); 1.9885 (12.97); 1.604 (2.16); 1.5948 (4.81); 1.5903 (5.36); 1.5814 (2.18); 1.2674 (0.33); 1.2583 (0.74); 1.2538 (0.79); 1.2441 (0.52); 1.2351 (0.55); 1.2076 (1.71); 1.1984 (3.86); 1.1941 (4.14); 1.1863 (4.31); 1.1745 (7.06); 1.1626 (3.5); 0.0965 (0.4); 0.0052 (3.02); −0.0002 (99.19); −0.0058 (2.91); −0.1001 (0.39)
Ex. 57, solvent: [DMSO], spectrometer: 399.95 MHz 11.5339 (4.33); 9.4933 (1.31); 9.4791 (5.1); 7.7783 (0.46); 7.7659 (1.88); 7.7568 (1.13); 7.7496 (4.1); 7.7332 (1.88); 7.697 (8.58); 7.6917 (3.71); 7.6793 (3.75); 7.6736 (2.13); 7.6497 (0.47); 7.6332 (0.74); 7.6173 (0.48); 7.5851 (3.7); 7.567 (1.83); 7.5617 (2.51); 7.5506 (0.43); 7.5346 (0.34); 7.5192 (0.33); 5.9815 (0.48); 5.9665 (0.79); 5.95 (0.57); 5.9152 (0.52); 5.8999 (0.51); 5.8287 (1.01); 5.8285 (6.59); 5.8124 (6.52); 5.3477 (1.24); 5.3423 (1.27); 4.0562 (1.36); 4.0382 (3.76); 4.0202 (3.91); 4.0025 (1.35); 3.9786 (1.07); 3.6883 (0.81); 3.5728 (0.36); 3.5567 (0.37); 3.5234 (0.37); 3.5028 (0.42); 3.4858 (0.46); 3.4778 (0.41); 3.4639 (0.45); 3.4477 (0.59); 3.4164 (0.76); 3.3245 (1168.23); 3.2622 (0.43); 3.2123 (0.32); 3.1803 (0.58); 3.1683 (0.47); 3.0473 (1.21); 2.9933 (4.69); 2.9063 (0.59); 2.8597 (1.25); 2.8422 (4.92); 2.6749 (3.65); 2.6707 (4.76); 2.6666 (3.51); 2.5505 (1.32); 2.5403 (2.5); 2.5237 (16.88); 2.506 (550.85); 2.5017 (693.41); 2.4974 (500.71); 2.438 (0.61); 2.4143 (0.41); 2.393 (0.38); 2.3369 (10); 2.3286 (4.78); 2.3239 (3.48); 2.2986 (0.44); 2.2881 (0.35); 2.2187 (0.35); 2.1917 (0.47); 2.074 (0.97); 2.0503 (0.97); 1.9889 (16); 1.6079 (2.47); 1.5934 (6.31); 1.5869 (6.86); 1.5737 (3.53); 1.5483 (0.66); 1.5334 (0.56); 1.3133 (0.48); 1.2989 (0.51); 1.2759 (2.83); 1.2618 (6.03); 1.2551 (6.78); 1.2402 (4.56); 1.1923 (4.5); 1.1745 (8.44); 1.1571 (4.12); 0.8537 (0.55); 0.0077 (1.92); 0.0004 (50.97); −0.0002 (51.39); −0.0076 (2.47)
Ex. 58, solvent: [DMSO], spectrometer: 399.95 MHz 11.4625 (0.76); 9.4924 (0.91); 7.7342 (0.69); 7.7279 (0.87); 7.6972 (0.38); 7.6754 (0.52); 7.669 (0.44); 7.5846 (0.89); 7.5628 (0.61); 5.2886 (0.42); 5.2653 (0.38); 5.2629 (0.4); 5.2177 (0.4); 5.2149 (0.4); 5.1751 (0.34); 5.1722 (0.34); 5.0002 (0.7); 4.9854 (0.68); 4.0553 (1.25); 4.0375 (3.8); 4.0197 (3.84); 4.0019 (1.29); 3.3327 (56.56); 2.5244 (0.53); 2.5107 (9.02); 2.5065 (18.16); 2.502 (23.94); 2.4976 (17.52); 2.4933 (8.69); 1.9892 (16); 1.6078 (0.32); 1.5935 (0.8); 1.5866 (0.87); 1.5734 (0.37); 1.2731 (0.38); 1.2595 (0.79); 1.2527 (0.87); 1.2381 (0.4); 1.1924 (4.32); 1.1746 (8.51); 1.1568 (4.22)
Ex. 59, solvent: [DMSO], spectrometer: 399.95 MHz 11.651 (3.43); 9.5701 (3.87); 7.8258 (0.42); 7.8066 (0.45); 7.7856 (1.77); 7.7798 (1.75); 7.7597 (1.67); 7.7539 (1.75); 7.4937 (2.27); 7.4912 (2.53); 7.4879 (2.46); 4.055 (1.17); 4.0364 (16); 4.0195 (2.96); 4.0017 (0.96); 3.3272 (189.39); 3.3038 (1.7); 2.6753 (2.02); 2.6707 (2.77); 2.6662 (2.03); 2.6617 (1); 2.5409 (1.96); 2.538 (2); 2.5241 (10.07); 2.5194 (14.6); 2.5106 (143.21); 2.5062 (290.59); 2.5017 (381.24); 2.4971 (273.16); 2.4927 (130.54); 2.3372 (0.88); 2.3329 (1.89); 2.3284 (2.64); 2.3238 (1.92); 1.9891 (12.1); 1.6247 (1.42); 1.6106 (3.42); 1.6037 (3.59); 1.5904 (1.59); 1.3354 (0.45); 1.2977 (0.37); 1.2887 (1.71); 1.2751 (3.39); 1.2684 (3.63); 1.254 (1.5); 1.2493 (0.86); 1.2349 (1.15); 1.1921 (3.43); 1.1743 (6.77); 1.1565 (3.32); 0.146 (0.95); 0.008 (8.15); −0.0002 (242.95); −0.0085 (7.93); −0.1497 (0.99)
Ex. 60, solvent: [DMSO], spectrometer: 399.95 MHz 7.794 (4.24); 7.7727 (4.24); 7.6351 (0.76); 4.0377 (0.78); 4.0274 (0.64); 4.0196 (1.38); 4.0064 (16); 3.3192 (128.67); 3.2968 (0.7); 2.8209 (1.39); 2.8055 (1.44); 2.6747 (0.95); 2.6701 (1.33); 2.6657 (0.98); 2.5404 (0.79); 2.5235 (3.49); 2.51 (67.6); 2.5057 (137.84); 2.5011 (183.23); 2.4966 (131.99); 2.4922 (63.54); 2.4323 (0.41); 2.414 (0.36); 2.3324 (1.13); 2.3278 (1.54); 2.3234 (1.25); 2.3189 (0.84); 2.2912 (1.59); 2.2752 (1.59); 1.9886 (2.92); 1.8835 (2.17); 1.6149 (0.87); 1.4668 (0.4); 1.449 (0.35); 1.3351 (0.44); 1.2492 (0.66); 1.2339 (0.36); 1.1922 (0.88); 1.1744 (1.71); 1.1566 (0.85); 1.1112 (0.34); 1.0892 (0.48); 1.084 (0.4); 1.0655 (0.87); 1.0372 (4.91); 1.0194 (10.33); 1.0015 (4.75); 0.9043 (4.3); 0.8866 (9.1); 0.8688 (4.15); 0.008 (1.09); −0.0002 (32.33); −0.0085 (1.18)

Ex. 61, solvent: [DMSO], spectrometer: 399.95 MHz 11.5111 (0.37); 11.475 (1.82); 7.8171 (0.36); 7.761 (1.76); 7.7563 (1.78); 7.6607 (0.63); 7.6561 (0.62); 7.6393 (1.64); 7.6344 (1.68); 7.6196 (2.16); 7.5979 (0.65); 4.0388 (7.82); 4.0199 (1.67); 3.3272 (155.76); 3.3046 (0.44); 3.2089 (0.61); 3.0604 (0.48); 2.8649 (0.47); 2.6801 (0.39); 2.6754 (0.85); 2.6708 (1.18); 2.6662 (0.84); 2.6616 (0.37); 2.541 (0.64); 2.5242 (3.65); 2.5194 (6.12); 2.5108 (63.64); 2.5063 (126.44); 2.5017 (165.51); 2.4971 (117.67); 2.4926 (54.8); 2.3375 (0.45); 2.333 (0.89); 2.3285 (1.2); 2.3239 (0.84); 2.3193 (0.4); 1.9892 (1.79); 1.717 (1.85); 1.4686 (0.61); 1.3975 (16); 1.3356 (0.56); 1.3185 (0.45); 1.3025 (0.73); 1.2491 (0.7); 1.2357 (0.51); 1.2144 (1.84); 1.1967 (3.53); 1.179 (1.74); 1.1744 (1.8); 1.1565 (0.59); 0.008 (0.73); −0.0002 (19.27); −0.0085 (0.58)

Ex. 62, solvent: [DMSO], spectrometer: 399.95 MHz 11.4809 (1.28); 7.7806 (1.15); 7.7762 (1.17); 7.6487 (0.33); 7.6426 (0.35); 7.6268 (1.18); 7.6215 (1.31); 7.6147 (1.72); 7.593 (0.33); 4.0556 (0.42); 4.0348 (5.9); 4.0202 (1.98); 4.0022 (0.4); 3.3283 (21.01); 3.1067 (0.99); 2.8649 (5.51); 2.5245 (0.58); 2.511 (9.79); 2.5067 (19.73); 2.5022 (26.27); 2.4977 (19.46); 2.4934 (9.59); 1.9895 (4.55); 1.6728 (1.36); 1.4933 (1.02); 1.3975 (16); 1.1926 (1.27); 1.1748 (2.51); 1.157 (1.23); −0.0002 (2.53)

Ex. 63, solvent: [DMSO], spectrometer: 399.95 MHz 9.6002 (1.23); 7.7269 (1.04); 7.7055 (1.24); 7.6766 (0.93); 7.6704 (0.97); 7.4809 (0.56); 7.4747 (0.53); 7.4597 (0.48); 7.4533 (0.47); 4.8951 (0.42); 4.8795 (0.59); 4.864 (0.43); 4.0855 (4.08); 4.0568 (1.41); 4.039 (4.12); 4.0212 (4.16); 4.0034 (1.43); 3.3262 (2.69); 2.5117 (1.75); 2.5073 (3.52); 2.5028 (4.67); 2.4983 (3.47); 2.4939 (1.71); 1.9898 (16); 1.617 (0.42); 1.6028 (1.05); 1.596 (1.11); 1.5828 (0.47); 1.2947 (0.5); 1.281 (1.05); 1.2745 (1.1); 1.2599 (0.4); 1.1934 (5.01); 1.1756 (9.46); 1.1578 (4.87); 1.0379 (1.17); 1.0225 (1.27); 0.994 (1.27); 0.9787 (1.15); −0.0002 (1.31)

Ex. 64, solvent: [DMSO], spectrometer: 399.95 MHz 11.531 (5.19); 9.4981 (6.09); 8.3176 (0.59); 7.7614 (4.9); 7.7551 (5.67); 7.69 (2.44); 7.6836 (2.05); 7.6681 (3.54); 7.6617 (3.29); 7.588 (6.35); 7.5661 (4.3); 5.5721 (1.17); 5.5509 (3.42); 5.5291 (3.53); 5.5072 (1.24); 4.0553 (0.61); 4.0375 (1.86); 4.0197 (1.88); 4.0019 (0.63); 3.3757 (6.9); 2.6756 (1.2); 2.671 (1.66); 2.6665 (1.24); 2.5379 (1.15); 2.5242 (6.33); 2.5193 (9.89); 2.5108 (89.72); 2.5065 (179.68); 2.5019 (237.24); 2.4974 (175.66); 2.4931 (88.49); 2.3331 (1.22); 2.3287 (1.67); 2.3242 (1.26); 1.989 (7.98); 1.609 (2.14); 1.5947 (5.27); 1.5878 (5.67); 1.5746 (2.44); 1.3977 (16); 1.3122 (0.32); 1.2725 (2.58); 1.2588 (5.23); 1.2521 (5.65); 1.2375 (2.18); 1.1926 (2.19); 1.1748 (4.28); 1.157 (2.11); 0.8854 (0.38); 0.0079 (1.5); −0.0002 (40.02); −0.0083 (1.91)

The intensity of sharp signals correlates with the height of the signals in a printed example of an NMR spectrum in cm and shows the true ratios of the signal intensities. In the case of broad signals, several peaks or the middle of the signal and their relative intensities may be shown in comparison to the most intense signal in the spectrum.

The lists of the $^1$H NMR peaks are similar to the conventional $^1$H NMR printouts and thus usually contain all peaks listed in conventional NMR interpretations.

In addition, like conventional $^1$H NMR printouts, they may show solvent signals, signals of stereoisomers of the target compounds, which likewise form part of the subject-matter of the invention, and/or peaks of impurities.

In the reporting of compound signals in the delta range of solvents and/or water, our lists of $^1$H NMR peaks show the usual solvent peaks, for example peaks of DMSO in DMSO-$d_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help to identify reproduction of our preparation process with reference to "by-product fingerprints".

A person skilled in the art calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional $^1$H NMR interpretation.

Preparation of the Starting Materials

Ethyl 3-(1-chlorocyclopropyl)-1-methyl-1H-pyrazole-5-carboxylate

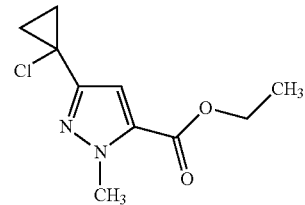

10.16 g (254.2 mmol) of sodium hydride are suspended in 125 ml of tetrahydrofuran p.a. and cooled to −15° C. A solution of 15.0 g (127.1 mmol) of 1-(1-chlorocyclopropyl)ethanone in 25 ml of tetrahydrofuran p.a. is added dropwise to this suspension. The suspension is stirred at −15° C. for 2 h, and 37.12 g (254.2 mmol) of diethyl oxalate are then added. After 3 h at room temperature, the reaction is quenched with ice-water. The aqueous phase is extracted repeatedly with ethyl acetate. The combined organic phases are washed with saturated sodium chloride solution, dried over sodium sulphate and filtered. The solvent is removed on a rotary evaporator under reduced pressure.

The residue is dissolved in 150 ml of ethanol p.a. and boiled under reflux. 36.09 g (254.2 mmol) of methylhydrazine sulphate are added to the mixture at reflux, and the mixture is boiled at reflux for a further 4 h. After cooling, the reaction is concentrated under reduced pressure on a rotary evaporator, and the residue obtained in this manner is taken up in a mixture of water and ethyl acetate. The aqueous phase is extracted repeatedly with ethyl acetate. The combined organic phases are washed with saturated sodium chloride solution, dried over sodium sulphate and filtered. The solvent is removed on a rotary evaporator under reduced pressure. The crude product is purified by column chromatography. This gives 4.34 g (15%) of ethyl 3-(1-chlorocyclopropyl)-1-methyl-1H-pyrazole-5-carboxylate.

$^1$H-NMR (300 MHz, $d_1$-chloroform) δ=6.89 (s, 1H), 4.36 (q, 2H), 4.11 (s, 3H), 1.35 (t, 3H) ppm;

Ethyl 4-chloro-3-(1-chlorocyclopropyl)-1-methyl-1H-pyrazole-5-carboxylate

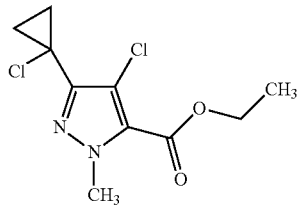

500 mg (2.19 mmol) of ethyl 3-(1-chlorocyclopropyl)-1-methyl-1H-pyrazole-5-carboxylate are dissolved in 10 ml of N,N-dimethylformamide p.a., and 438 mg (3.28 mmol)) of N-chlorosuccinimide are added. The reaction mixture is heated at 80° C. for 15. The cooled reaction solution is diluted with water and extracted twice with ethyl acetate. The combined organic phases are washed with saturated sodium chloride solution, dried over sodium sulphate and filtered. The solvent is removed under reduced pressure on a rotary evaporator. The crude product is filtered through silica gel and eluted with ethyl acetate. This gives 517 mg (80%) of ethyl 4-chloro-3-(1-chlorocyclopropyl)-1-methyl-1H-pyrazole-5-carboxylate in a purity of 89%.

$^1$H-NMR (400 MHz, $d_6$-DMSO): δ=4.35 (q, 2H), 4.04 (s, 3H), 1.42-1.46 (m, 2H), 1.31-1.38 (m, 5H) ppm.

HPLC-MS$^{a)}$: log P=3.52, mass (m/z)=263 [M+H]$^+$.

4-Chloro-3-(1-chlorocyclopropyl)-1-methyl-1H-pyrazole-5-carboxylic acid

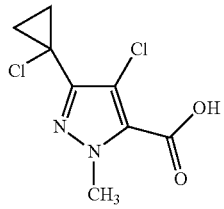

517 mg (1.76 mmol) of ethyl 4-chloro-3-(1-chlorocyclopropyl)-1-methyl-1H-pyrazole-5-carboxylate (purity 89%) are dissolved in 10 ml of ethanol p.a. 3.5 ml (3.5 mmol) of 1 N aqueous sodium hydroxide solution are then added to the solution, and the mixture is stirred at room temperature for 16 h. The reaction mixture is acidified by addition of 1 N hydrochloric acid. The aqueous phase is extracted twice with ethyl acetate. The combined organic phases are washed with saturated sodium chloride solution, dried over sodium sulphate and filtered. The solvent is removed under reduced pressure on a rotary evaporator. This gives 422 mg (99%) of 4-chloro-3-(1-chlorocyclopropyl)-1-methyl-1H-pyrazole-5-carboxylic acid.

$^1$H-NMR (400 MHz, $d_6$-DMSO): δ=4.02 (s, 3H), 1.31-1.42 (m, 4H) ppm.

HPLC-MS$^{a)}$: log P=1.90, mass (m/z)=235 [M+H]$^+$.

Ethyl 3-(1-fluorocyclopropyl)-1-methyl-1H-pyrazole-5-carboxylate

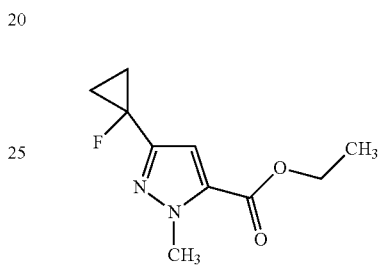

Ethyl 3-(1-fluorocyclopropyl)-1-methyl-1H-pyrazole-5-carboxylate is prepared from 1-(1-fluorocyclopropyl)ethanone analogously to the process described in the synthesis of ethyl 3-(1-chlorocyclopropyl)-1-methyl-1H-pyrazole-5-carboxylate.

$^1$H-NMR (300 MHz, $d_1$-chloroform) δ=6.90 (s, 1H), 4.34 (q, 2H), 4.13 (s, 3H), 1.37 (t, 3H) ppm;

Ethyl 4-chloro-3-(1-fluorocyclopropyl)-1-methyl-1H-pyrazole-5-carboxylate

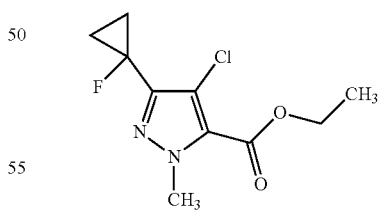

The preparation was carried out analogously to the preparation of ethyl 4-chloro-3-(1-chlorocyclopropyl)-1-methyl-1H-pyrazole-5-carboxylate using ethyl 3-(1-fluorocyclopropyl)-1-methyl-1H-pyrazole-5-carboxylate and 3 eq of N-chlorosuccinimide $^1$H-NMR (400 MHz, $d_6$-DMSO): δ=4.36 (q, 2H), 4.06 (s. 3H), 1.38-1.44 (m, 2H), 1.33 (t, 3H), 1.04-1.09 (m, 2H) ppm.

HPLC-MS$^{a)}$: log P=3.07, mass (m/z)=247 [M+H]$^+$.

4-Chloro-3-(1-fluorocyclopropyl)-1-methyl-1H-pyrazole-5-carboxylic acid

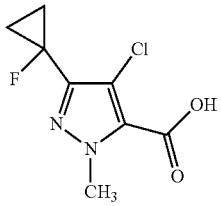

The preparation was carried out analogously to the preparation of 4-chloro-3-(1-chlorocyclopropyl)-1-methyl-1H-pyrazole-5-carboxylic acid using ethyl 3-(1-fluorocyclopropyl)-1-methyl-1H-pyrazole-5-carboxylate and 5.0 eq of sodium hydroxide in methanol.

$^1$H-NMR (400 MHz, d$_6$-DMSO): δ=4.05 (s, 3H), 1.37-1.43 (m, 2H), 1.05-1.09 (m, 2H) ppm.

HPLC-MS$^{a)}$: log P=3.07, mass (m/z)=219 [M+H]$^+$.

Methyl 2-chloro-5-({[1-methyl-3-(pentafluoroethyl)-4-(trifluoromethyl)-1H-pyrazol-5-yl]carbonyl}amino)benzoate

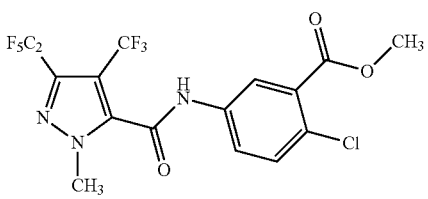

4.0 g (12.8 mmol) of 1-methyl-3-(pentafluoroethyl)-4-(trifluoromethyl)-1H-pyrazole-5-carboxylic acid are suspended in 50 ml of dichloromethane. 0.02 ml of N,N-dimethylformamide and 3.54 ml (38.4 mmol) of oxalyl chloride are then added in succession. The reaction mixture is then stirred first at room temperature for 30 minutes and then under reflux for 30 minutes. The solvent is removed under reduced pressure on a rotary evaporator. The 1-methyl-3-(pentafluoroethyl)-4-(trifluoromethyl)-1H-pyrazole-5-carbonyl chloride formed is used for the subsequent synthesis step without further purification.

A solution of 4.24 g (12.8 mmol) of 1-methyl-3-(pentafluoroethyl)-4-(trifluoromethyl)-1H-pyrazole-5-carbonyl chloride in 25 ml of dichloromethane p.a. is added to a suspension of 2.38 g (12.8 mmol) of methyl 5-amino-2-chlorobenzoate and 2.57 g (19.2 mmol) of silver(I) cyanide in 50 ml of dichlormethane p.a., and the mixture is stirred at room temperature for 16 h. The suspension is then filtered through silica gel and the product is eluted using a mixture of cyclohexane and ethyl acetate (1:1). The organic phase is washed successively three times with 6N hydrochloric acid and twice with saturated sodium chloride solution. The organic phase is then dried over sodium sulphate, filtered and concentrated on a rotary evaporator under reduced pressure. This gives 5.75 g (93%) of methyl 2-chloro-5-({[1-methyl-3-(pentafluoroethyl)-4-(trifluoromethyl)-1H-pyrazol-5-yl]carbonyl}amino) benzoate.

$^1$H-NMR (400 MHz, d$_3$-acetonitrile): δ=9.33 (s, 1H), 8.14 (d, 1H), 7.72 (dd, 1H), 7.54 (d, 1H), 3.98 (s, 3H), 3.90 (s, 3H) ppm.

HPLC-MS$^{a)}$: log P=4.05, mass (m/z)=480 [M+H]$^+$.

2-Chloro-5-({[1-methyl-3-(pentafluoroethyl)-4-(trifluoromethyl)-1H-pyrazol-5-yl]carbonyl}amino)benzenecarboxylic acid

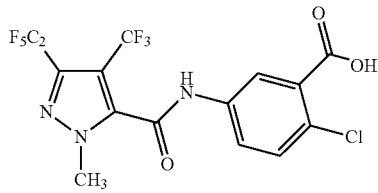

5.75 g (11.9 mmol) of methyl 2-chloro-5-({[1-methyl-3-(pentafluoroethyl)-4-(trifluoromethyl)-1H-pyrazol-5-yl]carbonyl}amino)benzoate are dissolved in 30 ml of methanol p.A., and 15.0 ml (30.0 mmol) of 2 N aqueous sodium hydroxide solution are then added. The reaction mixture is stirred at room temperature for 16 hours. The reaction solution is acidified carefully with 6 N hydrochloric acid, and the aqueous phase is then extracted three times with ethyl acetate. The combined organic phases are washed once with saturated sodium chloride solution, dried over sodium sulphate and filtered. The solvent is removed under reduced pressure on a rotary evaporator. This gives 5.57 g of 2-chloro-5-({[1-methyl-3-(pentafluoroethyl)-4-(trifluoromethyl)-1H-pyrazol-5-yl]carbonyl}amino)benzenecarboxylic acid as a colourless solid.

$^1$H-NMR (400 MHz, d$_3$-acetonitrile): δ=9.17 (s, 1H), 8.11 (d, 1H), 7.73 (dd, 1H), 7.52 (d, 1H), 3.98 (s, 3H) ppm.

HPLC-MS$^{a)}$: log P=3.18, mass (m/z)=466 [M+H]$^+$.

Ethyl 3,4-bis(trifluoromethyl)-1H-pyrazole-5-carboxylate

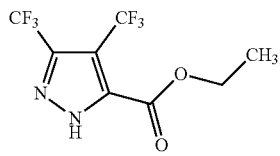 [SMILES: CCOC(=O)c1[nH]nc(C(F)(F)F)c1C(F)(F)F]

Under protective gas, 7.57 g (63.0 mmol) of diazoethyl acetate are initially charged in 200 ml of diethyl ether, and the temperature of the mixture is adjusted to −70° C. 20.4 g (126 mmol) of hexafluorobutyne are then introduced into the cooled solution. The reaction mixture is slowly warmed to room temperature and stirred for 16 hours. The solvent is then removed on a rotary evaporator. This gives 17.0 g of ethyl 3,4-bis(trifluoromethyl)-1H-pyrazole-5-carboxylate (98%) as a yellow oil.

$^1$H-NMR (400 MHz, d$_3$-acetonitrile): δ=4.42 (q, 2H), 1.38 (t, 3H) ppm.

GC-MS: retention time 3.48 min; mass (m/z)=276 [M]$^+$.

1-Methyl-3,4-bis(trifluoromethyl)-1H-pyrazole-5-carboxylic acid

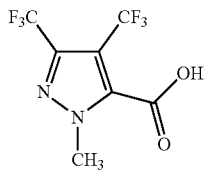

3.0 g (10.9 mmol) of ethyl 3,4-bis(trifluoromethyl)-1H-pyrazole-5-carboxylate and 4.5 g (32.6 mmol) of potassium carbonate are suspended in 70 ml of acetone, and 1.35 ml of iodomethane (21.7 mmol) are added. The reaction mixture is stirred at room temperature overnight. 54 ml (108 mmol) of 2 N aqueous sodium hydroxide solution are added to the suspension. The solution is then stirred at room temperature overnight. The reaction mixture is diluted with water, and most of the acetone is removed on a rotary evaporator under reduced pressure. The residue is adjusted to pH 2-3 using 1 M hydrochloric acid. The aqueous reaction solution is extracted twice with ethyl acetate. The combined organic phases are dried over magnesium sulphate, filtered and concentrated under reduced pressure on a rotary evaporator. This gives 2.7 g of 1-methyl-3,4-bis(trifluoromethyl)-1H-pyrazole-5-carboxylic acid (84%; purity 88%) as a brown solid.

$^1$H-NMR (400 MHz, $d_3$-acetonitrile): δ=4.12 (s, 3H) ppm.

HPLC-MS log P=1.47, mass (m/z)=263 [M+H]$^+$.

Methyl 2-chloro-5-(methylamino)benzoate

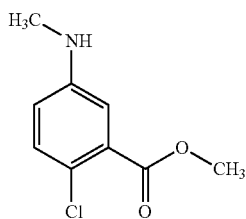

55.0 g (296 mmol) of methyl 2-chloro-5-aminobenzoate and 49.1 g (356 mmol) of potassium carbonate are suspended in 500 ml of acetonitrile p.a. 22.1 ml (356 mmol) of methyl iodide are added dropwise to the reaction mixture. The suspension is then boiled under reflux for 3 hours. After cooling, the reaction mixture is filtered. The filtrate is diluted with water. The aqueous phase is extracted twice with ethyl acetate. The combined organic phases are dried over sodium sulphate and filtered. The solvent is removed under reduced pressure on a rotary evaporator. The crude product is purified by column chromatography. This gives 30.0 g (51%) of methyl 2-chloro-5-(methylamino)benzoate.

$^1$H-NMR (300 MHz, $d_1$-chloroform) δ=7.21 (d, 1H), 7.00 (d, 1H), 6.63 (d, 1H), 3.90 (s, 3H), 2.86 (s, 3H) ppm.

5-Amino-2-chloro-N-(1-cyanocyclopropyl)benzamide

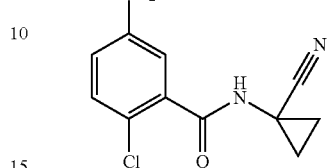

3.20 g (15.9 mmol) of 2-chloro-5-nitrobenzoic acid are initially charged in 50 ml of dichloromethane p.a., and 0.06 ml of N,N-dimethylformamide p.a. is added. 2.08 ml (23.8 mmol) of oxalyl chloride are then added to the reaction mixture. After 3 h at RT, the reaction mixture is concentrated under reduced pressure on a rotary evaporator. The crude product (2-chloro-5-nitrobenzoyl chloride) is reacted further without further purification.

2.36 g (19.8 mmol) of 1-aminocyclopropanecarbonitrile hydrochloride is suspended in 70 ml of chloroform p.a. With ice cooling, 6.93 ml (39.7 mmol) of N-ethyldiisopropylamine are added to the suspension. A solution of 3.50 g (15.9 mmol) of 2-chloro-5-nitrobenzoyl chloride in 5 ml of chloroform p.a. is then added dropwise to the cooled mixture. The reaction mixture is heated at 50° C. (oil bath temperature) for 4 h. The reaction mixture is then stirred at room temperature for another 12 h.

The reaction mixture is concentrated under reduced pressure on a rotary evaporator, and the residue is taken up in ethyl acetate. The organic phase is washed twice with 0.5 N hydrochloric acid, dried over sodium sulphate and filtered. The solvent is removed under reduced pressure on a rotary evaporator. This gives 3.70 g (84%) of 2-chloro-N-(1-cyanocyclopropyl)-5-nitrobenzamide.

$^1$H-NMR (400 MHz, $d_6$-DMSO): δ=9.59 (s, 1H), 8.36 (d, 1H), 8.31 (dd, 1H), 7.85 (d, 1H), 1.55-1.61 (m, 2H), 1.32-1.37 (m, 2H) ppm.

HPLC-MS$^{a)}$: log P=1.52, mass (m/z)=266 [M+H]$^+$.

3.15 g of iron powder are suspended in 18 ml of 5% strength acetic acid, and a solution of 3.0 g of 2-chloro-N-(1-cyanocyclopropyl)-5-nitrobenzamide in a mixture of 25 ml of ethyl acetate and 22.6 ml of glacial acetic acid is added. During the addition, the internal temperature is kept below 45° C. The reaction mixture is stirred at room temperature for 14 hours and then filtered through Celite. The filtrate is diluted with water, and the aqueous phase is extracted three times with ethyl acetate. The combined organic phases are washed twice with a saturated sodium chloride solution, dried over magnesium sulphate, filtered and concentrated on a rotary evaporator under reduced pressure. The crude product is triturated with a mixture of three parts of cyclohexane and one part of ethyl acetate, and the solid is filtered off. This gives 2.0 g (71%) of 5-amino-2-chloro-N-(1-cyanocyclopropyl)benzamide.

$^1$H-NMR (400 MHz, $d_6$-DMSO): δ=9.20 (s, 1H), 7.07 (d, 1H), 6.62 (dd, 1H), 6.57 (d, 1H), 1.51-1.57 (m, 2H), 1.17-1.24 (m, 2H) ppm.

HPLC-MS$^{a)}$: log P=0.82, mass (m/z)=236 [M+H]$^+$.

1-Methyl-4-(methylsulphanyl)-3-(pentafluoroethyl)-1H-pyrazole-5-carboxylic acid

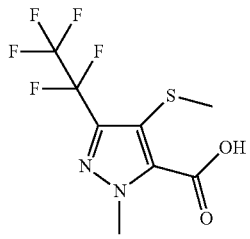

8.0 g (27.7 mmol) of 1-methyl-4-nitro-3-(pentafluoroethyl)-1H-pyrazole-5-carboxylic acid [preparation analogously to J. Med. Chem. 1987, 30, 91-96] are dissolved in 100 ml of dichloromethane. 50 µl of N,N-dimethylformamide and 10.5 g (83.0 mmol) of oxalyl chloride are added successively to the solution. After 0.5 h at room temperature, the reaction is heated under reflux for 0.5 h. The reaction mixture is cooled to room temperature. The solvents and excess oxalyl chloride are removed on a rotary evaporator under reduced pressure. The residue is dissolved in chloroform p.a. and slowly added dropwise to a suspension of 5.56 g (41.5 mmol) of silver(I) cyanide, 100 ml of chloroform p.a. and 56 ml of methanol p.a. The mixture is heated under reflux for 8 h and then cooled to room temperature. The reaction mixture is filtered through a short silica gel column, and the column is rinsed with dichloromethane. The solvents are removed on a rotary evaporator under reduced pressure.

This gives 8.5 g of methyl 1-methyl-4-nitro-3-(pentafluoroethyl)-1H-pyrazole-5-carboxylate. The crude product is used for the next reaction without further purification.

$^1$H-NMR (600 MHz, $d_6$-DMSO): δ=4.16 (s, 3H), 3.93 (s, 3H) ppm.

HPLC-MS$^{a)}$: log P=3.18, mass (m/z)=304 [M+H]$^+$.

8.5 g (28.0 mmol) of methyl 1-methyl-4-nitro-3-(pentafluoroethyl)-1H-pyrazole-5-carboxylate and 850 mg of palladium on carbon (10% palladium) are suspended in 100 ml of methanol. The autoclave is inertized with nitrogen and the reaction mixture is then stirred under a hydrogen atmosphere of 5 bar. After 22 h at RT, the mixture is filtered through Celite and the solvent is removed under reduced pressure on a rotary evaporator. The crude product is taken up in dichloromethane and filtered through sodium sulphate. The dichloromethane is then removed under reduced pressure on a rotary evaporator.

This gives 6.7 g (86%) of methyl 4-amino-1-methyl-3-(pentafluoroethyl)-1H-pyrazole-5-carboxylate.

$^1$H-NMR (600 MHz, $d_6$-DMSO): δ=5.32 (s, 2H), 4.07 (s, 3H), 3.86 (s, 3H) ppm.

HPLC-MS$^{a)}$: log P=2.52, mass (m/z)=274 [M+H]$^+$.

2.0 g (7.32 mmol) of methyl 4-amino-1-methyl-3-(pentafluoroethyl)-1H-pyrazole-5-carboxylate and 1.38 g (14.6 mmol) dimethyl disulphide are dissolved in 14 ml of acetonitrile p.a. A solution of 1.26 g (11.0 mmol) of tert-butyl nitrite in 5 ml of acetonitrile p.a. is slowly added dropwise to this mixture. After the addition has ended, the reaction mixture is stirred at room temperature for another 1 h. The reaction mixture is then poured into 1 N hydrochloric acid. The aqueous phase is extracted three times with ethyl acetate. The combined organic phases are washed twice with saturated sodium chloride solution, dried over magnesium sulphate and filtered. The solvents are removed on a rotary evaporator under reduced pressure.

This gives 2.0 g (72%) of methyl 1-methyl-4-(methylsulphanyl)-3-(pentafluoroethyl)-1H-pyrazole-5-carboxylate as a 8:2 mixture of the desired product and the by-product methyl 1-methyl-3-(pentafluoroethyl)-1H-pyrazole-5-carboxylate.

$^1$H-NMR (400 MHz, $d_6$-DMSO): δ=4.12 (s, 3H), 3.94 (s, 3H), 2.34 (s, 3H) ppm.

HPLC-MS$^{a)}$: log P=3.51, mass (m/z)=305 [M+H]$^+$.

3.0 g of methyl 1-methyl-4-(methylsulphanyl)-3-(pentafluoroethyl)-1H-pyrazole-5-carboxylate are dissolved in 16 ml of methanol p.a. 16.5 ml of 2 N aqueous sodium hydroxide solution are then added to the solution, and the mixture is stirred at room temperature for 16 h. The reaction mixture is diluted with ethyl acetate and then washed with 100 ml of 1 N hydrochloric acid. The acidic aqueous phase is extracted twice with ethyl acetate. The combined organic phases are washed with saturated sodium chloride solution, dried over sodium sulphate and filtered. The solvents are removed on a rotary evaporator under reduced pressure.

This gives 2.5 g (90%) of 1-methyl-4-(methylsulphanyl)-3-(pentafluoroethyl)-1H-pyrazole-5-carboxylic acid as an about 8:2 mixture of the desired product and the by-product 1-methyl-3-(pentafluoroethyl)-1H-pyrazole-5-carboxylic acid.

$^1$H-NMR (400 MHz, $d_6$-DMSO): δ=4.12 (s, 3H), 3.94 (s, 3H), 2.34 (s, 3H) ppm.

HPLC-MS log P=3.51, mass (m/z)=305 [M+H]$^+$.

Biological Examples

A. Activity of the Compounds

*Phaedon* Test (PHAECO Spray Treatment)
Solvents:
  78.0 parts by weight of acetone
  1.5 parts by weight of dimethylformamide
Emulsifier:
  0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration. Discs of Chinese cabbage leaves (*Brassica pekinensis*) are sprayed with an active compound preparation of the desired concentration and, after drying, populated with larvae of the mustard beetle (*Phaedon cochleariae*).

After a time of 7 days, the efficacy in % is determined. 100% means that all of the beetle larvae have been killed; 0% means that none of the beetle larvae have been killed.

In this test, for example, the following compounds of the Preparation Examples show an efficacy of 100% at an application rate of 500 g/ha: 1, 2, 3, 4, 5, 6, 7, 8, 9, 10

*Spodoptera frugiperda* Test (SPODFR Spray Treatment)
Solvents:
  78.0 parts by weight of acetone
  1.5 parts by weight of dimethylformamide
Emulsifier:
  0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration. Leaf discs of maize (*Zea mays*) are sprayed with an active compound formulation of the desired concentration and, after drying, populated with caterpillars of the armyworm (*Spodoptera frugiperda*).

After 7 days, the efficacy in % is determined. 100% means that all of the caterpillars have been killed; 0% means that none of the caterpillars have been killed.

In this test, for example, the following compound of the Preparation Examples shows an efficacy of 83% at an application rate of 500 g/ha: 7

In this test, for example, the following compounds of the Preparation Examples show an efficacy of 100% at an application rate of 500 g/ha: 2, 4, 5, 6, 8, 9, 10

*Myzus* test (Myzupe spray treatment)

Solvents:
 78 parts by weight of acetone
 1.5 parts by weight of dimethylformamide
Emulsifier:
 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration. Discs of Chinese cabbage leaves (*Brassica pekinensis*) infested by all stages of the green peach aphid (*Myzus persicae*) are sprayed with an active compound preparation of the desired concentration.

After 6 days, the efficacy in % is determined. 100% means that all of the aphids have been killed; 0% means that none of the aphids have been killed.

In this test, for example, the following compounds of the Preparation Examples show an efficacy of 90% at an application rate of 500 g/ha: 5, 9

In this test, for example, the following compounds of the Preparation Examples show an efficacy of 100% at an application rate of 500 g/ha: 2, 4, 6, 8, 10

*Tetranychus* Test, OP-Resistant (TETRUR Spray Treatment)

Solvents:
 78.0 parts by weight of acetone
 1.5 parts by weight of dimethylformamide
Emulsifier:
 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration. Discs of bean leaves (*Phaseolus vulgaris*) which are infested by all stages of the greenhouse red spider mite (*Tetranychus urticae*) are sprayed with an active compound preparation of the desired concentration.

After a time of 6 days, the efficacy in % is determined. 100% means that all of the spider mites have been killed; 0% means that none of the spider mites have been killed.

In this test, for example, the following compound of the Preparation Examples shows an efficacy of 90% at an application rate of 500 g/ha: 10

In this test, for example, the following compounds of the Preparation Examples show an efficacy of 100% at an application rate of 500 g/ha: 1, 2, 3, 4, 5, 6, 7, 8, 9.

*Ctenocephalides felis* Oral (CTECFE)

Solvent: 1 part by weight of dimethyl sulphoxide

For the purpose of producing a suitable preparation of active compound, 10 mg of active compound are mixed with 0.5 ml of dimethyl sulphoxide. A portion of the concentrate is diluted with citrated cattle blood, and the desired concentration is prepared.

About 20 unfed adult fleas (*Ctenocephalides felis*) are placed into a chamber which is closed at the top and bottom with gauze. A metal cylinder whose bottom end is closed with parafilm is placed onto the chamber. The cylinder contains the blood/active compound preparation, which can be taken up by the fleas through the parafilm membrane. After 2 days, the kill in % is determined. 100% means that all of the fleas have been killed; 0% means that none of the fleas have been killed.

In this test, for example, the following compound of the Preparation Examples shows, at an application rate of 100 ppm, an effect of 80%: 7

In this test, for example, the following compounds of the Preparation Examples show, at an application rate of 100 ppm, an effect of 100%: 2, 6, 8, 9, 10

*Lucilia cuprina* Test (LUCICU)

Solvent: dimethyl sulphoxide

To produce a suitable preparation of active compound, 10 mg of active compound are mixed with 0.5 ml of dimethyl sulphoxide, and the concentrate is diluted with water to the desired concentration. Vessels containing horse meat treated with the active compound preparation of the desired concentration are populated with about 20 *Lucilia cuprina* larvae.

After 2 days, the kill in % is determined. 100% means that all larvae have been killed; 0% means that no larvae have been killed.

In this test, for example, the following compounds of the Preparation Examples show an efficacy of 100% at an application rate of 100 ppm: 6, 7, 8, 9, 10

*Musca domestica* Test (MUSCDO)

Solvent: dimethyl sulphoxide

To produce a suitable preparation of active compound, 10 mg of active compound are mixed with 0.5 ml of dimethyl sulphoxide, and the concentrate is diluted with water to the desired concentration. Vessels containing a sponge treated with the active compound preparation of the desired concentration are populated with adult *Musca domestica*.

After 2 days, the kill in % is determined. 100% means that all of the flies have been killed; 0% means that none of the flies have been killed.

In this test, for example, the following compounds of the Preparation Examples show an efficacy of 100% at an application rate of 100 ppm: 6, 7, 8, 10

*Boophilus microplus* Test (BOOPMI Injection)

Solvent: dimethyl sulphoxide

To produce a suitable preparation of active compound, 10 mg of active compound are mixed with 0.5 ml of solvent, and the concentrate is diluted with solvent to the desired concentration. The active compound solution is injected into the abdomen (*Boophilus microplus*), and the animals are transferred into dishes and stored in a climate-controlled room. The activity is assessed by laying of fertile eggs.

After 7 days, the efficacy in % is determined 100% means that none of the ticks has laid any fertile eggs.

In this test, for example, the following compounds of the Preparation Examples show an efficacy of 100% at an application rate of 20 µg/animal: 2, 6, 7, 8, 9, 10

*Boophilus microplus* Test (DIP)

Test animals: adult engorged *Boophilus microplus* females of the SP-resistant Parkhurst strain Solvent: dimethyl sulphoxide 10 mg of active compound are dissolved in 0.5 ml of dimethyl sulphoxide. For the purpose of preparing a suitable formulation, the active compound solution is diluted with water to the concentration desired in each case.

This active compound preparation is pipetted into tubes. 8-10 ticks are transferred into a further tube with holes. The tube is immersed into the active compound formulation, and all ticks are completely wetted. After the liquid has run off, the ticks are transferred to filter discs in plastic dishes and kept in a climatized room. The activity is assessed after 7 days by laying of fertile eggs. Eggs whose fertility is not outwardly visible are stored in glass tubes in a climate-controlled cabinet until the larvae hatch. An efficacy of 100% means that none of the ticks has laid any fertile eggs.

In this test, for example, the following compounds of the Preparation Examples show an efficacy of 100% at an application rate of 100 ppm: 6, 8, 9, 10

*Amblyomma hebaraeum* Test (AMBYHE)
Solvent: dimethyl sulphoxide

To produce a suitable preparation of active compound, 10 mg of active compound are mixed with 0.5 ml of dimethyl sulphoxide, and the concentrate is diluted with water to the desired concentration.

Tick nymphs (*Amblyomma hebraeum*) are placed into perforated plastic beakers and immersed in the desired concentration for one minute. The ticks are transferred on filter paper into a Petri dish and stored in a climate-controlled cabinet.

After 42 days, the kill in % is determined. 100% means that all of the ticks have been killed; 0% means that none of the ticks have been killed.

In this test, for example, the following compound of the Preparation Examples shows, at an application rate of 100 ppm, an effect of 100%: 10

B. Biological Comparative Tests

*Spodoptera frugiperda* Test (SPODFR Spray Treatment)
Solvents:
    78.0 parts by weight of acetone
    1.5 parts by weight of dimethylformamide
Emulsifier:
    0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration (in g/ha).

Leaf discs of maize (*Zea mays*) are sprayed with an active compound formulation of the desired concentration and, after drying, populated with caterpillars of the armyworm (*Spodoptera frugiperda*).

After the desired period of time, the effect in % is determined 100% means that all of the caterpillars have been killed; 0% means that none of the caterpillars have been killed.

In this test, for example, the following compounds of the Preparation Examples show superior efficacy to the prior art: see table

*Myzus* Test (MYZUPE Spray Treatment)
Solvents:
    78.0 parts by weight of acetone
    1.5 parts by weight of dimethylformamide
Emulsifier:
    0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration (in g/ha).

Discs of Chinese cabbage leaves (*Brassica pekinensis*) infested by all stages of the green peach aphid (*Myzus persicae*) are sprayed with an active compound preparation of the desired concentration.

After the desired period of time, the effect in % is determined 100% means that all of the aphids have been killed; 0% means that none of the aphids have been killed.

In this test, for example, the following compounds of the Preparation Examples show superior efficacy to the prior art: see table

*Phaedon* Test (PHAECO Spray Treatment)
Solvents:
    78.0 parts by weight of acetone
    1.5 parts by weight of dimethylformamide
Emulsifier:
    0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration (in g/ha).

Discs of Chinese cabbage leaves (*Brassica pekinensis*) are sprayed with an active compound preparation of the desired concentration and, after drying, populated with larvae of the mustard beetle (*Phaedon cochleariae*).

After the desired period of time, the effect in % is determined 100% means that all of the beetle larvae have been killed; 0% means that none of the beetle larvae have been killed.

In this test, for example, the following compounds of the Preparation Examples show superior efficacy to the prior art: see table

*Tetranychus* Test, OP-Resistant (TETRUR Spray Treatment)
Solvents:
    78.0 parts by weight of acetone
    1.5 parts by weight of dimethylformamide
Emulsifier:
    0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration (in g/ha).

Discs of bean leaves (*Phaseolus vulgaris*) which are infested by all stages of the greenhouse red spider mite (*Tetranychus urticae*) are sprayed with an active compound preparation of the desired concentration.

After the desired period of time, the effect in % is determined 100% means that all of the spider mites have been killed; 0% means that none of the spider mites have been killed.

In this test, for example, the following compounds of the Preparation Examples show superior efficacy to the prior art: see table

*Phaedon cochleariae* Spray Test (PHAECO)
Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration (in ppm). If the addition of ammonium salts or/and penetrants is required, these are in each case added in a concentration of 1000 ppm to the solution of the preparation.

Cabbage leaves (*Brassica oleracea*) are sprayed with an active compound preparation of the desired concentration and populated with larvae of the mustard beetle (*Phaedon cochleariae*).

After the desired period of time, the kill in % is determined 100% means that all of the beetle larvae have been killed; 0% means that none of the beetle larvae have been killed.

In this test, for example, the following compound of the Preparation Examples shows superior efficacy to the prior art: see table

*Plutella xylostella* Spray Test (PLUTMA)
Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration (in ppm). If the addition of ammonium salts or/and penetrants is required, these are in each case added in a concentration of 1000 ppm to the solution of the preparation.

Cabbage leaves (*Brassica oleracea*) are sprayed with an active compound preparation of the desired concentration and infected with larvae of the diamondback moth (*Plutella xylostella*).

After the desired period of time, the kill in % is determined 100% means that all caterpillars have been killed; 0% means that none of the caterpillars have been killed.

In this test, for example, the following compound of the Preparation Examples shows superior efficacy to the prior art: see table

*Spodoptera frugiperda* Spray Test (SPODFR)
Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration (in ppm). If the addition of ammonium salts or/and penetrants is required, these are in each case added in a concentration of 1000 ppm to the solution of the preparation.

Cotton leaves (*Gossypium hirsutum*) are sprayed with an active compound formulation of the desired concentration and populated with caterpillars of the armyworm (*Spodoptera frugiperda*).

After the desired period of time, the kill in % is determined 100% means that all caterpillars have been killed; 0% means that none of the caterpillars have been killed.

In this test, for example, the following compounds of the Preparation Examples show superior efficacy to the prior art: see table

*Heliothis armigera* Spray Test (HELIAR)
Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration (in ppm). If the addition of ammonium salts or/and penetrants is required, these are in each case added in a concentration of 1000 ppm to the solution of the preparation.

Cotton plants (*Gossypium hirsutum*) are sprayed with an active compound formulation of the desired concentration and, after drying, populated with caterpillars of the cotton bollworm (*Heliothis armigera*). After the desired period of time, the kill in % is determined 100% means that all caterpillars have been killed; 0% means that none of the caterpillars have been killed.

In this test, for example, the following compound of the Preparation Examples shows superior efficacy to the prior art: see table

*Tetranychus urticae* Spray Test, OP-Resistant (TETRUR)
Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration (in ppm). If the addition of ammonium salts or/and penetrants is required, these are in each case added in a concentration of 1000 ppm to the solution of the preparation.

Bean plants (*Phaseolus vulgaris*) which are heavily infested by all stages of the greenhouse red spider mite (*Tetranychus urticae*) are sprayed with an active compound preparation of the desired concentration.

After the desired period of time, the effect in % is determined 100% means that all of the spider mites have been killed; 0% means that none of the spider mites have been killed.

In this test, for example, the following compounds of the Preparation Examples show superior efficacy to the prior art: see table

*Nilaparvata lugens* Spray Test (NILALU)
Solvents:
52.5 parts by weight of acetone
7 parts by weight of dimethylformamide
Emulsifier:
0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration. If the addition of ammonium salts or/and penetrants is required, these are in each case added in a concentration of 1000 ppm to the solution of the preparation.

Rice plants (*Oryza sativa*) are sprayed with an active compound preparation of the desired concentration and then populated with larvae of the brown planthopper (*Nilaparvata lugens*).

After the desired period of time, the effect in % is determined 100% means that all of the planthoppers have been killed; 0% means that none of the planthoppers have been killed.

In this test, for example, the following compounds of the Preparation Examples show superior efficacy to the prior art: see table

*Frankliniella occidentalis* Spray Test (FRANOC)
Solvents:
52.5 parts by weight of acetone
7 parts by weight of dimethylformamide
Emulsifier:
0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration. If the addition of ammonium salts or/and penetrants is required, these are in each case added in a concentration of 1000 ppm to the solution of the preparation. Discs of leaves of common beans (*Phaseolus vulgaris*) are sprayed with an active compound preparation of the desired concentration and then infected with a mixed thrips population (*Frankliniella occidentalis*).

After the desired period of time, the effect in % is determined 100% means that all thrips have been killed; 0% means that none of the thrips have been killed.

In this test, for example, the following compounds of the Preparation Examples show superior efficacy to the prior art: see table

*Liriomyza trifolii* Spray Test (LIRITR)
Solvents:
52.5 parts by weight of acetone
7 parts by weight of dimethylformamide Emulsifier:

0.5 part by weight of alkylaryl polyglycol ether

To produce a suitable preparation of active compound, 1 part by weight of active compound is mixed with the stated amounts of solvents and emulsifier, and the concentrate is diluted with emulsifier-containing water to the desired concentration. If the addition of ammonium salts or/and penetrants is required, these are in each case added in a concentration of 1000 ppm to the solution of the preparation. Discs of bean leaves (*Phaseolus vulgaris*) which are infested by larvae of the leaf-mining fly (*Liriomyza trifolii*) are sprayed with an active compound preparation of the desired concentration.

After the desired period of time, the effect in % is determined 100% means that all of the leaf-mining flies have been killed; 0% means that none of the leaf-mining flies have been killed.

In this test, for example, the following compounds of the Preparation Examples show superior efficacy to the prior art: see table

*Ctenocephalides felis* Oral (CTECFE)

Solvent: 1 part by weight of dimethyl sulphoxide

For the purpose of preparing an appropriate active compound formulation, 10 mg of active compound are mixed with 0.5 ml of dimethyl sulphoxide. A portion of the concentrate is diluted with citrated cattle blood, and the desired concentration is prepared.

About 20 unfed adult fleas (*Ctenocephalides felis*) are placed into a chamber which is closed at the top and bottom with gauze. A metal cylinder whose bottom end is closed with parafilm is placed onto the chamber. The cylinder contains the blood/active compound preparation, which can be taken up by the fleas through the parafilm membrane.

After the desired period of time, the kill in % is determined 100% means that all of the fleas have been killed; 0% means that none of the fleas have been killed.

In this test, for example, the following compounds of the Preparation Examples show superior efficacy to the prior art: see table

*Musca domestica* Test (MUSCDO)

Solvent: dimethyl sulphoxide

To produce a suitable preparation of active compound, 10 mg of active compound are mixed with 0.5 ml of dimethyl sulphoxide, and the concentrate is diluted with water to the desired concentration.

Vessels containing a sponge treated with the active compound formulation of the desired concentration are populated with adult *Musca domestica*.

After the desired period of time, the kill in % is determined. 100% means that all of the flies have been killed; 0% means that none of the flies have been killed.

In this test, for example, the following compounds of the Preparation Examples show superior efficacy to the prior art: see table

*Boophilus microplus* Test (DIP)

Test animals: adult engorged *Boophilus microplus* females of the SP-resistant Parkhurst strain Solvent: dimethyl sulphoxide 10 mg of active compound are dissolved in 0.5 ml of dimethyl sulphoxide. For the purpose of preparing a suitable formulation, the active compound solution is diluted with water to the concentration desired in each case (in ppm).

This active compound preparation is pipetted into tubes. 8-10 ticks are transferred into a further tube with holes. The tube is immersed into the active compound formulation, and all ticks are completely wetted. After the liquid has run out, the ticks are transferred onto filter discs in plastic dishes and stored in a climate-controlled room.

The activity is assessed after the desired time by laying of fertile eggs. Eggs whose fertility is not evident from the outside are kept in glass tubes in a climate-controlled cabinet until the larvae have hatched. An effect of 100% means that none of the ticks has laid any fertile eggs.

In this test, for example, the following compounds of the Preparation Examples show superior efficacy to the prior art: see table

*Boophilus microplus* Test (BOOPMI Injection)

Solvent: dimethyl sulphoxide

To produce a suitable preparation of active compound, 10 mg of active compound is mixed with 0.5 ml of solvent, and the concentrate is diluted with solvent to the desired concentration (in µg/animal).

The active compound solution is injected into the abdomen (*Boophilus microplus*), and the animals are transferred into dishes and stored in a climate-controlled room.

After 7 days, the efficacy in % is determined. The activity is assessed by laying of fertile eggs. 100% means that none of the ticks has laid any fertile eggs.

In this test, for example, the following compounds of the Preparation Examples show superior efficacy to the prior art: see table

| Substance | Structure | Animal species | Concentration | % Activity dat |
|---|---|---|---|---|
| Ex. No. Ik-136 known from WO 2010/051926 A2 | 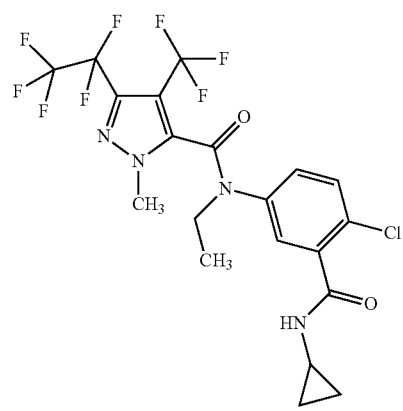 [SMILES: CCN(C(=O)c1c(C(F)(F)F)c(C(F)(F)C(F)(F)F)nn1C)c1ccc(Cl)c(C(=O)NC2CC2)c1] | MYZUPE | 20 g/ha | 0 6 dat |
| | | TETRUR | 20 g/ha | 0 6 dat |
| | | PHAECO | 0.8 ppm | 0 7 dat |
| | | NILALU | 20 g/ha | 0 7 dat |
| | | CTECFE | 0.8 ppm | 30 2 dat |
| | | BOOPMI | 0.032 µg/animal | 0 7 dat |
| | | | 20 ppm | 0 7 dat |

-continued

| Substance | Structure | Animal species | Concentration | % Activity dat |
|---|---|---|---|---|
| Ex. No. 6 according to the invention | 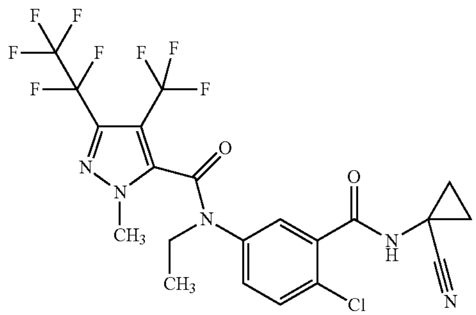 [SMILES: CCN(C(=O)c1c(C(F)(F)F)c(C(F)(F)C(F)(F)F)nn1C)c1ccc(Cl)c(C(=O)NC2(C#N)CC2)c1] | MYZUPE<br>TETRUR<br>PHAECO<br>NILALU<br>CTECFE<br>BOOPMI | 20 g/ha<br>20 g/ha<br>0.8 ppm<br>20 g/ha<br>0.8 ppm<br>0.032 µg/animal<br>20 ppm | 70 6 dat<br>100 6 dat<br>100 7 dat<br>90 7 dat<br>80 2 dat<br>70 7 dat<br>100 7 dat |
| Ex. No. Ik-132 known from WO 2010/051926 A2 | 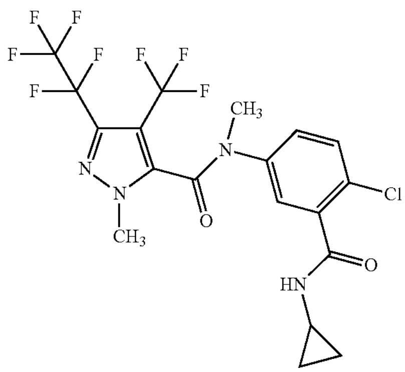 [SMILES: CN(C(=O)c1c(C(F)(F)F)c(C(F)(F)C(F)(F)F)nn1C)c1ccc(Cl)c(C(=O)NC2CC2)c1] | MYZUPE<br>PHAECO<br>PLUTMA<br>SPODFR<br>TETRUR<br>CTECFE<br>BOOPMI | 100 g/ha<br>0.8 ppm<br>20 ppm<br>20 ppm<br>4 ppm<br>0.8 ppm<br>0.032 µg/animal<br>20 ppm | 0 6 dat<br>5 7 dat<br>5 7 dat<br>50 7 dat<br>30 7 dat<br>30 2 dat<br>0 7 dat<br>30 7 dat |
| Ex. No. 8 according to the invention | 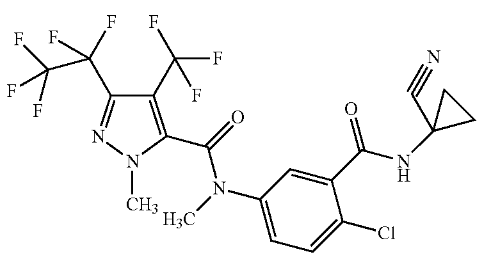 [SMILES: CN(C(=O)c1c(C(F)(F)F)c(C(F)(F)C(F)(F)F)nn1C)c1ccc(Cl)c(C(=O)NC2(C#N)CC2)c1] | MYZUPE<br>PHAECO<br>PLUTMA<br>SPODFR<br>TETRUR<br>CTECFE<br>BOOPMI | 100 g/ha<br>0.8 ppm<br>20 ppm<br>20 ppm<br>4 ppm<br>0.8 ppm<br>0.032 µg/animal<br>20 ppm | 100 6 dat<br>100 7 dat<br>100 7 dat<br>100 7 dat<br>95 7 dat<br>90 2 dat<br>100 7 dat<br>100 7 dat |
| Ex. No. Ik-1 known from WO 2010/051926 A2 | 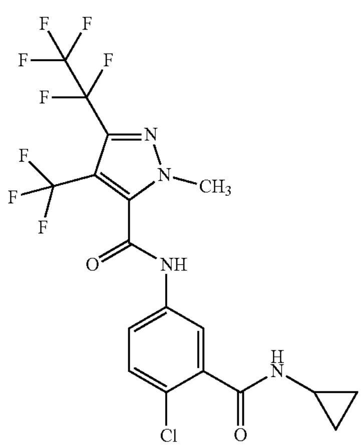 [SMILES: Cn1nc(C(F)(F)C(F)(F)F)c(C(F)(F)F)c1C(=O)Nc1ccc(Cl)c(C(=O)NC2CC2)c1] | SPODFR<br>HELIAR<br>TETRUR<br>FRANOC<br>NILALU<br>CTECFE | 20 ppm<br>20 ppm<br>4 ppm<br>20 g/ha<br>500 g/ha<br>0.8 ppm | 20 7 dat<br>45 7 dat<br>40 7 dat<br>0 7 dat<br>0 7 dat<br>0 2 dat |

-continued

| Substance | Structure | Animal species | Concentration | % Activity dat |
|---|---|---|---|---|
| Ex. No. Ik-296 known from WO 2010/051926 A2 | 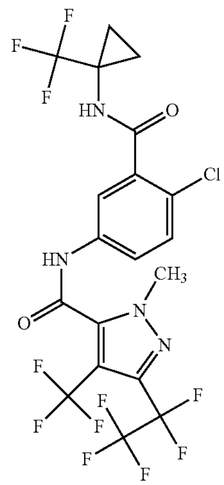 [SMILES: Cn1nc(C(F)(F)C(F)(F)F)c(C(F)(F)F)c1C(=O)Nc1ccc(Cl)c(C(=O)NC2(C(F)(F)F)CC2)c1] | MYZUPE<br>FRANOC<br>LIRITR<br>NILALU | 100 g/ha<br>500 g/ha<br>500 g/ha<br>500 g/ha | 0 6 dat<br>60 7 dat<br>0 7 dat<br>0 7 dat |
| Ex. No. Ik-47 known from WO 2010/051926 A2 | 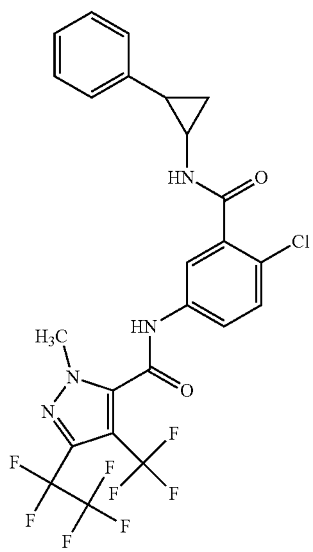 [SMILES: Cn1nc(C(F)(F)C(F)(F)F)c(C(F)(F)F)c1C(=O)Nc1ccc(Cl)c(C(=O)NC2CC2c2ccccc2)c1] | MYZUPE<br>PHAECO<br>PLUTMA<br>SPODFR<br>HELIAR<br>TETRUR<br>FRANOC<br>NILALU<br>CTECFE<br>MUSCDO<br>BOOPMI | 500 g/ha<br>20 g/ha<br>20 ppm<br>20 ppm<br>20 ppm<br>20 ppm<br>500 g/ha<br>500 g/ha<br>20 ppm<br>100 ppm<br>0.8 µg/animal | 0 6 dat<br>0 7 dat<br>0 7 dat<br>0 7 dat<br>0 7 dat<br>30 7 dat<br>0 7 dat<br>0 7 dat<br>50 2 dat<br>0 2 dat<br>50 7 dat |
| Ex. No. Ik-286 known from WO 2010/051926 A2 | 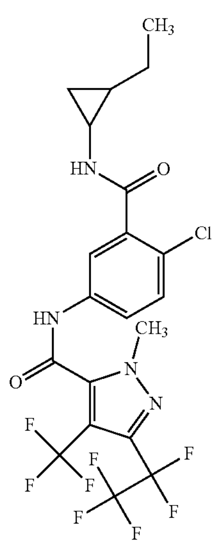 [SMILES: CCC1CC1NC(=O)c1cc(NC(=O)c2c(C(F)(F)F)c(C(F)(F)C(F)(F)F)nn2C)ccc1Cl] | MYZUPE<br>PHAECO<br>CTECFE<br>BOOPMI | 20 g/ha<br>100 g/ha<br>4 ppm<br>100 ppm<br>0.16 µg/animal | 0 6 dat<br>0 7 dat<br>0 2 dat<br>40 7 dat<br>20 7 dat |

-continued

| Substance | Structure | Animal species | Concentration | % Activity dat |
|---|---|---|---|---|
| Ex. No. Ik-279 known from WO 2010/051926 A2 | 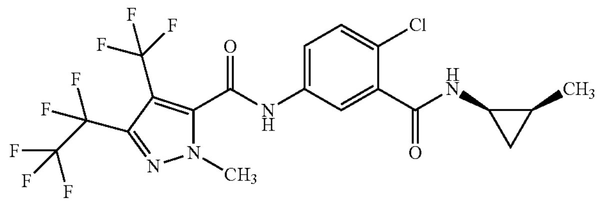 [SMILES: C[C@H]1C[C@H]1NC(=O)c1cc(NC(=O)c2c(C(F)(F)F)c(C(F)(F)C(F)(F)F)nn2C)ccc1Cl] | MYZUPE<br>PHAECO<br>SPODFR<br>TETRUR | 20 g/ha<br>20 g/ha<br>100 g/ha<br>4 ppm | 0 6 dat<br>0 7 dat<br>50 7 dat<br>0 7 dat |
| Ex. No. Ik-280 known from WO 2010/051926 A2 | 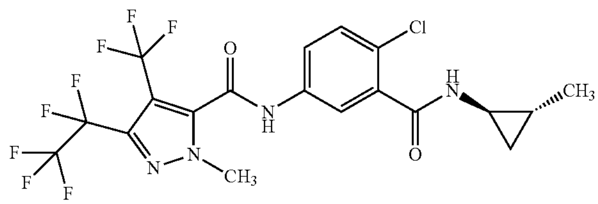 [SMILES: C[C@@H]1C[C@H]1NC(=O)c1cc(NC(=O)c2c(C(F)(F)F)c(C(F)(F)C(F)(F)F)nn2C)ccc1Cl] | PLUTMA<br>PHAECO<br>SPODFR<br>HELIAR<br>NILALU | 20 ppm<br>4 ppm<br>20 ppm<br>100 ppm<br>100 g/ha | 65 7 dat<br>0 7 dat<br>40 7 dat<br>0 7 dat<br>0 7 dat |
| Ex. No. 10 according to the invention | 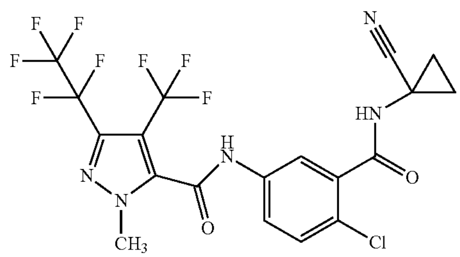 [SMILES: Cn1nc(C(F)(F)C(F)(F)F)c(C(F)(F)F)c1C(=O)Nc1ccc(Cl)c(C(=O)NC2(C#N)CC2)c1] | MYZUPE<br><br><br>PHAECO<br><br><br>SPODFR<br><br>PLUTMA<br>HELIAR<br><br>TETRUR<br><br>FRANOC<br><br>LIRITR<br>NILALU<br><br>CTECFE<br><br><br>MUSCDO<br>BOOPMI<br><br> | 500 g/ha<br>100 g/ha<br>20 g/ha<br>100 g/ha<br>20 g/ha<br>4 ppm<br>100 g/ha<br>20 ppm<br>20 ppm<br>100 ppm<br>20 ppm<br>20 ppm<br>4 ppm<br>500 g/ha<br>20 g/ha<br>500 g/ha<br>500 g/ha<br>100 g/ha<br>20 ppm<br>4 ppm<br>0.8 ppm<br>100 ppm<br>0.8 µg/animal<br>0.16 µg/animal<br>100 ppm | 100 6 dat<br>100 6 dat<br>80 6 dat<br>100 7 dat<br>100 7 dat<br>100 7 dat<br>100 7 dat<br>100 7 dat<br>100 7 dat<br>100 7 dat<br>100 7 dat<br>100 7 dat<br>100 7 dat<br>100 7 dat<br>90 7 dat<br>100 7 dat<br>100 7 dat<br>100 7 dat<br>100 2 dat<br>98 2 dat<br>90 2 dat<br>100 2 dat<br>100 7 dat<br>80 7 dat<br>100 7 dat |
| Ex. No. Ik-175 known from WO 2010/051926 A2 | 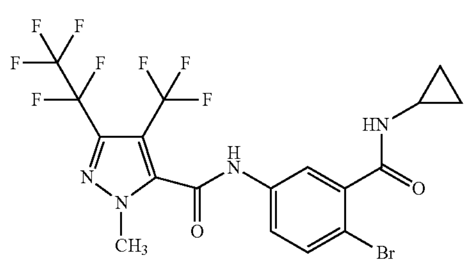 [SMILES: Cn1nc(C(F)(F)C(F)(F)F)c(C(F)(F)F)c1C(=O)Nc1ccc(Br)c(C(=O)NC2CC2)c1] | MYZUPE<br>PHAECO<br>NILALU | 100 g/ha<br>4 ppm<br>500 g/ha | 0 6 dat<br>10 7 dat<br>0 7 dat |
| Ex. No. 14 according to the invention | 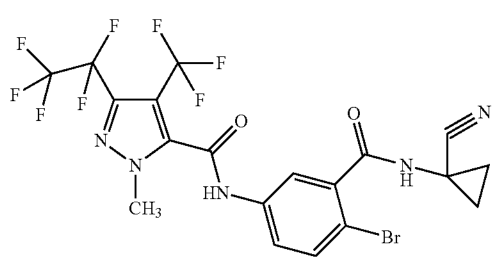 [SMILES: Cn1nc(C(F)(F)C(F)(F)F)c(C(F)(F)F)c1C(=O)Nc1ccc(Br)c(C(=O)NC2(C#N)CC2)c1] | MYZUPE<br>PHAECO<br>NILALU | 100 g/ha<br>4 ppm<br>500 g/ha | 100 6 dat<br>100 7 dat<br>80 4 dat |

| Substance | Structure | Animal species | Concentration | % Activity dat |
|---|---|---|---|---|
| Ex. No. Ik-155 known from WO 2010/051926 A2 | 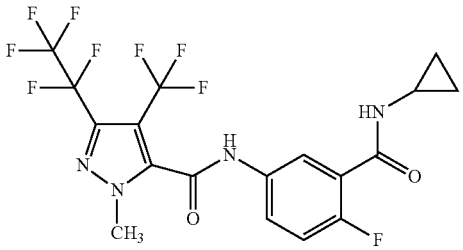 [SMILES: Cn1nc(C(F)(F)C(F)(F)F)c(C(F)(F)F)c1C(=O)Nc1ccc(F)c(C(=O)NC2CC2)c1] | MYZUPE<br>TETRUR | 100 g/ha<br>100 g/ha | 0 6 dat<br>0 6 dat |
| Ex. No. 14 according to the invention | 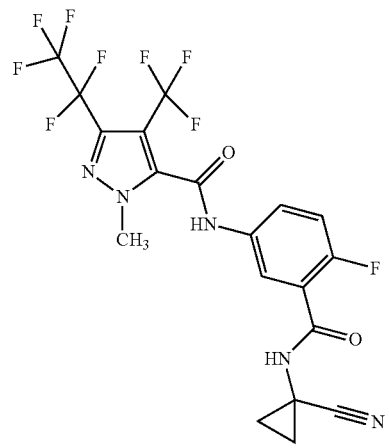 [SMILES: Cn1nc(C(F)(F)C(F)(F)F)c(C(F)(F)F)c1C(=O)Nc1ccc(F)c(C(=O)NC2(C#N)CC2)c1] | MYZUPE<br>TETRUR | 100 g/ha<br>100 g/ha | 100 6 dat<br>100 6 dat |

The invention claimed is:

1. A compound of formula (I)

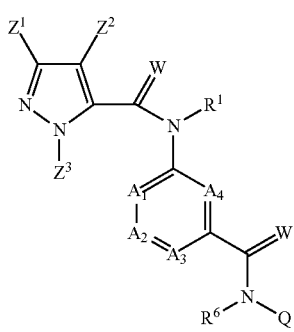

in which $Z^1$ represents trifluoromethyl, 1-chlorocyclopropyl, 1-fluorocyclopropyl or pentafluoroethyl, $Z^2$ represents trifluoromethyl, nitro, methylthio, methylsulphinyl, methylsulphonyl, fluorine, chlorine, bromine or iodine, $Z^3$ represents methyl, ethyl, n-propyl or hydrogen, $R^1$ represents hydrogen, methyl, ethyl, n-propyl, isopropyl, n-butyl, isobutyl, s-butyl, t-butyl, methoxymethyl, ethoxymethyl, propoxymethyl, methylcarbonyl, ethylcarbonyl, n-propylcarbonyl, isopropylcarbonyl, s-butylcarbonyl, t-butylcarbonyl, methoxycarbonyl, ethoxycarbonyl, n-propoxycarbonyl, isopropoxycarbonyl, s-butoxycarbonyl, t-butoxycarbonyl, cyanomethyl, 2-cyanoethyl, benzyl, 4-methoxybenzyl, pyrid-2-ylmethyl, pyrid-3-ylmethyl, pyrid-4-ylmethyl, or 4-chloropyrid-3-ylmethyl, $A^1$, $A^2$ and $A^4$ represent CH, $A_3$ represents $CR^4$ and $R^4$ represents fluorine, chlorine, bromine or iodine, $R^6$ represents hydrogen, methyl, ethyl, n-propyl, isopropyl, n-butyl, isobutyl, s-butyl, or t-butyl, W represents oxygen and Q represents 1-cyanocyclopropyl.

2. A compound of formula (I) according to claim 1, in which $Z^1$ represents trifluoromethyl, 1-chlorocyclopropyl, 1-fluorocyclopropyl or pentafluoroethyl, $Z^2$ represents trifluoromethyl, or chlorine, $Z^3$ represents methyl, $R^1$ represents hydrogen, methyl, or ethyl, $A^1$, $A^2$ and $A^4$ represent CH, $A_3$ represents $CR^4$ and $R^4$ represents chlorine, $R^6$ represents hydrogen, methyl or ethyl, W represents oxygen and Q represents 1-cyanocyclopropyl.

3. A compound of formulae (IVa) or (IVb),

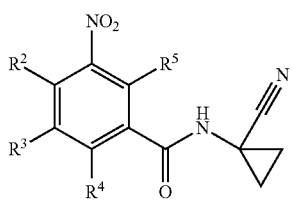
(IVb)

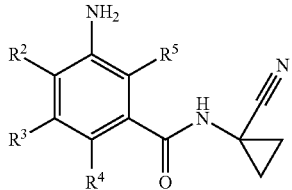
(IVa)

in which

R², R³, R⁴ and R⁵ independently of one another represent hydrogen, halogen, cyano, nitro, optionally substituted $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_1$-$C_6$-alkylamino, N,N-di-$C_1$-$C_6$-alkylamino, N—$C_1$-$C_6$-alkylaminocarbonyl, N—$C_3$-$C_6$-cycloalkylaminocarbonyl or ($C_1$-$C_3$-alkoxy)carbonyl.

4. A compound of formulae (Va) or (Vb) in which

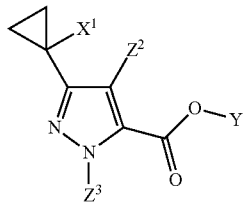
(Vb)

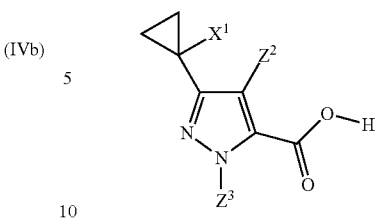
(Va)

X¹ represents halogen, cyano or $C_1$-$C_4$-haloalkyl, and

Z² represents halogen, cyano, nitro or optionally substituted $C_1$-$C_6$-haloalkyl, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, or $C_1$-$C_6$-haloalkylsulphonyl, and Z³ represents hydrogen or optionally substituted $C_1$-$C_6$-alkyl, $C_1$-$C_4$-alkenyl, $C_1$-$C_4$-alkynyl, or $C_1$-$C_6$-haloalkyl, and Y represents optionally substituted $C_1$-$C_6$-alkyl.

5. A seed treated with a compound of formula (I) according to claim 1.

6. A medicament comprising a compound according to claim 1.

7. A pharmaceutical composition for controlling a parasite on an animal comprising a compound of formula (I) according to claim 1.

8. A pharmaceutical composition comprising at least one compound according to claim 1.

9. A crop protection composition comprising a compound of formula (I) according to claim 1, and at least one extender and/or surfactant.

10. A process for preparing a crop protection composition comprising mixing a compound of formula (I) according to claim 1, and at least one customary extender and/or surfactant.

11. A method for controlling a pest, comprising allowing a compound of formula (I) according to claim 1, to act on a pest and/or a habitat thereof.

12. A method for controlling an insect, an arachnid or a nematode, comprising allowing a compound of formula (I) according to claim 1 to act on an insect, an arachnid and/or a nematode, and/or a habitat thereof.

* * * * *